(12) United States Patent
Grushin et al.

(10) Patent No.: US 8,212,075 B2
(45) Date of Patent: Jul. 3, 2012

(54) PROCESS FOR PREPARING 2-AMINO-5-CYANOBENZOIC ACID DERIVATIVES

(75) Inventors: Vladimir Grushin, Hockessin, DE (US); Albert Loren Casalnuovo, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 77 days.

(21) Appl. No.: 12/741,635

(22) PCT Filed: Nov. 7, 2008

(86) PCT No.: PCT/US2008/082739
§ 371 (c)(1),
(2), (4) Date: Aug. 12, 2010

(87) PCT Pub. No.: WO2009/061991
PCT Pub. Date: May 14, 2009

(65) Prior Publication Data
US 2011/0034695 A1    Feb. 10, 2011

Related U.S. Application Data

(60) Provisional application No. 61/002,299, filed on Nov. 8, 2007.

(51) Int. Cl.
C07C 231/12    (2006.01)
(52) U.S. Cl. .................................... 564/124
(58) Field of Classification Search ............... None
See application file for complete search history.

(56) References Cited

U.S. PATENT DOCUMENTS
8,034,968 B2 * 10/2011 Annis .................... 558/415

FOREIGN PATENT DOCUMENTS
| EP | 0613719 A | 9/1994 |
| WO | 2004/067528 A1 | 8/2004 |
| WO | 2006/062978 A1 | 6/2006 |
| WO | 2006/068669 A1 | 6/2006 |

OTHER PUBLICATIONS

J. P. Wolfe et al., "Nickel-Catalyzed Amination of Aryl Chlorides", *J. Am. Chem. Soc.* 1997, vol. 119, pp. 6054-6058.
J. Pawlas et al., "A General Nickel-Catalyzed Hydroamination of 1,3-Dienes by Alkylamines: Catalyst Selection, Scope and Mechanism", *J. Am. Chem. Soc.* 2002, vol. 124, pp. 3669-3679.

* cited by examiner

*Primary Examiner* — Kamal Saeed
(74) *Attorney, Agent, or Firm* — Renee M. Lett

(57) ABSTRACT

Disclosed is a method for preparing a compound of Formula 1 comprising contacting a compound of Formula 2 with at least one alkali metal cyanide of Formula 3 and a compound of Formula 4.

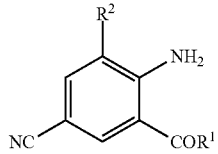

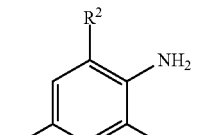

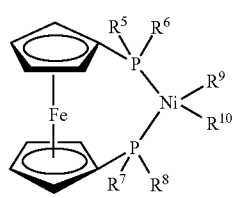

wherein $R^1$ is $NHR^3$ or $OR^4$; $R^2$ is $CH_3$ or Cl; $R^3$ is H, $C_1$-$C_4$ alkyl, cyclopropyl, cyclopropylcyclopropyl, cyclopropylmethyl or methylcyclopropyl; $R^4$ is H or $C_1$-$C_4$ alkyl; X is Br, Cl or I; and $R^5$, $R^6$, $R^7$, $R^8$, $R^9$ and $R^{10}$ are as defined in the disclosure.

Also disclosed is a method for preparing a compound of Formula 4 wherein $R^9$ and $R^{10}$ together are a cycloalkadiene bidentate ligand, comprising contacting a compound of Formula 5 wherein Y is Cl, Br or I, with a cycloalkadiene bidentate ligand, at least one metal reducing agent and a nitrile solvent.

Also disclosed is a method for preparing a compound of Formula 1 comprising preparing a compound of Formula 4 by contacting a compound of Formula 5 with a cycloalkadiene bidentate ligand and at least one metal reducing agent, and then contacting the reaction mixture comprising the compound of Formula 4 with a compound of Formula 2 and at least one alkali metal cyanide of Formula 3; and further disclosed is a method for preparing a compound of Formula 6 wherein $R^{15}$, $R^{16}$, $R^{17}$ and Z are as defined in the disclosure using a compound of Formula 1, characterized by preparing the compound of Formula 1 by a method disclosed above.

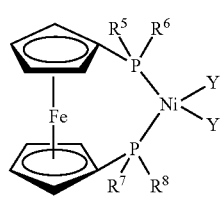

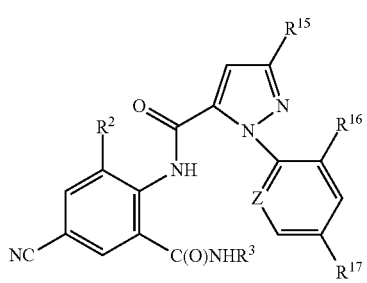

13 Claims, No Drawings

US 8,212,075 B2

PROCESS FOR PREPARING 2-AMINO-5-CYANOBENZOIC ACID DERIVATIVES

FIELD OF THE INVENTION

The present invention pertains to a method for the preparation of 3-substituted 2-amino-5-cyanobenzoic acid derivatives.

BACKGROUND OF THE INVENTION

Preparation of certain 2-amino-5-cyanobenzoic acids and their utility as intermediates for preparing corresponding insecticidal cyanoanthranilic diamides has been disclosed (see e.g., Scheme 9 in PCT Patent Publication WO 2004/067528; Scheme 9 and Example 2, Step A in PCT Patent Publication WO 2006/068669; and Scheme 15 and Example 6, Step B in PCT Patent Publication WO 2006/062978).

European Patent Application EP 613719 discloses a method for cyanation of certain aromatic compounds via halide replacement using an alkali metal cyanide in the presence of a phosphine-nickel catalyst and a salt of a transition metal.

However, the need continues for new or improved methods suitable for rapidly providing 2-amino-5-cyanobenzoic acid derivatives.

SUMMARY OF THE INVENTION

The present invention is directed to a method for preparing a compound of Formula 1

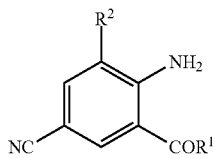

1 wherein
  $R^1$ is $NHR^3$ or $OR^4$;
  $R^2$ is $CH_3$ or Cl;
  $R^3$ is H, $C_1$-$C_4$ alkyl, cyclopropyl, cyclopropylcyclopropyl, cyclopropylmethyl or methylcyclopropyl; and
  $R^4$ is H or $C_1$-$C_4$ alkyl;
comprising contacting (1) a compound of Formula 2

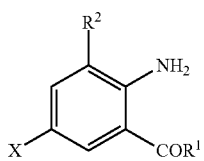

2 wherein X is Br, Cl or I;
with (2) at least one compound of Formula 3

$M^1CN$  3 wherein $M^1$ is sodium, potassium, cesium or rubidium; and (3) a compound of Formula 4

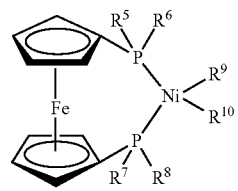

4 wherein
  $R^5$ is a phenyl ring optionally substituted with up to 5 substituents independently selected from $R^{11}$;
  $R^6$ is a phenyl ring or a naphthalenyl ring system, each ring or ring system optionally substituted with up to 5 substituents independently selected from $R^{12}$;
  $R^7$ is a phenyl ring optionally substituted with up to 5 substituents independently selected from $R^{13}$;
  $R^8$ is a phenyl ring or a naphthalenyl ring system, each ring or ring system optionally substituted with up to 5 substituents independently selected from $R^{14}$;
  each $R^9$ and $R^{10}$ is independently a displaceable ligand; or
    $R^9$ and $R^{10}$ together are a bidentate, displaceable ligand; and
  each $R^{11}$, $R^{12}$, $R^{13}$ and $R^{14}$ is independently fluorine, $C_1$-$C_6$ alkyl, $C_1$-$C_6$ fluoroalkyl, $C_1$-$C_6$ alkoxy, $C_1$-$C_6$ fluoroalkoxy, $C_1$-$C_6$ alkylamino or $C_2$-$C_6$ dialkylamino;
  provided that when X is Cl, then $R^2$ is methyl.

This invention also provides a method for preparing a compound of Formula 4 wherein $R^9$ and $R^{10}$ together are a cycloalkadiene bidentate ligand;
comprising contacting (i) a compound of Formula 5

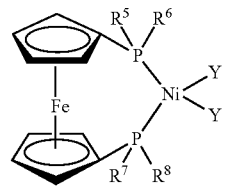

5 wherein each Y is independently Cl, Br or I;
with (ii) a cycloalkadiene bidentate ligand, (iii) at least one metal reducing agent and (iv) a nitrile solvent.

This invention also provides a method for preparing a compound of Formula 1 (as defined above) comprising contacting (a) a compound of Formula 5

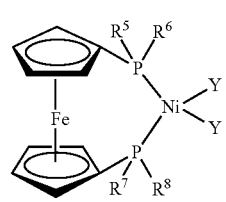

5 wherein each Y is independently Cl, Br or I;
with (b) a cycloalkadiene bidentate ligand and (c) at least one metal reducing agent to form a mixture comprising a compound of Formula 4 wherein $R^9$ and $R^{10}$ together are a cycloalkadiene bidentate ligand; and then contacting said mixture comprising the compound of Formula 4 with (1) a compound of Formula 2 and (2) at least one compound of Formula 3.

This invention also provides a method for preparing a compound of Formula 6

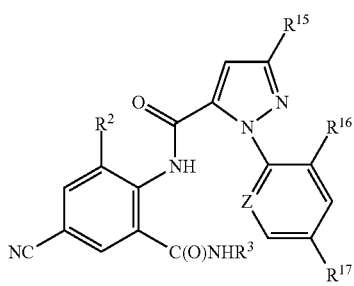

wherein
$R^2$ is $CH_3$ or Cl;
$R^3$ is H, $C_1$-$C_4$ alkyl, cyclopropyl, cyclopropylcyclopropyl, cyclopropylmethyl or methylcyclopropyl;
Z is $CR^{18}$ or N;
$R^{15}$ is Cl, Br, $CF_3$, $OCF_2H$ or $OCH_2CF_3$;
$R^{16}$ is F, Cl or Br;
$R^{17}$ is H, F or Cl; and
$R^{18}$ is H, F, Cl or Br;
using a compound of Formula 1. The method is characterized by (A) preparing the compound of Formula 1 from the compound of Formula 2 by a method disclosed above, or (B) using as said compound of Formula 1 a compound of Formula 1 prepared by a method disclosed above.

Further related aspects of the present invention pertain to combinations of the aforedescribed methods, including a method for preparing a compound of Formula 6 comprising preparing a compound of Formula 4 from a compound of Formula 5 using the method described above then preparing a compound of Formula 1 from the compounds of Formulae 2, 3 and 4 as described above, and then preparing the compound of Formula 6 using the compound of Formula 1. Another combination pertains to the method of preparing a compound of Formula 6 comprising preparing a compound of Formula 1 by the method comprising preparing a compound of Formula 4 from a compound of Formula 5 and contacting the reaction mixture comprising the compound of Formula 4 with the compounds of Formulae 2 and 3 to prepare a compound of Formula 1, and then preparing the compound of Formula 6 using the compound of Formula 1.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl" includes straight-chain or branched alkyl, such as, methyl, ethyl, butyl, n-propyl, i-propyl, or the different butyl isomers.

The term "cyclopropylcyclopropyl," denotes cyclopropyl substitution on another cyclopropyl ring. Examples of "cyclopropylcyclopropyl," include 1,1'-bicyclopropyl-1-yl, 1,1'-bicyclopropyl-2-yl and the different cis- and trans-cyclopropylcyclopropyl isomers such as (1R,2S)-1,1'-bicyclopropyl-2-yl and (1R,2R)-1,1'-bicyclopropyl-2-yl.

"Alkoxy" includes, for example, methoxy, ethoxy, n-propyloxy, isopropyloxy and the different butoxy, pentoxy and hexyloxy isomers. "Alkylamino" includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$.

The term "halogen", either alone or in compound words such as "haloalkyl", includes fluorine, chlorine, bromine or iodine. Furthermore, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. Examples of "fluoroalkyl" include $F_3C$, $CF_3CH_2$ and $CF_3CF_2$.

In the present invention, ratios are generally recited as single numbers, which are relative to the number 1; for example, a ratio of 4 means 4:1.

In the context of the present invention the term "reducing agent" means a chemical species or mixture of compound species capable of providing electrons to another chemical species (e.g., to decrease the oxidation state of the other chemical species). In one aspect of the present invention, reducing agents are used to reduce (i.e. decrease the oxidation state) of nickel from +2 in a compound of Formula 5 to 0 to allow formation of a compound of Formula 4.

In the context of the present invention the term "silane reducing agent" means a silane or mixture of silanes, wherein in this context silane refers to a molecule comprising at least one silicon-hydrogen bond (i.e. Si—H). For the present methods, a particularly useful silane reducing agent is polymethylhydrosiloxane, alternatively named poly(methylhydrosiloxane), (Formula A) although other silane reducing agents can be used as well.

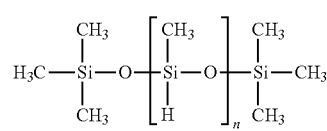

wherein n is a large integer or range of integers typical of polymers.

The terms "equivalent ratio" and "equivalent percentage" are used herein to describe amounts of reducing agents relative to amounts of other reactants in the present methods. "Equivalent percentage" is calculated by multiplying the equivalent ratio (relative to the number 1) by 100.

In methods relating to the reduction of the +2 oxidation state of nickel to the 0 oxidation state (e.g., preparation of a compound of Formula 4 from a compound of Formula 5), an equivalent is considered to correspond to 2 moles of electrons, because 2 electrons are required to reduce nickel from its +2 oxidation state to its 0 oxidation state. Therefore a mole of nickel (e.g., the compound of Formula 5) being reduced from the +2 to 0 oxidation state is considered to be one equivalent. The reducing agent zinc metal provides 2 electrons in going from its 0 oxidation state to its +2 oxidation state, and therefore in the context of reducing nickel, 1 mole of zinc is considered to be 1 equivalent of zinc. Accordingly the equivalent ratio (i.e. ratio of equivalents) of zinc relative to nickel (e.g., the compound of Formula 5) is the same as the molar ratio (i.e. ratio of moles of zinc to moles of nickel). The equivalent ratio relative to nickel for a reducing agent providing other than 2 electrons can be calculated by dividing the molar ratio of reducing agent relative to nickel (e.g., the compound of Formula 5) by 2 and then multiplying the quotient by the number of electrons provided by the reducing agent when it is oxidized (e.g., 1 for lithium metal, 3 for aluminum metal).

In methods wherein there is no formal, permanent reduction of reactants forming the product (e.g., preparation of a compound of Formula 1 from compounds of Formulae 2 and 3 in the presence of a compound of Formula 4), the reaction stoichiometry requires no electrons for reduction. Nevertheless as reported in the present disclosure, for some methods the inclusion of one or more reducing agents in the reaction mixture has been discovered to increase the yield and/or purity of the product. In this context, an equivalent of a reducing agent is considered to correspond to 1 mole of electrons. Therefore in this context, 1 mole of zinc metal is considered to correspond to 2 equivalents as a reducing agent, because 1 mole of zinc provides 2 moles of electrons in going from the 0 to +2 oxidation state. Silane reducing agents such as polymethylhydrosiloxane provide an electron in the form of hydride ion (i.e. H⁻), and therefore a mole of polymethylhydrosiloxane of Formula A wherein n is 50 corresponds to 50 equivalents as a reducing agent in this context. When n is a large number in Formula A, the contribution of capping trimethylsilyl groups to total molecular weight becomes relatively insignificant, so that the equivalent weight of this compound as a reducing agent in this context corresponds to about 60.13 g per mole of hydride ions (which are equivalent to electrons). Furthermore in this context, the number of equivalents of the compound (e.g., the compound of Formula 2) to which the amount of reducing agent is compared in calculating the equivalent ratio is considered to be the same as the number of moles of the compound added to the reaction mixture.

In the context of the present invention the term "metal reducing agent" refers to any elemental metal which is more electropositive than nickel, and is in powder form. Examples include, but are not limited to, zinc and manganese, including alloys comprising them (e.g., manganese-iron alloy).

As used herein, the term "ligand" refers to an organic molecule comprising at least one pair of electrons available for coordination with a metal atom (in this case a nickel atom). The term "bidentate ligand" refers to an organic molecule comprising at least two electron pairs that are available for coordination with a metal atom (nickel atom). The term "displaceable ligand" denotes a ligand that can be displaced from a nickel atom in a nickel complex under the reaction conditions that are being employed. Nickel complex refers to a coordination compound wherein the nickel atom is bonded via coordinate covalent bonds to one or more ligands.

As used herein the structure

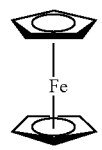

means ferrocene.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and 0 to 3 heteroatoms. Of note are carbon-based radicals selected from $C_1$-$C_4$ alkyl, $C_1$-$C_2$ haloalkyl and phenyl optionally substituted with 1-3 substituents selected from $C_1$-$C_3$ alkyl, halogen and nitro.

As referred to in the present disclosure, the term "carboxylic acid" means an organic chemical compound comprising at least one carboxylic acid functional group (i.e. —C(O)OH). The term "carboxylic acid" does not include the compound carbonic acid (i.e. HOC(O)OH). Carboxylic acids include, for example, formic acid, acetic acid, propionic acid, chloroacetic acid, benzoic acid, maleic acid, and citric acid. The term "effective $pK_a$" refers to the $pK_a$ of the carboxylic acid functional group, or if the compound has more than one carboxylic acid functional group, "effective $pK_a$" refers to the $pK_a$ of the most acidic carboxylic acid functional group. As referred to herein, the "effective pH" of a nonaqueous substance or mixture, such as a reaction mixture, is determined by mixing an aliquot of the substance or mixture with about 5 to 20 volumes of water and then measuring the pH of the resulting aqueous mixture (e.g., with a pH meter). As referred to herein, a "substantially anhydrous" substance means the substance contains no more than about 1% water by weight. The chemical name "isatoic anhydride" is another name corresponding to the current Chemical Abstracts name "2H-3,1-benzoxazine-2,4(1H)-dione".

Embodiments of the present invention include:

Embodiment A1. The method described in the Summary of the Invention for preparing a compound of Formula 1 comprising contacting reagent (1) (i.e. a compound of Formula 2) with reagent (2) (i.e. at least one compound of Formula 3) and reagent (3) (i.e. a compound of Formula 4).

Embodiment A2. The method of Embodiment A1 wherein reagent (1), reagent (2) and reagent (3) are contacted in the presence of at least one reducing agent.

Embodiment A3. The method of Embodiment A2 wherein the reducing agent comprises one or more compounds selected from the group consisting of metal reducing agents (e.g., zinc, manganese) and silane reducing agents (e.g., polymethylhydrosiloxane).

Embodiment A3a. The method of Embodiment A3 wherein the reducing agent comprises one or more compounds selected from the group consisting of zinc and polymethylhydrosiloxane.

Embodiment A4. The method of Embodiment A3a wherein the reducing agent comprises zinc.

Embodiment A5. The method of Embodiment A3 wherein the reducing agent comprises polymethylhydrosiloxane.

Embodiment A6. The method of Embodiment A3 wherein the reducing agent comprises zinc and polymethylhydrosiloxane.

Embodiment A7. The method of any one of Embodiments A1 through A6 wherein $R^1$ is $NHR^3$.

Embodiment A8. The method of any one of Embodiments A1 through A7 wherein $R^3$ is $C_1$-$C_4$ alkyl, cyclopropyl, cyclopropylcyclopropyl, cyclopropylmethyl or methylcyclopropyl.

Embodiment A9. The method of Embodiment A8 wherein $R^3$ is $C_1$-$C_4$ alkyl or cyclopropylmethyl.

Embodiment A10. The method of Embodiment A9 wherein $R^3$ is methyl.

Embodiment 10a. The method of any one of Embodiments A1 through A10 wherein X is Br or Cl.

Embodiment 10b. The method of Embodiment A10a wherein X is Br.

Embodiment A11. The method of any one of Embodiments A1 through A10b wherein $M^1$ is sodium or potassium.

Embodiment A12. The method of Embodiment A11 wherein $M^1$ is sodium.

Embodiment A13. The method of any one of Embodiments A1 through A12 wherein $R^9$ and $R^{10}$ together are a bidentate, displaceable ligand.

Embodiment A14. The method of any one of Embodiments A1 through A13 wherein $R^9$ and $R^{10}$ together are 1,5-cyclooctadiene (bonded to the nickel atom through both alkene bonds).

Embodiment A15. The method of any one of Embodiments A1 through A14 wherein the mole ratio of reagent (2) to reagent (1) is at least about 1.

Embodiment A16. The method of Embodiment A15 wherein the mole ratio of reagent (2) to reagent (1) is at least about 1.5.

Embodiment A17. The method of any one of Embodiments A1 through A16 wherein the mole ratio of reagent (2) to reagent (1) is not larger than about 5.

Embodiment A18. The method of Embodiment A17 wherein the mole ratio of reagent (2) to reagent (1) is not larger than about 2.

Embodiment A19. The method of any one of Embodiments A2 through A18 wherein the equivalent percentage of the reducing agent to reagent (1) is at least about 1%.

Embodiment A19a. The method of Embodiment A19 wherein the equivalent percentage of the reducing agent to reagent (1) is at least about 5%.

Embodiment A20. The method of Embodiment A19a wherein the equivalent percentage of the reducing agent to reagent (1) is at least about 10%.

Embodiment A21. The method of Embodiment A20 wherein the equivalent percentage of the reducing agent to reagent (1) is at least about 40%.

Embodiment A22. The method of Embodiment A21 wherein the equivalent percentage of the reducing agent to reagent (1) is at least about 20%.

Embodiment A23. The method of any one of Embodiments A2 through A22 wherein the equivalent percentage of the reducing agent to reagent (1) is not larger than about 100%.

Embodiment A23a. The method of Embodiment A23 wherein the equivalent percentage of the reducing agent relative to reagent (1) is not larger than about 80%.

Embodiment A24. The method of Embodiment A23a wherein the equivalent percentage of the reducing agent relative to reagent (1) is not larger than about 60%.

Embodiment A25. The method of Embodiment A24 wherein the equivalent percentage of the reducing agent relative to reagent (1) is not larger than about 50%.

Embodiment A26. The method of any one of Embodiments A1 through A25 wherein the mole percentage of reagent (3) to reagent (1) is at least about 0.1%.

Embodiment A27. The method of Embodiment A26 wherein the mole percentage of reagent (3) to reagent (1) is at least about 0.5%.

Embodiment A28. The method of Embodiment A27 wherein the mole percentage of reagent (3) to reagent (1) is least about 0.75%.

Embodiment A29. The method of Embodiment A28 wherein the mole percentage of reagent (3) to reagent (1) is at least about 1%.

Embodiment A30. The method of any one of Embodiments A1 through A25 wherein the mole percentage of reagent (3) to reagent (1) is not larger than about 5%.

Embodiment A31. The method of Embodiment A30 wherein the mole percentage of reagent (3) to reagent (1) is not larger than about 3%.

Embodiment A32. The method of Embodiment A31 wherein the mole percentage of reagent (3) to reagent (1) is not larger than about 1.5%.

Embodiment A33. The method of any one of Embodiments A1 through A32 wherein reagent (1), reagent (2) and reagent (3) are contacted in the presence of a suitable solvent.

Embodiment A34. The method of any one of Embodiments A1 through A32 wherein reagent (1), reagent (2), reagent (3) and at least one reducing agent are contacted in the presence of a suitable solvent.

Embodiment A35. The method of any one of Embodiments A33 and A34 wherein the suitable solvent comprises one or more solvents selected from the group consisting of nitriles (e.g., acetonitrile, propionitrile, butyronitrile), ethers (e.g., tetrahydrofuran) and halogenated and nonhalogenated aromatic hydrocarbons (e.g., xylenes, toluene, chlorobenzene, dichlorobenzene).

Embodiment A36. The method of Embodiment A35 wherein the suitable solvent comprises one or more nitrile solvents.

Embodiment A36a. The method of Embodiment A36 wherein the suitable solvent comprises one or more solvents selected from the group consisting of acetonitrile, propionitrile and butyronitrile.

Embodiment A37. The method of Embodiment A36a wherein the suitable solvent comprises acetonitrile.

Embodiment A38. The method of any one of Embodiments A34 through A37 wherein the ratio of the volume of the suitable solvent to the weight of reagent (1) is at least about 4 mL/g.

Embodiment A39. The method of Embodiment A38 wherein the ratio of the volume of the suitable solvent to the weight of reagent (1) is at least about 5 mL/g.

Embodiment A40. The method of any one of Embodiments A34 through A39 wherein the ratio of the volume of the suitable solvent to the weight of reagent (1) is not larger than about 20 mL/g.

Embodiment A41. The method of Embodiment A40 wherein the ratio of the volume of the suitable solvent to the weight of the reagent (1) is not larger than about 15 mL/g.

Embodiment A42. The method of Embodiment A41 wherein the ratio of the volume of the suitable solvent to the weight of reagent (1) is not larger than about 8 mL/g.

Embodiment A43. The method of any one of Embodiments A34 through A42 wherein reagent (1), reagent (2), reagent (3) and at least one reducing agent are contacted with the suitable solvent at a temperature not greater than about 100° C.

Embodiment A44. The method of Embodiment A43 wherein reagent (1), reagent (2), reagent (3) and at least one reducing agent are contacted with the suitable solvent at a temperature not greater than about 85° C.

Embodiment A45. The method of Embodiment A44 wherein reagent (1), reagent (2), reagent (3) and at least one reducing agent are contacted with the suitable solvent at a temperature not greater than about 80° C.

Embodiment A46. The method of any one of Embodiments A34 through A45 wherein reagent (1), reagent (2), reagent (3) and at least one reducing agent are contacted with the suitable solvent at a temperature greater than about 25° C.

Embodiment A47. The method of Embodiment A46 wherein reagent (1), reagent (2), reagent (3) and at least one reducing agent are contacted with the suitable solvent at a temperature greater than about 55° C.

Embodiment A48. The method of Embodiment A47 wherein reagent (1), reagent (2), reagent (3) and at least one reducing agent are contacted with the suitable solvent at a temperature greater than about 70° C.

Embodiment B1. The method described in the Summary of the Invention for preparing a compound of Formula 4 comprising contacting reagent (i) (i.e. a compound of Formula 5), reagent (ii) (i.e. a cycloalkadiene bidentate ligand), reagent (iii) (i.e. at least one metal reducing agent) and reagent (iv) (i.e. a nitrile solvent).

Embodiment B2. The method of Embodiment B1 wherein reagent (iii) comprises zinc or manganese.

Embodiment B3. The method of Embodiment B2 wherein the reagent (iii) comprises zinc.

Embodiment B4. The method of any one of Embodiments B1 through B3 wherein reagent (ii) comprises a conjugated or non-conjugated, optionally substituted 4- to 12-membered cycloalkadiene ring such as 1,5-cyclooctadiene, 1,3-cyclopentadiene, 1,4-cyclohexadiene, 2,3,5,6-tetramethyl-2,5-cyclohexadiene-1,4-dione (also known as duroquinone) and bicyclo[2.2.1]hepta-2,5-diene (also known as norbornadiene).

Embodiment B5. The method of Embodiment B4 wherein reagent (ii) is 1,5-cyclooctadiene (and therefore $R^9$ and $R^{10}$ together are 1,5-cyclooctadiene).

Embodiment B6. The method of any one of Embodiments B1 through B5 wherein Y is Cl.

Embodiment B6a. The method of any one of the Embodiments B1 through B6 wherein reagent (iv) comprises one or more solvents selected from the group consisting of acetonitrile, propionitrile and butyronitrile.

Embodiment B6b. The method of Embodiment B6b wherein reagent (iv) comprises acetonitrile.

Embodiment B7. The method of any one of Embodiments B1 through B6b wherein the mole ratio of reagent (ii) to reagent (i) is at least about 1.

Embodiment B8. The method of Embodiment B7 wherein the mole ratio of reagent (ii) to reagent (i) is at least about 3.

Embodiment B9. The method of any one of Embodiments B1 through B8 wherein the mole ratio of reagent (ii) to reagent (i) is not larger than about 10.

Embodiment B10. The method of Embodiment B9 wherein the mole ratio of reagent (ii) to reagent (i) is not larger than about 5.

Embodiment B11. The method of any one of Embodiments B1 through B10 wherein the equivalent ratio of reagent (iii) to reagent (i) is at least about 1

Embodiment B12. The method of Embodiment B11 wherein the equivalent ratio of reagent (iii) to reagent (i) is at least about 2.

Embodiment B13. The method of Embodiment B12 wherein the equivalent ratio of reagent (iii) to reagent (i) is at least about 5.

Embodiment B14. The method of any one of Embodiments B1 through B13 wherein the equivalent ratio of reagent (iii) to reagent (i) is not larger than about 20.

Embodiment B15. The method of Embodiment B14 wherein the equivalent ratio of reagent (iii) to reagent (i) is not larger than about 15.

Embodiment B16. The method of any one of Embodiments B1 through B15 wherein the reagent (i) and reagent (iv) are contacted to form a mixture, and then reagent (ii) and reagent (iii) are sequentially added to the mixture.

Embodiment B17. The method of any one of Embodiments B1 through B15 wherein the reagent (i), reagent (ii) and reagent (iv) are contacted to form a mixture, and then (iii) is added to the mixture.

Embodiment B18. The method of any one of Embodiments B1 through B17 wherein the reagent (i), reagent (ii), reagent (iii) and reagent (iv) are contacted at a temperature not greater than about 50° C.

Embodiment B19. The method of Embodiment B18 wherein the reagent (i), reagent (ii), reagent (iii) and reagent (iv) are contacted at a temperature not greater than about 45° C.

Embodiment B20. The method of any one of Embodiments B1 through B19 wherein the reagent (i), reagent (ii), reagent (iii) and reagent (iv) are contacted at a temperature greater than about 25° C.

Embodiment B21. The method of Embodiment B20 wherein the reagent (i), reagent (ii), reagent (iii) and reagent (iv) are contacted at a temperature greater than about 35° C.

Embodiment C1. The method described in the Summary of the Invention for preparing a compound of Formula 1 further comprising contacting reagent (a) (i.e. a compound of Formula 5) with reagent (b) (i.e. a cycloalkadiene bidentate ligand) and reagent (c) (i.e. at least one metal reducing agent) to form a mixture comprising a compound of Formula 4 wherein $R^9$ and $R^{10}$ together are a cycloalkadiene bidentate ligand; wherein the mixture comprising the compound of Formula 4 is contacted with reagent (1) (i.e. the compound of Formula 2) and reagent (2) (the at least one compound of Formula 3).

Embodiment C2. The method of Embodiment C1 wherein reagent (c) comprises zinc or manganese.

Embodiment C3. The method of Embodiment C2 wherein reagent (c) comprises zinc.

Embodiment C4. The method of any one of Embodiments C1 through C3 wherein reagent (b) comprises a conjugated or non-conjugated, optionally substituted 4- to 12-membered cycloalkadiene ring such as 1,5-cyclooctadiene, 1,3-cyclopentadiene, 1,4-cyclohexadiene, 2,3,5,6-tetramethyl-2,5-cyclohexadiene-1,4-dione (also known as duroquinone) and bicyclo[2.2.1]hepta-2,5-diene (also known as norbornadiene).

Embodiment C5. The method of Embodiment C4 wherein reagent (b) is 1,5-cyclooctadiene (and therefore $R^9$ and $R^{10}$ together are 1,5-cyclooctadiene).

Embodiment C6. The method of any one of Embodiments C1 through C5 wherein Y is Cl.

Embodiment C7. The method of any one of Embodiments C1 through C6 wherein the mole ratio of reagent (b) to reagent (a) is at least about 1.

Embodiment C8. The method of Embodiment C7 wherein the mole ratio of reagent (b) to reagent (a) is at least about 2.

Embodiment C9. The method of any one of Embodiments C1 through C8 wherein the mole ratio of reagent (b) to the reagent (a) is not larger than about 10.

Embodiment C10. The method of Embodiment C9 wherein the mole ratio of reagent (b) to reagent (a) is not larger than about 3.

Embodiment C11. The method of any one of Embodiments C1 through C10 wherein the equivalent ratio of reagent (c) to the reagent (a) is at least about 5.

Embodiment C12. The method of Embodiment C11 wherein the equivalent ratio of reagent (c) to the reagent (a) is at least about 10.

Embodiment C13. The method of Embodiment C12 wherein the equivalent ratio of reagent (c) to the reagent (a) is at least about 15.

Embodiment C14. The method of Embodiment C13 wherein the equivalent ratio of reagent (c) to the reagent (a) is at least about 20.

Embodiment C15. The method of any one of Embodiments C1 through C14 wherein the equivalent ratio of reagent (c) to the reagent (a) is not larger than about 50.

Embodiment C16. The method of Embodiment C15 wherein the equivalent ratio of reagent (c) to the reagent (a) is not larger than about 30.

Embodiment C17. The method of Embodiment C16 wherein the equivalent ratio of reagent (c) to the reagent (a) is not larger than about 25.

Embodiment C18. The method of any one of Embodiments C1 through C17 wherein the mole percentage of the compound of Formula 4 to reagent (a) is at least about 0.1%.

Embodiment C19. The method of Embodiment C18 wherein the mole percentage of the compound of Formula 4 to reagent (a) is at least about 0.5%.

Embodiment C20. The method of Embodiment C19 wherein the mole percentage of the compound of Formula 4 to reagent (a) is at least about 0.75%.

Embodiment C21. The method of Embodiment C20 wherein the mole percentage of the compound of Formula 4 to reagent (a) is at least about 1%.

Embodiment C22. The method of any one of Embodiments C1 through C22 wherein the mole percentage of the compound of Formula 4 to reagent (a) is not larger than about 5%.

Embodiment C23. The method of Embodiment C22 wherein the mole percentage of the compound of Formula 4 to reagent (a) is not larger than about 3%.

Embodiment C24. The method of Embodiment C23 wherein the mole percentage of the compound of Formula 4 to reagent (a) is not larger than about 1.5%.

Embodiment C25. The method of any one of Embodiments C1 through C24 wherein the mole ratio of reagent (2) to reagent (1) is at least about 1.

Embodiment C26. The method of Embodiment C25 wherein the mole ratio of reagent (2) to reagent (1) is at least about 1.5.

Embodiment C27. The method of any one of Embodiments C1 through C26 wherein the mole ratio of reagent (2) to reagent (1) is not larger than about 5.

Embodiment C28. The method of Embodiment C27 wherein the mole ratio of the reagent (2) to reagent (1) is not larger than about 2.

Embodiment C29. The method of any one of Embodiments C1 through C28 wherein reagent (a), reagent (b), and reagent (c) are contacted in the presence of a suitable solvent to form a mixture, and then reagent (1) and reagent (2) are added to the mixture.

Embodiment C30. The method of Embodiment C29 wherein the suitable solvent comprises one or more solvents selected from the group consisting of nitriles (e.g., acetonitrile, propionitrile, butyronitrile), ethers (e.g., tetrahydrofuran) and halogenated and nonhalogenated aromatic hydrocarbons (e.g., xylenes, toluene, chlorobenzene, dichlorobenzene).

Embodiment C31. The method of Embodiment C30 wherein the suitable solvent comprises one or more solvents selected from the group consisting of nitriles (e.g., acetonitrile, propionitrile, butyronitrile).

Embodiment C32. The method of Embodiment C31 wherein the suitable solvent comprises acetonitrile.

Embodiment C33. The method of any one of Embodiments C29 through C32 wherein reagent (a), reagent (b), and reagent (c) are contacted with the suitable solvent to form a mixture, and then reagent (1) and reagent (2) are added to the mixture at a temperature not greater than about 100° C.

Embodiment C34. The method of Embodiment C33 wherein reagent (a), reagent (b), and reagent (c) are contacted with the suitable solvent to form a mixture, and then reagent (1) and reagent (2) are added to the mixture at a temperature not greater than about 50° C.

Embodiment C36. The method of any one of Embodiments C29 through C34 wherein reagent (a), reagent (b), and reagent (c) are contacted with the suitable solvent to form a mixture, and then reagent (1) and reagent (2) are added to the mixture at a temperature greater than about 20° C.

Embodiment C37. The method of Embodiment C36 wherein reagent (a), reagent (b), and reagent (c) are contacted with the suitable solvent to form a mixture, and then reagent (1) and reagent (2) are added to the mixture at a temperature greater than about 25° C.

Embodiment C38. The method of Embodiment C37 wherein reagent (a), reagent (b), and reagent (c) are contacted with the suitable solvent to form a mixture, and then reagent (1) and reagent (2) are added to the mixture at a temperature greater than about 35° C.

Embodiment C39. The method of Embodiment C38 wherein reagent (a), reagent (b), and reagent (c) are contacted with the suitable solvent to form a mixture, and then reagent (1) and reagent (2) are added to the mixture at a temperature greater than about 40° C.

Embodiment C40. The method of any one of Embodiments C1 through C39 wherein the reaction mixture comprising the compound of Formula 4 is contacted with a Lewis base, and then reagent (1) and reagent (2).

Embodiment C41. The method of Embodiment C40 wherein the Lewis base comprises a primary, secondary or tertiary aliphatic amine.

Embodiment C42. The method of Embodiment C41 wherein the Lewis base comprises triethylamine.

Embodiment D1. A method described in the Summary of the Invention for preparing a compound of Formula 6 using a compound of Formula 1 prepared from the compound of Formula 2.

Embodiment D2. The method of Embodiment D1 wherein Z is N.

Embodiment D3. The method of Embodiment D1 wherein Z is CH.

Embodiment D4. The method of any one of Embodiments D1 through D3 wherein $R^2$ is $CH_3$.

Embodiment D5. The method of any one of Embodiments D1 through D4 wherein $R^3$ is $C_1$-$C_4$ alkyl, cyclopropyl, cyclopropylcyclopropyl, cyclopropylmethyl or methylcyclopropyl.

Embodiment D6. The method of Embodiment D5 wherein $R^3$ is $C_1$-$C_4$ alkyl or cyclopropylmethyl.

Embodiment D7. The method of Embodiment D6 wherein $R^3$ is methyl.

Embodiment D8. The method of any one of Embodiments D1 through D7 wherein $R^2$ is methyl.

Embodiment D9. The method of any one of Embodiments D1 through D8 wherein $R^{15}$ is Br.

Embodiment D10. The method of any one of Embodiments D1 through D9 wherein $R^{16}$ is Cl.

Embodiment D11. The method of any one of Embodiments D1 through D10 wherein $R^{17}$ is H.

Embodiment E1. The method of any one of Embodiments A1 through A48, B1 through B21, and C1 through C42 wherein $R^5$ is a phenyl ring optionally substituted with up to 3 substituents independently selected from $R^{11}$.

Embodiment E2. The method of any one of Embodiments A1 through A48, B1 through B21, C1 through C42, and E1 wherein $R^6$ is a phenyl ring optionally substituted with up 3 substituents independently selected from $R^{12}$.

Embodiment E3. The method of any one of Embodiments A1 through A48, B1 through B21, C1 through C42, and E1 through E2 wherein $R^7$ is a phenyl ring optionally substituted with up 3 substituents independently selected from $R^{13}$.

Embodiment E4. The method of any one of Embodiments A1 through A48, B1 through B21, C1 through C42, and E1 through E3 wherein $R^8$ is a phenyl ring optionally substituted with up 3 substituents independently selected from $R^{14}$.

Embodiment E5. The method of any one of Embodiments E1 through E4 wherein each $R^{11}$, $R^{12}$, $R^{13}$ and $R^{14}$ is independently fluorine, $C_1$-$C_4$ alkyl, $C_1$-$C_4$ fluoroalkyl or $C_1$-$C_4$ alkoxy.

Embodiment E6. The method of Embodiment E5 wherein each $R^{11}$, $R^{12}$, $R^{13}$ and $R^{14}$ is independently $C_1$-$C_4$ alkyl.

Embodiment E7. The method of any one of Embodiments A1 through A48, B1 through B21, C1 through C42, and E1 through E6 wherein each $R^5$, $R^6$, $R^7$, $R^8$ is an unsubstituted phenyl ring.

Embodiment E8. The method of any one of Embodiments A1 through A48, B1 through B21, C1 through C42, and E1 through E7 wherein $R^9$ and $R^{10}$ together are 1,5-cyclooctadiene (bonded to the nickel atom through both alkene bonds).

Embodiment E9. The method of any one of Embodiments A1 through A48, B1 through B21, C1 through C42, and E1 through E8 wherein the compound of Formula 4 comprises [1,1'-bis(diphenylphosphino)ferrocene)][(1,2,5,6)-1,5-cyclooctadiene]nickel.

Embodiments of this invention can be combined in any manner.

In the following Schemes 1-13 the definitions of $R^1$, $R^2$, $R^3$, $R^4$, $R^5$, $R^6$, $R^7$, $R^8$, $R^9$, $R^{10}$, $R^{15}$, $R^{16}$, $R^{17}$, X, Y and Z in the compounds of Formulae 1 through 17 are as defined above in the Summary of the Invention and description of Embodiments unless otherwise indicated. Formulae 1a, 1b and 1c are subsets of Formula 1. Formula 2a is a subset of Formula 2.

As shown in Scheme 1, in a method of the present invention a compound of Formula 1 is prepared by contacting a compound of Formula 2 with at least one compound of Formula 3 and a compound of Formula 4.

Scheme 1

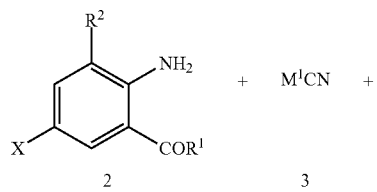

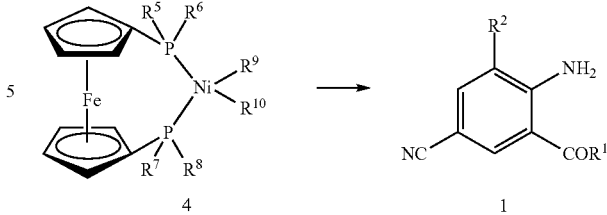

In the method of Scheme 1, compounds of Formula 3 comprise $M^1$ which can be K, Na, Cs or Rb, more preferably K or Na, and most preferably Na. Typically the molar ratio of the compound or compounds of Formula 3 to the compound of Formula 2 is from about 1 to about 5, and more typically from about 1 to about 2. Although higher levels of Formula 3 compounds can be used there is no particular advantage in doing so and higher levels increase raw material and waste processing costs, thus the optimum molar ratio is between about 1 and about 1.5. When using alkali metal cyanides such as Formula 3 compounds reducing the particle size of the alkali metal cyanides prior to use can facilitate optimal yields of Formula 1 compounds. Grinding or milling alkali metal cyanides before use can provide smaller particle size material. Alternatively, the method of Scheme 1 can be run using a mixing apparatus that reduces solids to smaller size particles through cutting and blending, for example a high-speed, high-shear mixer such as a homogenizer.

Compounds of Formula 4 act as a source of a chemical species which catalyzes the conversion of compounds of Formula 2 to compounds of Formula 1. The substituents $R^9$ and $R^{10}$ in Formula 4 are each independently a displaceable ligand or together are a bidentate, displaceable ligand. A wide variety of ligands are useful in the present method, as the only requirements are: (1) the ligand has at least one pair of electrons, or in the case of a bidentate ligand at least two pairs of electrons, available for coordination with the nickel atom in a compound of Formula 4, and (2) be capable of being displaced during the reaction, thus generating the active catalytic species. Suitable ligands include, for example, $C_1$-$C_4$ alkyl, $C_3$-$C_6$ alkenyl, 5 to 6-membered carbocycles and 5 to 6-membered heterocycles. When $R^9$ and $R^{10}$ together are a bidentate, displaceable ligand, suitable ligands include, for example, cycloalkadienes. Preferred ligands are cycloalkadienes, which are conjugated or non-conjugated, optionally substituted and have 4- to 12-carbon atoms in the ring such as 1,5-cyclooctadiene, 1,3-cyclopentadiene, 1,4-cyclohexadiene, 2,3,5,6-tetramethyl-2,5-cyclohexadiene-1,4-dione (also known as duroquinone) and bicyclo[2.2.1]hepta-2,5-diene (also known as norbornadiene). Especially preferred is 1,5-cyclooctadiene. Formula 4 further comprises substituents $R^5$ and $R^7$ which are each independently an optionally substituted phenyl ring, and substituents $R^6$ and $R^8$ which are each independently an optionally substituted phenyl ring or a naphthalenyl ring system. Each ring or ring system is optionally substituted with groups independently selected from those disclosed in the Summary of the Invention. Compounds of Formula 4 useful in the method of Scheme 1 include various combinations of $R^5$, $R^6$, $R^7$ and $R^8$ substituent groups. For example, a compound of Formula 4 wherein $R^5$, $R^6$, $R^7$ and $R^8$ are all unsubstituted phenyl (i.e. the ferrocene-containing ligand is 1,1'-bis(diphenylphosphino)ferrocene) is especially useful. Other examples of ferrocene-containing ligands in compounds of Formula 4 include the following: 1,1'-bis[bis[2-(1-methylethyl)phenyl]phosphino]ferrocene, 1,1'-bis[bis(2-methoxyphenyl)phosphino]ferrocene and 1-[bis(4-methoxyphenyl)phosphino]-1'-[bis[4-(trifluoromethyl)phenyl]phosphino]ferrocene. Preferred as a ligand in a compound of Formula 4 in the present method is 1,1'-bis(diphenylphosphino)ferrocene. An especially preferred compound of Formula 4 is [1,1'-bis(diphenylphosphino)ferrocene)][(1,2,5,6)-1,5-cyclooctadiene]nickel (i.e. each $R^5$, $R^6$, $R^7$ and $R^8$ is a phenyl ring, and $R^9$ and $R^{10}$ together are 1,5-cyclooctadiene). The molar percentage of the compound of Formula 4 relative to the compound of Formula 2 is typically from about 0.1% to about 5%. Molar percentages greater than 0.1% can often accelerate the reaction while percentages above 5% generally offer little additional benefit while increasing cost. The ratio is preferably from about 1% to about 1.5% to provide convenient reaction rates while limiting cost.

The method of Scheme 1 typically achieves the highest product yield when the reaction is run in the presence of at least one reducing agent. Although the product of Formula 1 forms in the absence of a reducing agent, the yield may be lower compared to the reaction run in the presence of a reducing agent. The reducing agent is preferably a metal reducing agent such as, for example, zinc or manganese, or a silane reducing agent such as polymethylhydrosiloxane. If elemental zinc is used as the reducing agent the equivalent percentage is preferably from about 10% to about 100% relative to the compound of Formula 2, and more typically from about 40% to about 80%. The optimum amount of zinc can vary depending on the particle size (although typically still within the 10 to 100% range described above). In some cases it may be beneficial to reduce the particle size of the zinc prior to use by standard means, such as grinding or milling. If polymethylhydrosiloxane is used as the reducing agent the highest product yield is typically obtained when the reaction is conducted in the presence of a small amount of at least one metal reducing agent (e.g., zinc) in addition to the polymethylhydrosiloxane. In the method of Scheme 1 when polymethylhydrosiloxane is used in combination with zinc the equivalent percentage of polymethylhydrosiloxane is preferably from about 1% to about 80% relative to the compound of Formula 2, and more preferably about 10% to about 60%; and the equivalent percentage of zinc is preferably from about 0.02% to about 0.6% (of note about 0.01% to about 0.3%) relative to the compound of Formula 2. Higher levels of zinc can be used in combination with polymethylhydrosiloxane, but there is no particular advantage in doing so is generally not advantageous.

The reaction of Scheme 1 is typically conducted in a suitable solvent. A variety of solvents can be used to form the suitable solvent for this method. Typically, the method is most satisfactorily conducted using solvents in which the compound of Formula 2 is preferably completely or at least substantially soluble and the compounds of Formulae 3 and 4 typically have low solubility at ambient temperatures (e.g., about 15-40° C.) in the volume of solvent used. Examples of suitable solvents include nitriles, such as acetonitrile, propionitrile and butyronitrile, ethers such as tetrahydrofuran, and halogenated and nonhalogenated aromatic hydrocarbons such as xylenes, toluene, chlorobenzene, and mixtures thereof. The reaction of the present method works particularly well in nitrile solvents, such as, but not limited to, acetonitrile or propionitrile. Acetonitrile gives excellent results and is most preferred. The total volume of the solvent used in the method of Scheme 1 is preferably between about 4 mL/g and about 20 mL/g relative to the weight of the compound of Formula 2, and more preferably between about 4 mL/g and about 8 mL/g.

The method of Scheme 1 is preferably conducted using oxygen-free solvents, because oxygen dissolved in the solvent can cause compounds of Formula 4 to oxidize. Standard techniques can be used to obtain oxygen-free solvents including, for example, refluxing/distilling the solvents in an inert atmosphere (e.g., nitrogen or argon) (optionally in the presence of a drying agent, such as calcium hydride or phosphorus pentoxide), sparging the solvents with an inert gas (e.g., nitrogen or argon) or by freezing the solvents (using liquid nitrogen), applying a vacuum and then allowing the solvents to warm to room temperature. Additionally, the method of Scheme 1 is preferably conducted in an oxygen-free environment. Reducing the presence of atmospheric oxygen during the transfer of the reagents to the reaction vessel is particularly advantageous. This can be achieved using well known techniques including, for example, transferring the reagents to the reaction vessel in an inert atmosphere using a glove box or Schlenk techniques.

When combining the reagents it is particularly advantageous to avoid contacting the compounds of Formulae 2 and 4 for any appreciable amount of time in the absence of the compound or compounds of Formula 3. If a reducing agent is used in the method of Scheme 1 it is especially advantageous to avoid contacting the compound Formula 2, the compound of Formula 4 and the reducing agent in the absence of the compound or compounds of Formula 3. Otherwise, the reagents can be combined in a variety of orders, such as combining the compounds of Formulae 2 and 3 with the suitable solvent to form a mixture, and then adding the compound of Formula 4 to the mixture. The most preferred order of addition for preparing a compound of Formula 1 has been found to comprise combining the compounds of Formulae 2, 3 and 4, and then adding the suitable solvent to form a mixture. When using a reducing agent, the preferred order typically comprises combining the compounds of Formulae 2, 3, 4 and the reducing agent, and then adding the suitable solvent to form a mixture.

The present method is typically conducted at a temperature between about 25 and 100° C. and more typically between about 25 and 85° C. Often the most favorable reaction rates, providing the highest product yield and purity of compounds of Formula 1, are obtained when the components are contacted at reaction temperatures ranging between about 70 and 85° C. To achieve reaction of the components in this temperature range, the components can be combined at about ambient temperature (e.g., about 15-40° C.) and then the temperature can be raised to between about 70 and 85° C. The reaction can conducted using a solvent with a normal boiling point within or above this range or the reaction can be conducted at elevated pressure with a lower boiling solvent. The reaction time can vary, but is usually no more than about 3 h.

The product of Formula 1 can be isolated by standard techniques known in the art, including filtration, extraction, evaporation and crystallization. As the compounds of Formula 1 are typically solids at ambient temperature, they are most easily isolated by filtration, optionally preceded by concentrating the reaction mixture and optionally followed by washing with water and/or an organic solvent (e.g., acetonitrile). Additionally, product can be isolated by concentrating the filtrate under reduced pressure, slurrying the resulting residue in a suitable solvent (e.g., acetonitrile), filtering and optionally washing with water and/or a solvent (e.g., acetonitrile). The product can be further purified by recrystallization from an appropriate organic solvent (e.g., ethanol, methanol, acetonitrile).

The features of the present method provide an efficient means to produce compounds of Formula 1 in typically high yields (often 98%), in about 1 to about 3 h. Of particular note is that the present method can be used to provide remarkably high yields of the compounds of Formula 1 in excellent purity even though these compounds as well as the starting compounds of Formula 2 contain amino substituents and in some cases amide substituents that can potentially participate in side reactions. Also, as compared to previously known cyanation processes, the present process provides a method for cyanation of 5-halobenzoic acids and derivatives while avoiding deactivation of the nickel catalyst (through the formation of inactive nickel cyanide complexes) without involving complex and/or additional operations or reagents. The method of Scheme 1 is illustrated in Examples 2-4 below.

Starting compounds of Formula 2 can be made by a number of methods known in the art. As shown in Scheme 2, according to one method compounds of Formula 2 can be prepared by halogenation of a compound of Formula 7 using a variety of reagents such as bromine, chlorine, iodine, sulfuryl chloride, N-chlorosuccinimide (NCS), N-bromosuccinimide (NBS), N-iodosuccinimide (NIS), and halogenating agents such as mixtures comprising hydrogen peroxide and a hydrogen halide. For leading references describing this method, see PCT Patent Publications WO 2006/068669 (Scheme 11 and Example 1, Step E), WO 2003/015519 (Scheme 4 and Example 1, Step A), WO 2006/062978 (Scheme 15; Example 2, Step A; Example 4, Step B and Example 5, Step B), and WO 2004/067528 (Scheme 11 and Example 1, Step A).

Scheme 2

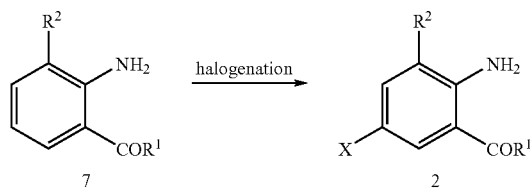

Another method for preparing compounds of Formula 2 (wherein X is Br and $R^1$ is $NHR^3$) involves bromination of compounds of Formula 7 by treatment with a gas containing bromine, as illustrated by the procedure of Reference Example 1.

Compounds of Formula 2 (wherein $R^1$ is $NHR^3$) can also be prepared by contacting an isatoic anhydride of Formula 8 with an alkyl amine of Formula 9 in the presence of a carboxylic acid as illustrated in Scheme 3.

Scheme 3

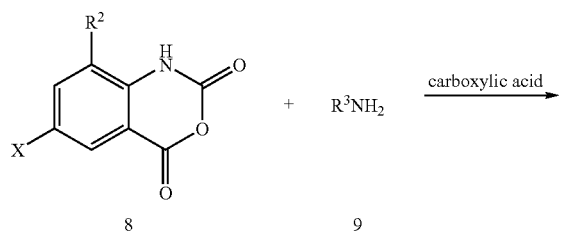

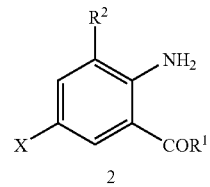

wherein $R^1$ is $NHR^3$

As amines such as the compound of Formula 9 are bases, in the absence of the carboxylic acid, the mixture of the compounds of Formulae 8 and 9 would be basic (i.e. effective pH>7). The carboxylic acid acts as a buffer to reduce the effective pH of the reaction mixture. A wide variety of carboxylic acids are useful, as the only requirement is for at least one carboxylic acid group to impart acidity. Other functional groups can be present, and more than one carboxylic acid group can be present on the carboxylic acid molecule. Typically the carboxylic acid has an effective $pK_a$ in the range of about 2 to about 5. Carboxylic acids include, for example, formic acid, acetic acid, propionic acid, chloroacetic acid, benzoic acid, phthalic acid, maleic acid, tartaric acid and citric acid. For reason of cost, inexpensive carboxylic acids such as formic acid, acetic acid, propionic acid and benzoic acid are preferred. Acetic acid, which is commercially available at low cost in its anhydrous form (known as "glacial acetic acid") is particularly preferred.

The combination of the carboxylic acid with the basic amine of Formula 9 forms an amine salt of the carboxylic acid. This amine salt can be preformed before addition of the isatoic anhydride compound of Formula 8, or the amine salt can be generated in situ by metering the amine of Formula 9 into a mixture of the compound of Formula 8 and the carboxylic acid. For either mode of addition, maintaining the effective pH of the mixture during the reaction between about 3 and about 7 is generally optimal.

As the effective pH of the mixture results from the buffering effect of the carboxylic acid in combination with the amine of Formula 9, the effective pH can be adjusted according to the effective $pK_a$ of the carboxylic acid by adjusting the molar ratio of carboxylic acid to the amine of Formula 9. Typically the molar ratio of the amine of Formula 9 to carboxylic acid is in the range from about 0.8 to about 3. More particularly, when the mode of combination involves metering the amine of Formula 9 into a mixture of the isatoic anhydride compound of Formula 8 and carboxylic acid, the molar ratio of Formula 9 amine to carboxylic acid is preferably from about 0.95 to about 3. When the mode of combination involves forming the amine salt before addition of the compound of Formula 8 the molar ratio of Formula 9 amine to carboxylic acid is preferably from about 0.8 to about 1.05; as long as a nearly equimolar ratio (e.g., about 0.95 to about 1.05) of Formula 9 amine to carboxylic acid is used, the amine salt thus formed is typically used in a ratio of about 1.1 to about 5 molar equivalents relative to the compound of Formula 8. For optimal conversions, the molar ratio of amine of Formula 9 to isatoic anhydride compound of Formula 8 should be at least 1.0, although the molar ratio is preferred to be from about 1.1 to about 1.5 for reasons of efficiency and of economy, regardless of how the components are mixed. The molar amount of amine of Formula 9 relative to compound of Formula 8 can be substantially greater than 1.5, particularly when a nearly equimolar ratio (e.g., about 0.95 to about 1.05) of amine to acid is used.

Highest product yield and purity is achieved when the reaction medium is substantially anhydrous. The reaction medium is thus typically formed from substantially anhydrous compounds of Formulae 8 and 9 and carboxylic acid. Preferably the reaction medium and forming materials contain about 5% or less, more preferably about 1% or less, and most preferably about 0.1% water or less (by weight). If the carboxylic acid is acetic acid, it is preferably in the form of glacial acetic acid.

The reaction of Scheme 3 is typically conducted in a liquid phase. In many cases the reaction can be carried out without solvent other than the compounds of Formulae 2, 8 and 9 and the carboxylic acid. But a preferred procedure involves use of a solvent that can suspend and at least partially dissolve the reactants. Preferred solvents are those which are non-reactive with the reaction components and have a dielectric constant of about 5 or greater, such as alkyl nitriles, esters, ethers, or ketones. Preferably the solvent should be substantially anhydrous to facilitate achieving a substantially anhydrous reaction medium. The weight ratio of solvent to the compound of Formula 8 is typically from about 1 to about 20, and preferably about 5 for reasons of efficiency and economy.

Carbon dioxide forms as a byproduct of the reaction of Scheme 3. Most of the carbon dioxide formed evolves from the reaction medium as a gas. The addition of the compound of Formula 8 into reaction medium containing the amine of Formula 9 or the addition of the amine of Formula 9 into the reaction medium containing the compound of Formula 8 is preferably conducted at such a rate and temperature as to facilitate controlling the evolution of carbon dioxide. The temperature of the reaction medium is typically between about 5 and 75° C., more typically between about 35 and 55° C.

The product of Formula 2 can be isolated by standard techniques known in the art, including pH adjustment, extraction, evaporation, crystallization and chromatography. For example, the reaction medium can be diluted with about 3 to 15 parts by weight of water relative to the starting compound of Formula 9, the pH can be optionally adjusted with either acid or base to optimize the removal of either acidic or basic impurities, the water phase can be optionally separated, and most of the organic solvent can be removed by distillation or evaporation at reduced pressure. As the compounds of Formula 2 are typically crystalline solids at ambient temperature, they are generally most easily isolated by filtration, optionally followed by washing with water and then drying.

As shown in Scheme 4, isatoic anhydrides of Formula 8 can be prepared from anthranilic acids of Formula 2a (Formula 2 wherein $R^1$ is $OR^4$ and $R^4$ is H) via a cyclization reaction involving treatment of the anthranilic acids with phosgene or a phosgene equivalent such as triphosgene or an alkyl chloroformate (e.g., methyl chloroformate) in a suitable solvent such as toluene or tetrahydrofuran. The method is described in PCT Patent Publication WO 2006/068669, including a specific example relevant to Scheme 4. Also see Coppola, *Synthesis* 1980, 505 and Fabis et al., *Tetrahedron* 1998, 10789.

Compounds of Formula 2a are commercially available and can be prepared by the method of Scheme 2 and other methods well documented in the chemistry art.

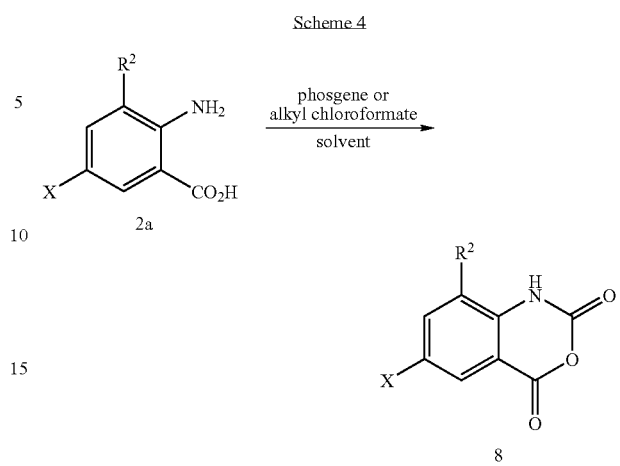

Phosphinoferrocene compounds of Formula 4 can be prepared by a number of methods known in the art. As illustrated in Scheme 5, in one method compounds of Formula 4 (wherein each $R^9$ and $R^{10}$ is independently a displaceable ligand) can be prepared by the first step reacting a phosphinoferrocene derivative of Formula 10, with a nickel dihalide of Formula 11, a compound of Formula 12 and a metal reducing agent (e.g., zinc). The resulting nickel complex of Formula 13 can subsequently be treated with an organolithium reagent such as methyllithium, n-butyllithium or sec-butyllithium to provide a compound of Formula 4. Conditions for the first step involve combining the phosphinoferrocene derivative of Formula 10, the nickel dihalide of Formula 11 and the compound of Formula 12 in a suitable solvent, and then adding the metal reducing agent. Suitable solvents include, for example, aromatic hydrocarbons (e.g., toluene, xylenes), or mixtures of an aromatic hydrocarbon and an alcohol (e.g., toluene and ethanol). The reaction is conducted at about ambient temperature (e.g., about 15-20° C.) to 60° C. The second step, reaction of the compound of Formula 13 with an organolithium reagent, is conducted in an organic solvent such as tetrahydrofuran or diethyl ether at a temperature between about −20° C. and ambient temperature. General procedures for the method of Scheme 5 are described in European Patent EP 314327-B1 and European Patent Application Publication EP 613719-A.

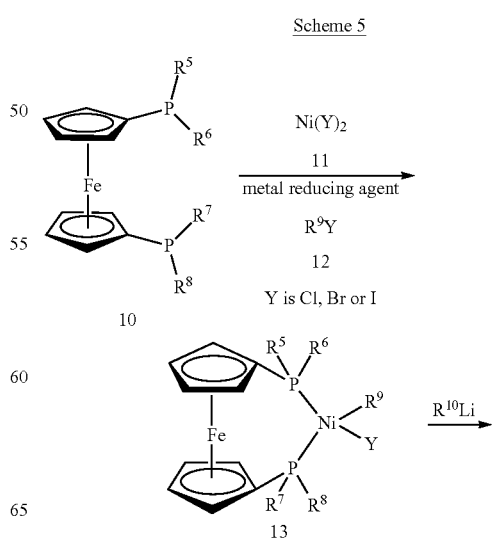

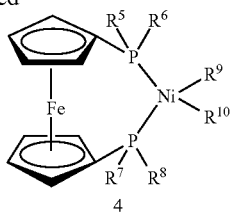

wherein each $R^9$ and $R^{10}$ is independently a displaceable ligand

Scheme 6 illustrates another method for preparing phosphinoferrocene compounds of Formula 4 (wherein $R^9$ and $R^{10}$ are each the same displaceable ligand). In this method a phosphinoferrocene nickel dihalide of Formula 5 is reacted with 2 equivalents of an organolithium reagent (RLi), such as methyllithium, n-butyllithium or sec-butyllithium, or a Grignard reagent ($RMgX^1$), such as ethyl or phenyl magnesium bromide. $R^9$ and $R^{10}$ in the Formula 4 product are the same as R in the RLi or $RMgX^1$ reagent. The reaction is typically conducted in a suitable solvent such as diethyl ether or tetrahydrofuran, at a temperature between about −20° C. and ambient temperature (e.g., about 15-20° C.). The general procedure for the method of Scheme 6 is described in European Patent EP 314327-B1 and European Patent Application Publication EP 613719-A.

Scheme 6

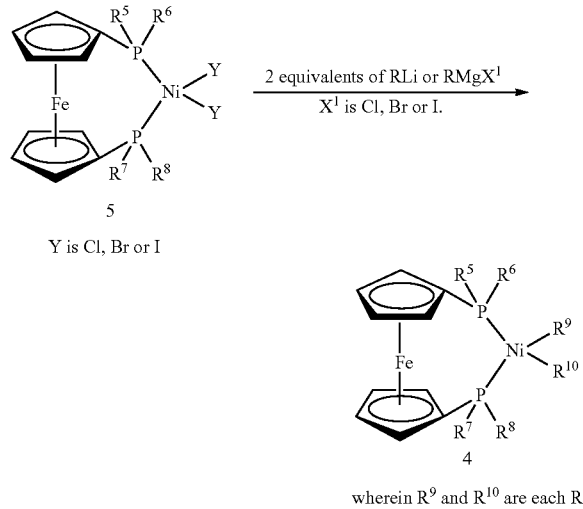

wherein $R^9$ and $R^{10}$ are each R

Compounds of Formula 5 are commercially available and can be readily prepared from commercially available starting materials, such as nickel dihalides (e.g., $NiCl_2$, $NiBr_2$, $NiI_2$; either hydrated or anhydrous forms can be used) and 1,1'-bis(diarylphosphino)ferrocenes (e.g., 1,1'-bis(diphenylphosphino)ferrocene) by methods reported in the literature; for example, see A. W. Rudie et al., *Inorganic Chemistry* 1978, 17(10), 2859-2863; B. Corain et al., *Inorganica Chimica Acta* 1989, 157, 259-266; and G. J. Grant et al., *Journal of Organometallic Chemistry* 2001, 637-639, 683-690.

In another aspect of the present invention a compound of Formula 4 (wherein $R^9$ and $R^{10}$ together are a bidentate, displaceable ligand) can be prepared by contacting a phosphinoferrocene nickel dihalide of Formula 5, a cycloalkadiene bidentate ligand, at least one metal reducing agent and nitrile solvent as shown in Scheme 7.

Scheme 7

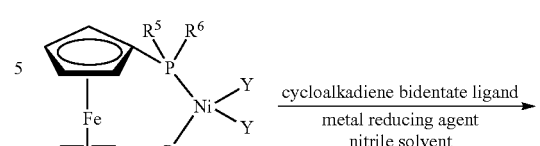

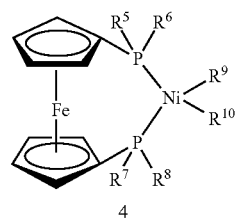

wherein $R^9$ and $R^{10}$ together are a bidentate, displaceable ligand

In the method of Scheme 7, phosphinoferrocene nickel dihalides of Formula 5 comprise the substituents $R^5$ and $R^7$, which as disclosed above in the Summary of the Invention, are each independently an optionally substituted phenyl ring. Formula 5 further comprises the substituents $R^6$ and $R^8$, which as disclosed above in the Summary of the Invention, are each independently an optionally substituted phenyl ring or a naphthalenyl ring system. Each ring or ring system is optionally substituted with groups independently selected from those listed in the Summary of the Invention. Compounds of Formula 5 useful in the method of Scheme 7 include various combinations of $R^5$, $R^6$, $R^7$ and $R^8$ substituent groups. For example, a compound of Formula 5 wherein $R^5$, $R^6$, $R^7$ and $R^8$ are all unsubstituted phenyl (i.e. the ferrocene-containing ligand is 1,1'-bis(diphenylphosphino)ferrocene) is especially useful. Other examples of ferrocene-containing ligands in compounds of Formula 5 include the following: 1,1'-bis[bis[2-(1-methylethyl)phenyl]phosphino]ferrocene, 1,1'-bis[bis(2-methoxyphenyl)phosphino]ferrocene and 1-[bis(4-methoxyphenyl)phosphino]-1'-[bis[4-(trifluoromethyl)phenyl]phosphino]ferrocene. A preferred compound of Formula 5 for use in the present method is [1,1'-bis-(diphenylphosphino)ferrocene]dichloronickel (i.e. each $R^5$, $R^6$, $R^7$ and $R^8$ is a phenyl ring), which is commercial available.

A wide variety of cycloalkadiene ligands are useful in the present method, as the only requirement is the ligand comprise at least two pairs of electrons available for coordination with the nickel atom in a compound of Formula 5. Preferred are cycloalkadienes, which are conjugated or non-conjugated, optionally substituted and have 4- to 12-carbon atoms in the ring such as 1,5-cyclooctadiene, 1,3-cyclopentadiene, 1,4-cyclohexadiene, 2,3,5,6-tetra-methyl-2,5-cyclohexadiene-1,4-dione (also known as duroquinone) and bicyclo[2.2.1]hepta-2,5-diene (also known as norbornadiene). Especially preferred is 1,5-cyclooctadiene. The molar ratio of the cycloalkadiene ligand to the compound of Formula 5 is typically from about 1 to about 10, and preferably from about 3 to about 5.

Metal reducing agents suitable for the present method include, for example, zinc or manganese. Zinc metal has been found to be particularly useful in the present method. To provide greatest surface area, zinc metal in the reaction medium is typically in the form of a powder or dust (e.g., particle diameter <100 μm or <10 μm). The zinc metal can be activated by treatment with aqueous acid to remove oxide coating on the zinc metal particles before adding to the reaction medium. However, zinc metal powder or dust can also be used without prior activation. Typically the equivalent ratio of the metal reducing agent to the compound of Formula 5 is from about 1 to about 20. When using zinc as the metal reducing agent the equivalent ratio is preferably about 15 to about 20. If activated zinc dust is used the equivalent ratio is preferably from about 1 to about 5, and most preferably from about 1 to about 2.

The method of Scheme 7 is carried out in nitrile solvents in which the compound of Formula 5 typically has low solubility and the cycloalkadiene is completely or at least substantially soluble. Solvents comprising acetonitrile or propionitrile work particularly well. Acetonitrile gives excellent results and is preferred for reasons including cost. As the compound of Formula 4 may react with atmospheric oxygen present in the reaction solvent, typically oxygen-free solvents are used. Techniques for obtaining oxygen-free solvents include those already discussed for the method of Scheme 1.

In the method of Scheme 7 the preferred order of combination has been found to comprise combining the compound of Formula 5, the cycloalkadiene, at least one metal reducing agent and nitrile solvent. Other orders of addition are acceptable for the present method; however the combination of the compound of Formula 5, the metal reducing agent and the nitrile solvent for an appreciable amount of time in the absence of the cycloalkadiene should be avoided, as this could lead to decomposition of the compound of Formula 5.

The method of Scheme 7 is typically conducted at or near ambient temperature (e.g., about 15-40° C.). The reaction time can vary depending on conditions, but is usually no more than about 24 h.

As the compounds of Formula 4 are typically crystalline solid at ambient temperature, they are most conveniently isolated by filtration. For example, on cooling the reaction mixture the product can be collected by filtration. Optionally the solid can be washed with an organic solvent (e.g., acetonitrile) and dried. The method of Scheme 7 is illustrated by Example 1.

Alternatively, a compound of Formula 4 (wherein $R^9$ and $R^{10}$ together are a bidentate, displaceable ligand) can be prepared by contacting a phosphinoferrocene derivative of Formula 10, a nickel complex of Formula 14 (wherein $R^9$ and $R^{10}$ together are a bidentate, displaceable ligand) and a suitable solvent as shown in Scheme 8. The method is described in European Patent Application Publication EP 613719-A, including a specific example relevant to Scheme 8. Also, the method of Scheme 8 is illustrated by Reference Example 2 for $R^5$, $R^6$, $R^7$ and $R^8$ each being a phenyl ring, and $R^9$ and $R^{10}$ together being 1,5-cyclooctadiene.

Scheme 8

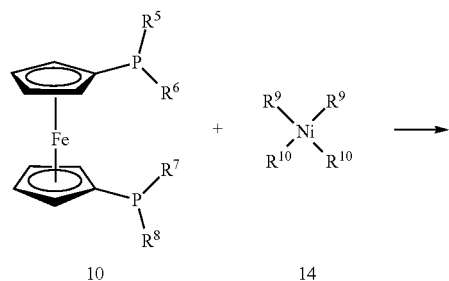

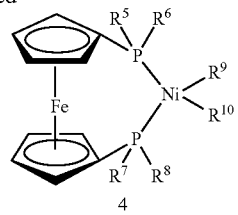

4 wherein $R^9$ and $R^{10}$ together are a bidentate, displaceable ligand

As shown in Scheme 9, according to another method of the present invention a compound of Formula 1 can be prepared by first preparing a compound of Formula 4 (wherein $R^9$ and $R^{10}$ together are a bidentate, displaceable ligand) by the method comprising contacting a compound of Formula 5 with a cycloalkadiene bidentate ligand and at least one metal reducing agent to form a mixture comprising a compound of Formula 4; and then contacting the mixture comprising the compound of Formula 4 with a compound of Formula 2 and at least one compound of Formula 3.

Scheme 9

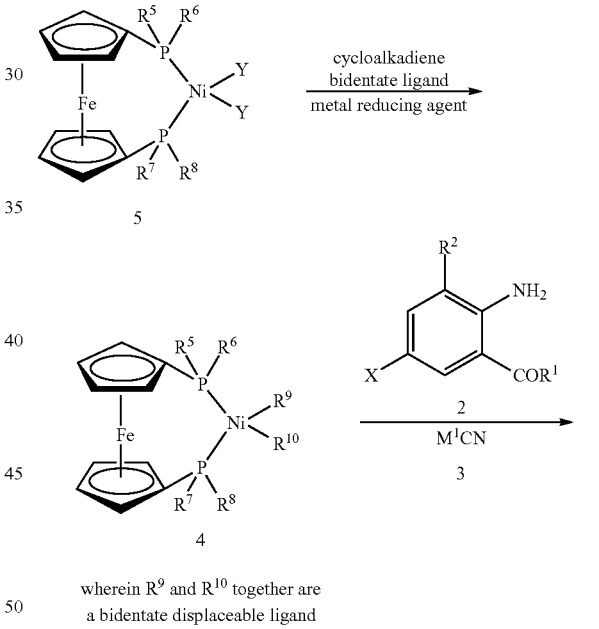

In the reaction sequence of Scheme 9 the two steps are conducted sequentially in the same reaction vessel and without isolation or purification of the products until the overall reaction sequence is complete. Both steps are conducted in a suitable solvent and typically the same solvent is used throughout the reaction sequence. A variety of solvents can be used to form the suitable solvent for this method. The method is most satisfactorily conducted using solvents in which the cycloalkadiene and the compound of Formula 2 are preferably completely or at least substantially soluble and the compounds of Formulae 5, 3 and 4 typically have low solubility at ordinary ambient temperatures (e.g., about 15 to 40° C.) in the volume of solvent used. Suitable solvents include nitriles, such as acetonitrile, propionitrile and butyronitrile, ethers such as tetrahydrofuran, and halogenated and nonhalogenated aromatic hydrocarbons such as xylenes, toluene and chlorobenzene, and mixtures thereof. More preferred solvents include acetonitrile or propionitrile. The reactions of Scheme 9 have been found to work particularly well (i.e. give excellent results) in acetonitrile. The total volume of the solvent used in the method of Scheme 9 is typically between about 150 mL/g and about 200 mL/g relative to the weight of the compound of Formula 5. The solvent can be added in one batch at the start of the reaction sequence or portionwise during the reaction sequence. For example, if so desired, a portion of the solvent can be added during the first step and a further portion can be added any time after completion of the first step (i.e. preparation of the compound of Formula 4). The method of Scheme 9 is preferably conducted using oxygen-free solvents. Techniques for obtaining oxygen-free solvents include those already discussed for the method of Scheme 1. The overall reaction sequence is typically conducted at temperatures ranging between about 20 and 100° C. Preferred for the first step, temperatures between about 20 and 30° C., and the second step are for temperatures from between about 80 and 100° C. Reaction periods for each step vary, but typically are in the range of about 2 to 4 h each.

In the first step compounds of Formula 4 are prepared by a method analogous to Scheme 7, except the suitable solvent is not limited to a nitrile solvent (as discussed in the preceding paragraph), and the amount of metal reducing agent added during the first step is typically sufficient for the subsequent cyanation step. Although the second step (i.e. cyanation step) does not require a metal reducing agent, highest yields of the Formula 1 compound are usually achieved when the reaction is conducted in the presence of at least one reducing agent (as discussed above regarding Scheme 1). When zinc is used as the metal reducing agent an initial equivalent ratio between about 5 and about 50 relative to the compound of Formula 5 is sufficient for both steps. Of note is an equivalent ratio between about 15 and about 25, and most of particular note is a ratio between about 20 and about 25.

The reagents in the first step may be combined in a variety of orders, except that contacting the compound of Formula 5, the metal reducing agent and the solvent in the absence of the cycloalkadiene should be avoided. A preferred order of addition is to combine the compound of Formula 5, the cycloalkadiene, the metal reducing agent and the solvent.

In the second step, the mixture prepared in the first step is contacted with a compound of Formula 2 and at least one compound of Formula 3. The ratios of reagents (i.e. Formula 4 to 2, and Formula 3 to Formula 2) are analogous to Scheme 1. Compounds of Formula 3 suitable for this method include those already described for Scheme 1. Commentary in Scheme 1 concerning reducing the particle size of Formula 3 compounds prior to use and techniques for doing so also apply to the method Scheme 9.

When combining the reagents it is especially advantageous to avoid contacting the compounds of Formulae 2 and 4 for any appreciable amount of time in the absence of the compound or compounds of Formula 3. Thus, when conducting the cyanation step in the present method, the most preferred order of addition has been found to comprise adding the compound or compounds of Formula 3 to the reaction mixture comprising the compound of Formula 4 and the suitable solvent, and then adding the compound of Formula 2. If more metal reducing agent is added during the cyanation step, it is typically added just prior to the addition of the compound of Formula 2, or last.

In the method of Scheme 9 an undesirable side reaction can potentially occur involving reduction (i.e. dehalogenation) of the 5-halobenzoic acid derivative of Formula 2 to give the corresponding benzoic acid derivative as a byproduct. Although this side reaction can also occur in the method, of Scheme 1, under the preferred conditions of that method, it usually occurs to only a very minor extent, if at all (i.e. often no greater than 1 to 2 mol %). Without being bound by any particular theory, it is believed that when zinc is used as the metal reducing agent, zinc chloride generated during the reduction of Formula 5 to Formula 4 in the first step promotes the side reaction in the subsequent cyanation step. It has been found that the addition of a base can minimize the formation of this byproduct. The base is preferably a Lewis base, and more preferably an amine Lewis base. A wide variety of primary, secondary and tertiary aliphatic amines are useful in the present method, for example, methylamine, ethylamine or triethylamine. Triethylamine is particularly preferred. Typically molar ratios from about 1 to about 20 of the base relative to the compound Formula 4 are effective in minimizing the presence of the dehalogenated benzoic acid derivative byproduct in the final desired product. If a base is used in the present method, it is typically added to the reaction mixture comprising the freshly prepared compound of Formula 4 prior to adding the compound of Formula 2, or simultaneous to adding the compound of Formula 2.

The method of Scheme 9 is illustrated by Example 5 below. Example 6 below also illustrates the method of Scheme 9 including the addition of a base (triethylamine) to the reaction mixture comprising the freshly prepared compound of Formula 4.

In another aspect of the present invention compounds of the Formula 1 prepared by the method of Scheme 1 or Scheme 9 are useful as intermediates for preparing compounds of Formula 6. Compounds of Formula 6 are useful as insecticides, as described, for example in PCT Patent Publications WO 2003/015518 and WO 2006/055922.

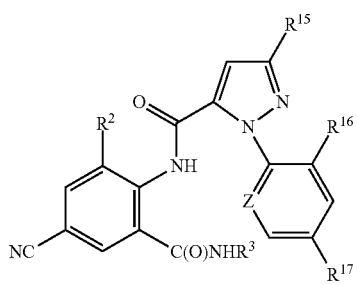

6 wherein
 $R^2$ is $CH_3$ or Cl;
 $R^3$ is H, $C_1$-$C_4$ alkyl, cyclopropyl, cyclopropylcyclopropyl, cyclopropylmethyl or methylcyclopropyl;
 Z is $CR^{18}$ or N;
 $R^{15}$ is Cl, Br, $CF_3$, $OCF_2H$ or $OCH_2CF_3$;
 $R^{16}$ is F, Cl or Br;
 $R^{17}$ is H, F or Cl; and
 $R^{18}$ is H, F, Cl or Br.

A variety of methods are possible for the preparation of a compound of Formula 6 from a compound of Formula 1. As outlined in Scheme 10, one such method involves the coupling of a compound of Formula 1a (Formula 1 wherein $R^1$ is $OR^4$ and $R^4$ is H) with a pyrazole-5-carboxylic acid of Formula 15, resulting in a cyanobenzoxazinone of Formula 16. Subsequent reaction of the cyanobenzoxazinone with an amine of Formula 9 provides a compound of Formula 6. Conditions for the first step involve sequential addition of methanesulfonyl chloride in the presence of a tertiary amine such as triethylamine or pyridine to a pyrazole of Formula 15, followed by the addition of a compound of Formula 1a, followed by a second addition of tertiary amine and methanesulfonyl chloride. The reaction can be run neat or in a variety of suitable solvents including tetrahydrofuran, diethyl ether, dioxane, toluene, dichloromethane or chloroform with optimum temperatures ranging between about ambient temperature (e.g., about 15-40° C.) and the reflux temperature of the solvent. The second step, reaction of benzoxazinones with amines to produce anthranilamides, is well documented in the chemical literature. For a general review of benzoxazinone chemistry see Jakobsen et al., *Biorganic and Medicinal Chemistry* 2000, 8, 2095-2103 and references cited within, and G. M. Coppola, *J. Heterocyclic Chemistry* 1999, 36, 563-588. Also see PCT Patent Publication WO 2004/067528, which teaches the general method shown in Scheme 10, including experimental examples relevant to Scheme 10.

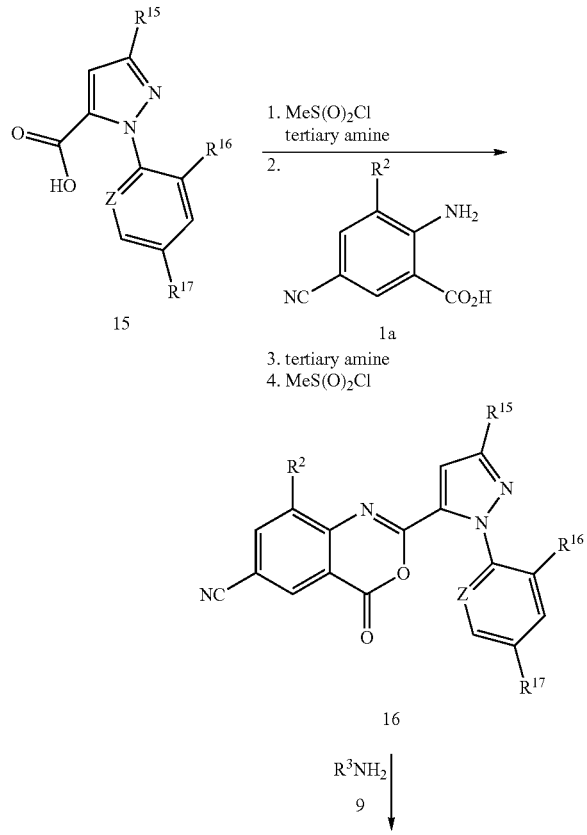

Another method of preparing compounds of Formula 6 is shown in Scheme 11. In this method a compound of Formula 6 is prepared by combining a compound of Formula 1b (Formula 1 wherein $R^1$ is $NHR^3$), a pyrazole of Formula 15 and sulfonyl chloride according to the general method taught in PCT Patent Publication WO 2006/062978, which is hereby incorporated herein in its entirety by reference.

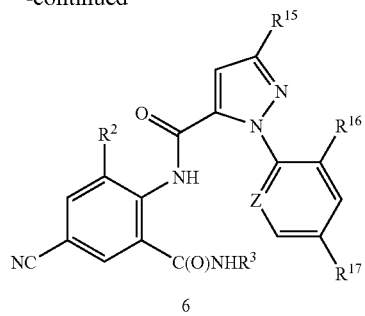

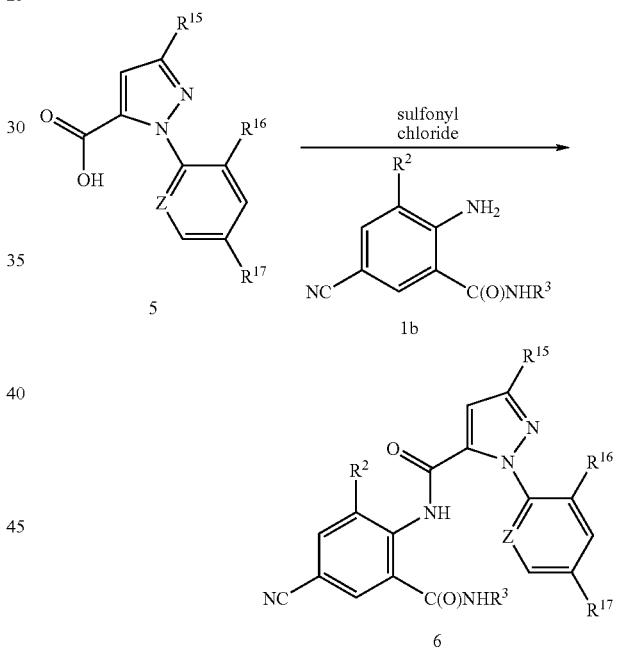

As described in WO 2006/062978 a variety of reaction conditions are possible for this transformation. Typically a sulfonyl chloride is added to a mixture of the compounds of Formulae 1b and 15 in the presence of a solvent and a base. Sulfonyl chlorides are generally of the formula $RS(O)_2Cl$ wherein R is a carbon-based radical. Usually for this method R is $C_1$-$C_4$ alkyl, $C_1$-$C_2$ haloalkyl or phenyl optionally substituted with up to 3 substituents independently selected from the group consisting of halogen, $C_1$-$C_3$ alkyl and nitro. Commercially available sulfonyl chlorides include methanesulfonyl chloride (R is $CH_3$), propanesulfonyl chloride (R is $(CH_2)_2 CH_3$), benzenesulfonyl chloride (R is phenyl), and p-toluenesulfonyl chloride (R is 4-methylphenyl). Methanesulfonyl chloride is of note for reasons of lower cost, ease of addition and/or less waste. At least one molar equivalent of the sulfonyl chloride per mole of the compound of Formula 15 is stoichiometrically needed for complete conversion. Typically the molar ratio of sulfonyl chloride to the compound of Formula 15 is no more than about 2.5, more typically no more than about 1.4.

The compound of Formula 6 is formed when the starting compounds of Formulae 1b, 15 and the sulfonyl chloride are contacted with each other in a combined liquid phase, in which each is at least partially soluble. Since the starting materials of Formulae 1b and 15 are typically solids at ordinary ambient temperatures, the method is most satisfactorily conducted using a solvent in which the starting compounds 3-picoline, 2,6-lutidine, and pyridine. Of particular note as the base is 3-picoline, as its salts with carboxylic acids of Formula 15 are often highly soluble in solvents such as acetonitrile.

The compounds of Formula 6 can be isolated from the reaction mixtures by methods known to those skilled in the art, including crystallization, filtration and extraction. As disclosed in WO 2006/062978, in some cases under the coupling reaction conditions of Scheme 11 compounds of Formula 6, can partially cyclize to form iminobenzoxazine derivatives of Formula 17, as shown in Scheme 12.

Scheme 12

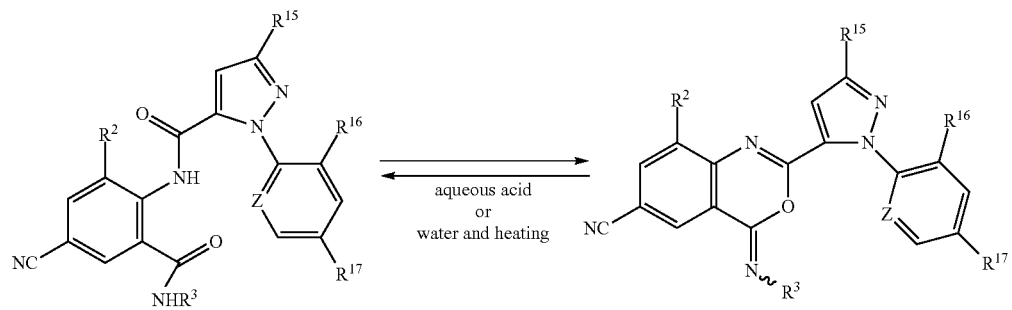

have significant solubility. Thus typically the method is conducted in a liquid phase comprising a solvent. In some cases the carboxylic acid of Formula 15 may have only slight solubility, but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, propionitrile, ethyl acetate, acetone, MEK, dichloromethane, methyl tert-butyl ether, THF, p-dioxane, toluene, and chlorobenzene. Of particular note as the solvent is acetonitrile, as it often provides products in superior yield and/or purity.

As the reaction of the method of Scheme 11 generates hydrogen chloride as a byproduct, which would otherwise bind to basic centers on the compounds of Formulae 1b, 6 and 15, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 15 forms a salt, which may have greater solubility than the carboxylic acid in the reaction medium. Although the base can be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as the solvent the nominal molar ratio of the base to the sulfonyl chloride is typically from about 2.0 to about 2.2, and is preferably from about 2.1 to about 2.2. Preferred bases are tertiary amines, including substituted pyridines. More preferred bases include 2-picoline, As discussed in WO 2006/062978, in these cases it is often advantageous to convert the iminobenzoxazine compounds of Formula 17 back to the amides of Formula 6 prior to isolation. This conversion can be accomplished by treatment of the reaction mixture with an aqueous acid solution (e.g., aqueous hydrochloric acid); or by isolating the mixture of Formulae 17 and 6 compounds, and then treating the mixture with an aqueous acid solution, optionally in the presence of a suitable organic solvent (e.g., acetonitrile). WO 2006/062978 discloses specific examples relevant to the method of Scheme 11, including examples illustrating treatment of the reaction mixture with an aqueous acid solution prior to isolating compounds of Formula 6. Also, Example 6 below illustrates the method of Scheme 11 including treatment of the reaction mixture with water and hydrochloric acid prior to isolating the Formula 6 product.

Alternatively, compounds of Formula 17 can be converted back to compounds of Formula 6 prior to isolation by contacting the reaction mixture with water and heating. Typically, the conversion of Formula 17 compounds to Formula 6 compounds can be achieved by adding between about 2 to 6 parts by weight of water relative to the weight of the starting compound of Formula 1 and then heating to between about 45 and 65° C. The conversion of the compound of Formula 17 to the compound Formula 6 is usually complete in 1 h or less. Reference Example 4 below illustrates the method of Scheme 11 including the treatment of the reaction mixture with water and heating prior to isolating the compound of Formula 6.

Pyrazole-5-carboxylic acids of Formula 15 can be prepared from 5-oxo-3-pyrazolidinecarboxylates by treatment with a halogenating agent to give 3-halo-4,5-dihydro-1H-pyrazole-5-carboxylates, which can subsequently be treated with an oxidizing agent to provide the esters, and then converted to the acids (i.e. Formula 15). Halogenating agents that can be used include, for example, phosphorus oxyhalides, phosphorus trihalides, phosphorus pentahalides, thionyl chloride, dihalotrialkylphosphoranes, dihalodiphenylphosphoranes, oxalyl chloride and phosgene. The oxidizing agents can be, for example, hydrogen peroxide, organic peroxides, potassium persulfate, sodium persulfate, ammonium persulfate, potassium monopersulfate (e.g., Oxone®) or potassium permanganate. See PCT Patent Publications WO 2003/016283, WO 2004/087689 and WO 2004/011453 for a description of the halogenation and oxidation methods, and a procedure for preparing the starting 5-oxo-3-pyrazolidinecarboxylates. A variety of methods reported in the chemical literature can be use to convert the esters to carboxylic acids, including nucleophilic cleavage under anhydrous conditions or hydrolysis involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). Base-catalyzed hydrolytic methods are preferred to prepare the carboxylic acids of Formula 15 from the corresponding esters. Suitable bases include alkali metal (such as lithium, sodium, or potassium) hydroxides. For example, the esters can be dissolved in a mixture of water and alcohol such as methanol. Upon treatment with sodium hydroxide or potassium hydroxide, the esters saponify to provide the sodium or potassium salt of the carboxylic acid. Acidification with a strong acid, such as hydrochloric acid or sulfuric acid, gives the carboxylic acids. PCT Patent Publication WO 2003/016283 provides a relevant experimental example illustrating the base-catalyzed hydrolysis method for the conversion of an ester to an acid.

Alternatively, pyrazole-5-carboxylic acids of Formula 15 can be prepared starting from 4,5-dihydro-5-hydroxy-1H-pyrazole-5-carboxylates via an acid-catalyzed dehydration reaction which provides the esters of Formula 15, which can then be converted to the acids. Typical reaction conditions involve treatment of 4,5-dihydro-5-hydroxy-1H-pyrazole-5-carboxylates with an acid, for example, sulfuric acid, in an organic solvent, such as acetic acid, at temperatures between about 0 and 100° C. The method is described PCT Patent Publication WO 2003/016282. Conversion of the esters to acids can be done using the methods described above. Also, WO 2003/016282 provides a relevant experimental example for the conversion of an ester to an acid.

Anthranilic amides of Formula 1b can also be prepared from the corresponding acids or esters of Formula 1c (Formula 1 wherein $R^1$ is $OR^4$ and $R^4$ is H or $C_1$-$C_4$ alkyl) as shown below in Scheme 13. Forming amides from carboxylic acids typically involves addition of a coupling agent (e.g., silicon tetrachloride, or alternatively dicyclohexylcarbodiimide or 1-ethyl-3-(3-dimethylaminopropyl)carbodiimide often in the presence of 1-hydroxy-benzotriazole). Preparation of anthranilic amides from anthranilic acids is disclosed in M. J. Kornet, *Journal of Heterocyclic Chemistry* 1992, 29(1), 103-5; PCT Publication WO 01/66519-A2; T. Asano et al., *Bioorganic & Medicinal Chemistry Letters* 2004, 14(9), 2299-2302; H. L. Birch et al., *Bioorganic & Medicinal Chemistry Letters* 2005, 15(23), 5335-5339; and D. Kim et al., *Bioorganic & Medicinal Chemistry Letters* 2005, 15(8), 2129-2134. Also T. Asano et al. reports preparation of an anthranilic amide from an anthranilic acid through an N-protected aniline intermediate or through a 4H-3,1-benzoxazine-2,4 (1H)-dione (isatoic anhydride) intermediate. Forming amides from esters often involves heating the ester with the appropriate amine in a polar solvent such as ethylene glycol. A procedure useful for conversion of anthranilic esters to anthranilic amides is described in PCT Patent Publication WO 2006/062978. Also, E. B. Skibo et al., *Journal of Medicinal Chemistry* 2002, 45(25), 5543-5555 discloses preparation of an anthranilic amide from the corresponding anthranilic ester using sodium cyanide catalyst.

Scheme 13

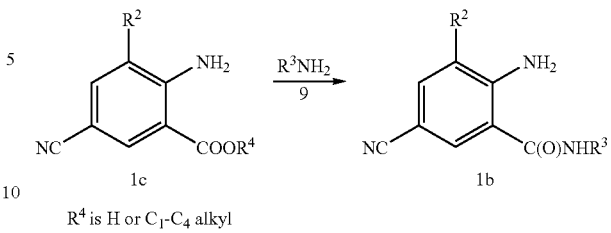

$R^4$ is H or $C_1$-$C_4$ alkyl

The methods of Schemes 10 and 11 are illustrative of just two of many methods for converting a compound of Formula 1 to a carboxamide of Formula 6. A wide variety of general methods are known in the art for preparing carboxamides from carboxylic acids and amines. For a general review, see M. North, *Contemporary Org. Synth.* 1995, 2, 269-287. Particular methods include contacting a compound of Formula 1b with a compound of Formula 15 in the presence of a dehydrating coupling agent such as 1,1'-carbonyldiimidazole, bis(2-oxo-3-oxazolidinyl)phosphinic chloride or benzotriazol-1-yloxy-tris(dimethylamino)phosphonium hexafluorophosphate, or a polymer-bound analogous reagent such as polymer-bound dicyclohexylcarbodiimide, typically in an inert solvent such as dichloromethane or N,N-dimethylformamide, as is generally disclosed in PCT Patent Publication WO 2003/15518. Also disclosed in WO 2003/15518 is a method of preparing an acyl chloride derivative of the compound of Formula 15 by contacting Formula 15 compounds with thionyl chloride or oxalyl chloride in the presence of a catalytic amount of N,N-dimethylformamide, and then contacting the derived acyl chloride with the compound of Formula 1b in the presence of an acid scavenger, such as an amine base (e.g., triethylamine, N,N-diisopropylethylamine, pyridine, and polymer-supported analogs) or a hydroxide or carbonate (e.g., NaOH, KOH, $Na_2CO_3$, $K_2CO_3$), typically in an inert solvent such as tetrahydrofuran, 1,4-dioxane, ethyl ether or dichloromethane. The product, compounds of Formula 6, can be isolated from the reaction mixtures by methods known to those skilled in the art, including crystallization, filtration, and extraction.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. In the following Examples, the term "oxygen-free" when used in connection with a solvent refers to a solvent in which atmospheric oxygen was removed before use by distilling in an inert atmosphere in the presence of calcium hydride. The term "activated zinc dust" when used in the following Examples refers to commercially obtained zinc dust that was activated prior to use by stirring for about 10 minutes in a solution of hydrochloric acid (1 N) while applying a slow nitrogen purge, and then filtering, washing with water and acetonitrile, and drying. In the following Examples, reference to particle mesh size (e.g., "particle size −200 mesh (−74 μm)") means at the specified mesh size, for a given quantity of material, 10% by weight of the material has a particle size larger than the specified size and the other 90% by weight has a particle size smaller than the specified mesh size (i.e. 90% by weight of the material will pass through the specified mesh size). In Examples 2 and 3 the purity of the product 2-amino-5-cyano-N,3-dimethylbenzamide was determined by reversed phase HPLC (HP Zorbax® Eclipse XDB-C8, manufactured by Agilent Technologies, 5 μm, 4.6 mm×75 mm). The solvent system was solvent A: water with 0.1% by weight trifluoroacetic acid, and solvent B: acetonitrile with 0.1% trifluoroacetic acid (gradient started at 0 minutes with 95% solvent A and 5% solvent B and increased solvent B to 95% over 8 minutes, flow was 1 mL/minute). $^1$H NMR and $^{31}$P NMR spectra are reported in ppm downfield from tetramethylsilane and phosphoric acid, respectively; s means singlet, d means doublet, m means multiplet and br s means broad singlet.

REFERENCE EXAMPLE 1

Preparation of
2-amino-5-bromo-N,3-dimethylbenzamide (a compound of Formula 2)

A 1000-mL flask equipped with a mechanical stirrer, thermocouple, condenser and Teflon® fluoropolymer tubing (1/16" (0.16) cm I.D.×1/8" (0.32 cm) O.D.) (positioned such that the end of the tubing was submerged below the surface of the reaction mixture) was charged with acetic acid (226 mL). A solution of aqueous sodium hydroxide (50%, 25 g) in water (85 g) was added over 15 minutes, and then 2-amino-N,3-dimethylbenzamide (50 g, 0.305 mol) (see PCT Patent Publication WO 2006/062978 for a method of preparation) was added and the mixture was heated at 55° C. A two-necked 200-mL flask fitted on one neck with a Teflon® tubing dip tube was charged with liquid bromine (50.1 g), and the other neck was connected to the Teflon® tubing on the 1000-mL flask. Nitrogen gas was then flowed through the dip tube below the surface of the liquid bromine at a rate of about 0.012 m$^3$ (0.4 cu ft) per h for 2.5 h, during which time all of the bromine evaporated and the bromine vapor entrained in the nitrogen gas flowed out of the two-necked 200-mL flask and entered the reaction mixture through the Teflon® tubing. The reaction temperature was held at about 55° C. during the bromine vapor addition and for 30 minutes thereafter, and then cooled to 45° C. and stirred overnight. A solution of aqueous sodium hydroxide (50%, 52 g) in water (88 mL) was added to the reaction mixture at a rate of 0.8 mL/minute. After about 10% of the total volume of the sodium hydroxide solution had been added, the addition was stopped and the reaction mixture was stirred for 1 h at 45° C. After 1 h the remaining sodium hydroxide solution was added at a rate of 0.8 mL/minute. After the addition was complete, the reaction was stirred for 30 minutes at 45° C., and then cooled to 10° C. and stirred for 1 h. The mixture was filtered and the solid collected was washed with methanol (130 mL) and water (260 mL), and then dried to a constant weight in a vacuum-oven at 45° C. to give the title compound as a solid (67 g, 99.4 area % purity by HPLC, 89.7% yield) melting at 133-135° C.

$^1$H NMR (DMSO-d$_6$) δ 8.30 (m, 1H), 7.49 (d, 1H), 7.22 (d, 1H), 6.35 (br s, 2H), 2.70 (d, 3H), 2.06 (s, 3H).

REFERENCE EXAMPLE 2

Preparation of [1,1'-bis(diphenylphosphino)ferrocene][(1,2,5,6)-1,5-cyclooctadiene]-nickel (a compound of Formula 4)

A reaction flask was charged with 1,1'-bis(diphenylphosphino)ferrocene (1.84 g, 3.32 mmol), bis(1,5-cyclooctadiene)nickel (0.75 g, 2.80 mmol) and oxygen-free toluene (10 mL) under a nitrogen atmosphere in a glovebox. After stirring for 4 h at room temperature, hexanes (40 mL) were added to the reaction mixture. The reaction mixture was allowed to stand overnight, and then the solvents were decanted off and the orange-yellow solid remaining was washed with hexanes. The solid was dried under vacuum to give the title compound as an orange-yellow solid (1.86 g, 78% yield).

$^{31}$P NMR (benzene-d$_6$): δ 38.4 (s).

REFERENCE EXAMPLE 3

Preparation of [1,1'-bis(diphenylphosphino)ferrocene][(1,2,5,6)-1,5-cyclooctadiene]-nickel (a compound of Formula 4)

A four-necked 100-mL round bottom flask equipped with a magnetic stirrer, thermocouple and condenser was charged with nickel chloride hexahydrate (3.57 g, 15.0 mmol), 1,1'-bis(diphenylphosphino)ferrocene (18.50 g, 15.0 mmol), oxygen-free ethanol (35 mL) and oxygen-free toluene (35 mL) under a nitrogen atmosphere in a glovebox. The stirred mixture was heated at about 75° C. for 30 minutes, and then cooled to room temperature, and 1,5-cyclooctadiene (9.21 mL, 75.1 mmol) and activated zinc dust (1.29 g, 19.50 mmol) were added. After stirring for approximately 30 minutes the reaction mixture became very thick with solids, and more oxygen-free ethanol (10 mL) was added. After stirring for a further 8 h the resulting orangish slurry was filtered, and the solid collected was washed with ethanol (3×10 mL) and then dried under vacuum to give the title compound as an orange powder (10.80 g including residual zinc).

$^{31}$P NMR (THF-d$_8$) δ 37.3 (s).

EXAMPLE 1

Preparation of [1,1'-bis(diphenylphosphino)ferrocene][(1,2,5,6)-1,5-cyclooctadiene]-nickel (a compound of Formula 4)

A 20-mL scintillation vial was charged with [1,1'-bis(diphenyl-phosphino)ferrocene)dichloronickel (0.50 g, 0.709 mmol), 1,5-cyclooctadiene (0.384 g, 3.55 mmol), oxygen-free acetonitrile (10 mL) and activated zinc dust (0.080 g, 1.205 mmol) under a nitrogen atmosphere in a glovebox. The reaction mixture was stirred at room temperature for about 16 h, and then the resulting orange slurry was filtered. The solid collected was washed with acetonitrile (3 mL) and then dried under vacuum to give the title compound as an orangish powder (0.477 g including residual zinc).

$^{31}$P NMR (THF-d$_8$) δ 35.4 (s).

EXAMPLE 2

Preparation of
2-amino-5-cyano-N,3-dimethylbenzamide (a compound of Formula 1)

A three-necked 250-mL round bottom flask equipped with a magnetic stirrer, thermocouple and condenser was charged with of 2-amino-5-bromo-N,3-dimethylbenzamide (prepared by the method of Reference Example 1) (10.0 g, 41.1 mmol), sodium cyanide (2.26 g, 44.6 mmol, ground prior to use), zinc (0.815 g, 12.3 mmol, 23.6 meq, particle size –200 mesh (–74 μm)) and [1,1'-bis(diphenylphosphino)ferrocene][(1,2,5,6)-1,5-cyclooctadiene]nickel (prepared by the method of Reference Example 2) (0.297 g, 0.41 mmol) under a nitrogen atmosphere in a glovebox. The flask was removed from the glovebox and swept with nitrogen for 1 h, after which time oxygen-free acetonitrile (48 mL) was added by syringe. The reaction mixture was heated at 80° C. for about 3 h. After 3 h, HPLC analysis of the reaction mixture indicated complete conversion of the 2-amino-5-bromo-N,3-dimethylbenzamide with 2-amino-5-cyano-N,3-dimethylbenzamide being the major product and 2-amino-N,3- dimethylbenzamide a minor product (molar ratio 98.5 to 1.5). Toluene (55 mL) was added to the reaction mixture, and most of the acetonitrile solvent was removed by distillation at atmospheric pressure (67 mL of distillate boiling at 80-82° C. was collected). Toluene (20 mL) and water (20 mL) were added to the concentrated reaction mixture, and the mixture was heated at reflux for 1.5 h, and then cooled to room temperature and filtered. The solid collected was washed with water (90 mL) and dried under vacuum at 45° C. to give the title compound as an off-white powder (7.96 g, 91.4% purity by HPLC, 93.4% yield).

EXAMPLE 3

A Second Preparation of 2-amino-5-cyano-N,3-dimethylbenzamide

A four-necked 100-mL round bottom flask equipped with a magnetic stirrer, thermocouple and condenser was charged with of 2-amino-5-bromo-N,3-dimethylbenzamide (prepared by the method of Reference Example 1) (2.50 g, 10.28 mmol), sodium cyanide (0.564 g, 11.16 mmol, ground prior to use), zinc (0.204 g, 6.18 meq, 3.09 mmol, particle size –200 mesh (–74 μm)), [1,1'-bis(diphenylphosphino)ferrocene][(1,2,5,6)-1,5-cyclooctadiene]nickel (prepared by the method of Reference Example 2) (0.074 g, 0.10 mmol) and oxygen-free butyronitrile (12 mL) under a nitrogen atmosphere in a glovebox. The reaction mixture was heated at 80° C. for about 3 h. After 3 h, HPLC analysis showed a mixture of 2-amino-5-bromo-N,3-dimethylbenzamide, 2-amino-5-cyano-N,3-dimethylbenzamide and 2-amino-N,3-dimethyl-benzamide in a molar ratio of 66:31:3.

EXAMPLE 4

A Third Preparation of 2-amino-5-cyano-N,3-dimethylbenzamide

A four-necked 100-mL round bottom flask equipped with a magnetic stirrer, thermocouple and condenser was charged with 2-amino-5-bromo-N,3-dimethylbenzamide (2.50 g, 10.28 mmol, prepared by the method of Reference Example 1), sodium cyanide (97%, 0.566 g, 11.21 mmol, ground prior to use), polymethylhydrosiloxane (0.082 mL, 1.37 meq), [1,1'-bis(diphenylphosphino)ferrocene][(1,2,5,6)-1,5-cyclooctadiene]nickel (0.074 g, 0.10 mmol, prepared by the method of Reference Example 3) and oxygen-free acetonitrile (12 mL) under a nitrogen atmosphere in a glovebox. The reaction mixture was heated at 70° C. After about 3 h, HPLC analysis of the reaction mixture indicated complete conversion of the 2-amino-5-bromo-N,3-dimethylbenzamide with 2-amino-5-cyano-N,3-dimethylbenzamide being the major product. The thick reaction mixture was cooled to room temperature and removed from the glovebox. Xylenes (15 mL) and polyethylene glycol (0.80 mL) were added to the reaction mixture, and most of the acetonitrile solvent was removed by distillation at atmospheric pressure (11.2 mL of distillate boiling at 80-85° C. was collected). More xylenes (1 mL) were added to the concentrated reaction mixture and stirring was continued at about 70° C. for 20 minutes. The reaction mixture was cooled to about 25° C., water (15 mL) was added and stirring was continued for about 10 minutes. The mixture was filtered, and the solid collected was washed with xylenes-water (1:1 mixture, 2×3 mL) and xylenes (1×3 mL), and then dried under vacuum at about 55° C. to give the title compound as an off-white powder (1.92 g, 97.7% purity by HPLC, 96% yield).

$^1$H NMR (DMSO-$d_6$) δ 2.10 (s, 3H), 2.74 (d, 3H), 7.18 (br s, 2H), 7.44 (d, 1H), 7.82 (d, 1H), 8.43 (br m, 1H).

EXAMPLE 5

Preparation of 2-amino-5-cyano-N,3-dimethylbenzamide (a compound of Formula 1, prepared by the method of Scheme 9)

A reaction flask was charged with of [1,1'-bis(diphenylphosphino)ferrocene]-dichloronickel (68 mg, 0.099 mmol), zinc (130 mg, 1.99 mmol), 1,5-cyclooctadiene (28.3 mg, 0.262 mmol) and oxygen-free acetonitrile (4 mL) under a nitrogen atmosphere in a glovebox. After stirring for 2 h at room temperature, sodium cyanide (0.55 g, 11.22 mmol, ground prior to use), 2-amino-5-bromo-N,3-dimethylbenzamide (prepared by the method of Reference Example 1) (2.43 g, 9.99 mmol) and more oxygen-free acetonitrile (8 mL) were added to the reaction mixture. The flask was removed from the glovebox while maintaining a nitrogen atmosphere, and the reaction mixture was then heated at reflux (about 82° C.) while being vigorously stirred. After about 2 h and 25 minutes, HPLC analysis of the reaction mixture indicated about 96% conversion of the 2-amino-5-bromo-N,3-dimethylbenzamide with 2-amino-5-cyano-N,3-dimethylbenzamide being the major product. A portion of the reaction mixture (0.05 mL) was withdrawn and evaporated to dryness to give an analytical sample for $^1$H NMR analysis.

$^1$H NMR (CDCl$_3$) δ 2.1 (s, 3H), 2.9 (d, 3H), 6.0 (br s, 1H, NH), 6.2 (br s, 2H, NH$_2$), 7.3 (s, 1H), 7.5 (d, 1H).

EXAMPLE 6

Preparation of 2-amino-5-cyano-N,3-dimethylbenzamide (a second preparation of a compound of Formula 1 by the method of Scheme 9)

A four-necked 100-mL round bottom flask equipped with a magnetic stirrer, thermocouple and condenser was charged with [1,1'-bis(diphenyl-phosphino)ferrocene)dichloronickel (97%, 0.073 g, 0.10 mmol), zinc (0.204 g, 3.09 mmol, particle size –200 mesh (–74 μm)), 1,5-cyclooctadiene (0.022 g, 0.21 mmol), and oxygen-free acetonitrile (3 mL) under a nitrogen atmosphere in a glovebox. The reaction mixture was stirred at ambient temperature for about 1 h, during which time the initially dark green reaction mixture formed a bright, yellow-orange slurry. To the reaction mixture was added 2-amino-5-bromo-N,3-dimethylbenzamide (2.50 g, 10.28 mmol, prepared by the method of Reference Example 1), sodium cyanide (97%, 0.564 g, 11.16 mmol, ground prior to use), zinc (0.068 g, 1.0 mmol, particle size –200 mesh), triethylamine (0.105 g, 1.03 mmol) and oxygen-free acetonitrile (9.5 mL). The reaction mixture was heated at 80° C. After about 2.5 h, HPLC analysis of the reaction showed a mixture of 2-amino-5-cyano-N,3-dimethylbenzamide, 2-amino-5-bromo-N,3-dimethylbenzamide, and 2-amino-N,3-dimethyl-benzamide in a molar ratio of 96.7:2.0:1.3, respectively.

EXAMPLE 7

Preparation of 3-bromo-1-(3-chloro-2-pyridinyl)-N-[4-cyano-2-methyl-6-[(methylamino)carbonyl]phenyl]-1H-pyrazole-5-carboxamide (a compound of Formula 6)

A four-necked 300-mL bottom drain resin kettle equipped with thermocouple, mechanical stirrer and reflux condenser was charged with 2-amino-5-bromo-N,3-dimethylbenzamide (31.25 g, 0.128 mol, prepared by the method of Reference Example 1), sodium cyanide (97%, 7.079 g, 0.140 mol, ground prior to use) and [1,1'-bis-(diphenylphosphino)ferrocene][(1,2,5,6)-1,5-cyclooctadiene]nickel (0.074 g, 0.10 mmol; prepared by the method of Reference Example 3). The reaction vessel was degassed by applying a vacuum and then repressurizing to atmospheric pressure with nitrogen (method repeated 5 times). Oxygen-free acetonitrile (150 mL) and polymethylhydrosiloxane (3.11 mL, 52 meq) were added to the reaction mixture by syringe, and the mixture was vigorously stirred and heated at 72° C. After 3 h HPLC analysis indicated conversion of the 2-amino-5-bromo-N,3-dimethylbenzamide with 2-amino-5-cyano-N,3-dimethylbenzamide being the major product and 2-amino-N,3-dimethylbenzamide the minor product (molar ratio 97.8 to 1.5). The reaction mixture was allowed to cool to room temperature.

To the above reaction mixture was added 3-bromo-1-(3-chloro-2-pyridinyl)-1H-pyrazole-5-carboxylic acid (see PCT Patent Publication WO 2003/015519 for a method of preparation) (97.6% purity, 37.79 g, 0.12 mmol), 3-picoline (34.16 g, 0.37 mol), and acetonitrile (50 mL). The reaction mixture was cooled to about 15° C., and methanesulfonyl chloride (21.71 g, 0.19 mmol) was added in four portions over 20 minutes. The mixture was stirred for about 2.5 h at 23° C. and then for about 2.5 h at 38° C. More methanesulfonyl chloride (1.40 g) was added, the reaction mixture was cooled to 30° C., and then water (95 mL) was added followed by hydrochloric acid (12 N, 6 mL). The mixture was stirred at room temperature for two days, and then drained from the reaction vessel and filtered, and the solid collected was washed with acetonitrile-water (2:1 mixture, 2×30 mL) and water (2×30 mL). Residual solids left in the reaction vessel were dissolved in THF (50 mL), and the resulting solution was evaporated to dryness. The residue was triturated with acetonitrile-water (2:1 mixture, 6 mL), and the solids were collected by filtration. The combined solids were dried under vacuum at 55° C. to give the title compound as an off-white powder (55.74 g, 94.6% purity by HPLC, 91% yield).

$^1$H NMR (DMSO-$d_6$) δ 2.21 (s, 3H), 2.67 (d, 3H), 7.42 (s, 1H), 7.61 (dd, 1H), 7.76 (d, 1H), 7.88 (d, 1H), 8.18 (dd, 1H), 8.38 (br q, 1H), 8.50 (dd, 1H), 10.53 (s, 1H).

REFERENCE EXAMPLE 4

Preparation of 3-bromo-1-(3-chloro-2-pyridinyl)-N-[4-cyano-2-methyl-6-[(methylamino)carbonyl]phenyl]-1H-pyrazole-5-carboxamide (a compound of Formula 6)

To a mixture of 3-bromo-1-(3-chloro-2-pyridinyl)-1H-pyrazole-5-carboxylic acid (see PCT Patent Publication WO 2003/015519 for a method of preparation) (97.4% purity, 15.4 g, 49.6 mmol) and 2-amino-5-cyano-N,3-dimethylbenzamide (10.0 g, 52.5 mmol) in acetonitrile (80 mL) was added 3-picoline (13.9 g, 148 mmol). The mixture was cooled to 15 to 20° C., and then methanesulfonyl chloride (8.2 g, 71.2 mmol) was added dropwise at 15 to 20° C. After 1 h, water (37.3 g) was added dropwise to the reaction mixture while maintaining the temperature at 15 to 20° C. After the addition was complete, the mixture was heated at 45 to 50° C. for 30 minutes, and then cooled to 15 to 25° C. for 1 h. The mixture was filtered, and the solids collected were washed with acetonitrile-water (approximately a 5:1 mixture, 2×10 mL) and acetonitrile (2×10 mL), and then dried under nitrogen to afford 24.0 g (93.6% corrected yield based on an assay of 91.6%, with a water content of 6%) of the title compound as an off-white solid.

$^1$H NMR (DMSO-$d_6$) δ 10.53 (br s, 1H) 8.49 (dd, 1H), 8.36 (m, 1H), 8.16 (dd, 1H), 7.87 (d, 1H), 7.76 (d, 1H), 7.60 (m, 1H), 7.41 (s, 1H), 2.67 (d, 3H), 2.21 (s, 3H).

Table 1 illustrates particular transformations to prepare compounds of Formula 1 according to a method of the present invention. The conversion of a compound of Formula 2 to a compound of Formula 1 can, for example, be accomplished according to the method of Scheme 1 or Scheme 9. For these transformations each $R^5$, $R^6$, $R^7$ and $R^8$ is a phenyl ring, and $R^9$ and $R^{10}$ together are 1,5-cyclooctadiene. In Table 1 and the following tables: t means tertiary, s means secondary, n means normal, i means iso, c means cyclo, Me means methyl, Et means ethyl, Pr means propyl, and Bu means butyl. Concatenations of groups are abbreviated similarly; for example, "c-PrCH$_2$" means cyclopropylmethyl

TABLE 1

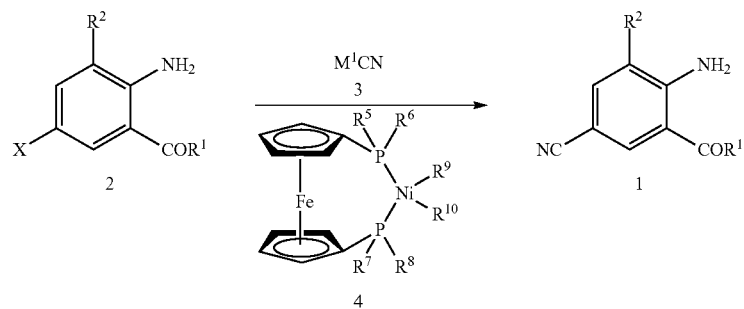

| $R^1$ is NHR$^3$, X is Br and M$^1$ is Na. | | $R^1$ is NHR$^3$, X is Cl and M$^1$ is Na. | | $R^1$ is NHR$^3$, X is I and M$^1$ is Na. | |
|---|---|---|---|---|---|
| $R^2$ | $R^3$ | $R^2$ | $R^3$ | $R^2$ | $R^3$ |
| Me | H | Me | H | Me | H |
| Me | Me | Me | Me | Me | Me |
| Me | Et | Me | Et | Me | Et |
| Me | n-Pr | Me | n-Pr | Me | n-Pr |
| Me | i-Pr | Me | i-Pr | Me | i-Pr |
| Me | n-Bu | Me | n-Bu | Me | n-Bu |
| Me | i-Bu | Me | i-Bu | Me | i-Bu |

TABLE 1-continued

| | | | | | |
|---|---|---|---|---|---|
| Me | s-Bu | Me | s-Bu | Me | s-Bu |
| Me | t-Bu | Me | t-Bu | Me | t-Bu |
| Me | c-Pr | Me | c-Pr | Me | c-Pr |
| Me | c-PrCH$_2$ | Me | c-PrCH$_2$ | Me | c-PrCH$_2$ |
| Me | 1-CH$_3$-c-Pr | Me | 1-CH$_3$-c-Pr | Me | 1-CH$_3$-c-Pr |
| Me | 2-CH$_3$-c-Pr | Me | 2-CH$_3$-c-Pr | Me | 2-CH$_3$-c-Pr |
| Me | 1,1'-bicyclopropyl-2-yl | Me | 1,1'-bicyclopropyl-2-yl | Me | 1,1'-bicyclopropyl-2-yl |
| Me | 1,1'-bicyclopropyl-1-yl | Me | 1,1'-bicyclopropyl-1-yl | Me | 1,1'-bicyclopropyl-1-yl |
| Me | (1R,2S)-1,1'-bicyclopropyl-2-yl | Me | (1R,2S)-1,1'-bicyclopropyl-2-yl | Me | (1R,2S)-1,1'-bicyclopropyl-2-yl |

| R$^1$ is NHR$^3$, X is Br and M$^1$ is K. | | R$^1$ is NHR$^3$, X is Cl and M$^1$ is K. | | R$^1$ is NHR$^3$, X is I and M$^1$ is K. | |
|---|---|---|---|---|---|
| R$^2$ | R$^3$ | R$^2$ | R$^3$ | R$^2$ | R$^3$ |
| Me | H | Me | H | Me | H |
| Me | Me | Me | Me | Me | Me |
| Me | Et | Me | Et | Me | Et |
| Me | n-Pr | Me | n-Pr | Me | n-Pr |
| Me | i-Pr | Me | i-Pr | Me | i-Pr |
| Me | n-Bu | Me | n-Bu | Me | n-Bu |
| Me | i-Bu | Me | i-Bu | Me | i-Bu |
| Me | s-Bu | Me | s-Bu | Me | s-Bu |
| Me | t-Bu | Me | t-Bu | Me | t-Bu |
| Me | c-Pr | Me | c-Pr | Me | c-Pr |
| Me | c-PrCH$_2$ | Me | c-PrCH$_2$ | Me | c-PrCH$_2$ |
| Me | 1-CH$_3$-c-Pr | Me | 1-CH$_3$-c-Pr | Me | 1-CH$_3$-c-Pr |
| Me | 2-CH$_3$-c-Pr | Me | 2-CH$_3$-c-Pr | Me | 2-CH$_3$-c-Pr |
| Me | 1,1'-bicyclopropyl-2-yl | Me | 1,1'-bicyclopropyl-2-yl | Me | 1,1'-bicyclopropyl-2-yl |
| Me | 1,1'-bicyclopropyl-1-yl | Me | 1,1'-bicyclopropyl-1-yl | Me | 1,1'-bicyclopropyl-1-yl |
| Me | (1R,2S)-1,1'-bicyclopropyl-2-yl | Me | (1R,2S)-1,1'-bicyclopropyl-2-yl | Me | (1R,2S)-1,1'-bicyclopropyl-2-yl |

| R$^1$ is NHR$^3$, X is Br and M$^1$ is Na. | | R$^1$ is NHR$^3$, X is I and M$^1$ is Na. | | R$^1$ is NHR$^3$, X is Br and M$^1$ is K. | | R$^1$ is NHR$^3$, X is I and M$^1$ is K. | |
|---|---|---|---|---|---|---|---|
| R$^2$ | R$^3$ | R$^2$ | R$^3$ | R$^2$ | R$^3$ | R$^2$ | R$^3$ |
| Cl | H | Cl | H | Cl | H | Cl | H |
| Cl | Me | Cl | Me | Cl | Me | Cl | Me |
| Cl | Et | Cl | Et | Cl | Et | Cl | Et |
| Cl | n-Pr | Cl | n-Pr | Cl | n-Pr | Cl | n-Pr |
| Cl | i-Pr | Cl | i-Pr | Cl | i-Pr | Cl | i-Pr |
| Cl | n-Bu | Cl | n-Bu | Cl | n-Bu | Cl | n-Bu |
| Cl | i-Bu | Cl | i-Bu | Cl | i-Bu | Cl | i-Bu |
| Cl | s-Bu | Cl | s-Bu | Cl | s-Bu | Cl | s-Bu |
| Cl | t-Bu | Cl | t-Bu | Cl | t-Bu | Cl | t-Bu |
| Cl | c-Pr | Cl | c-Pr | Cl | c-Pr | Cl | c-Pr |
| Cl | c-PrCH$_2$ | Cl | c-PrCH$_2$ | Cl | c-PrCH$_2$ | Cl | c-PrCH$_2$ |
| Cl | 1-CH$_3$-c-Pr | Cl | 1-CH$_3$-c-Pr | Cl | 1-CH$_3$-c-Pr | Cl | 1-CH$_3$-c-Pr |
| Cl | 2-CH$_3$-c-Pr | Cl | 2-CH$_3$-c-Pr | Cl | 2-CH$_3$-c-Pr | Cl | 2-CH$_3$-c-Pr |
| Cl | 1,1'-bicyclopropyl-2-yl | Cl | 1,1'-bicyclopropyl-2-yl | Cl | 1,1'-bicyclopropyl-2-yl | Cl | 1,1'-bicyclopropyl-2-yl |
| Cl | 1,1'-bicyclopropyl-1-yl | Cl | 1,1'-bicyclopropyl-1-yl | Cl | 1,1'-bicyclopropyl-1-yl | Cl | 1,1'-bicyclopropyl-1-yl |

| R$^1$ is OR$^4$, X is Br and M$^1$ is Na. | | R$^1$ is OR$^4$, X is Cl and M$^1$ is Na. | | R$^1$ is OR$^4$, X is I and M$^1$ is Na. | |
|---|---|---|---|---|---|
| R$^2$ | R$^4$ | R$^2$ | R$^4$ | R$^2$ | R$^4$ |
| Me | H | Me | H | Me | H |
| Me | Me | Me | Me | Me | Me |
| Me | Et | Me | Et | Me | Et |

| R$^1$ is OR$^4$, X is Br and M$^1$ is K. | | R$^1$ is OR$^4$, X is Cl and M$^1$ is K. | | R$^1$ is OR$^4$, X is I and M$^1$ is K. | |
|---|---|---|---|---|---|
| R$^2$ | R$^4$ | R$^2$ | R$^4$ | R$^2$ | R$^4$ |
| Me | H | Me | H | Me | H |
| Me | Me | Me | Me | Me | Me |
| Me | Et | Me | Et | Me | Et |

| R$^1$ is OR$^4$, X is Br and M$^1$ is Na. | | R$^1$ is OR$^4$, X is I and M$^1$ is Na. | | R$^1$ is OR$^4$, X is Br and M$^1$ is K. | |
|---|---|---|---|---|---|
| R$^2$ | R$^4$ | R$^2$ | R$^4$ | R$^2$ | R$^4$ |
| Cl | H | Cl | H | Cl | H |
| Cl | Me | Cl | Me | Cl | Me |
| Cl | Et | Cl | Et | Cl | Et |

Table 2 illustrates particular transformations to prepare compounds of Formula 6 from compounds of Formula 2 according to the method of the present invention. The conversion of the compound of Formula 2 to the compound of Formula 1 can, for example, be accomplished according to the method of Scheme 1 or Scheme 9. The conversion of the compound of Formula 1 to the compound of Formula 6 can, for example, be accomplished according to the method of Scheme 11 using a sulfonyl chloride such as methanesulfonyl chloride in the presence of a solvent such as acetonitrile and a base such as 3-picoline. For these transformations each $R^5$, $R^6$, $R^7$ and $R^8$ is a phenyl ring, $R^9$ and $R^{10}$ together are 1,5-cyclooctadiene and $M^1$ is Na.

TABLE 2

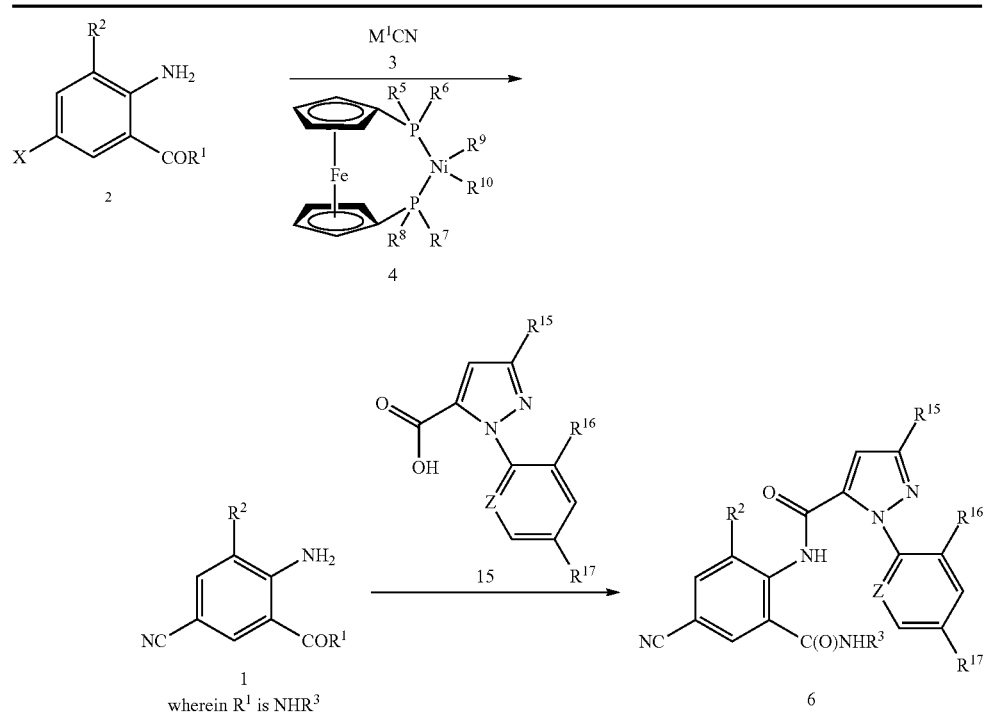

| R³ | R¹⁵ | R¹⁶ | R³ | R¹⁵ | R¹⁶ | R³ | R¹⁵ | R¹⁶ |
|---|---|---|---|---|---|---|---|---|
| R² is Me, X is Br, R¹⁷ is H and Z is N. | | | R² is Me, X is Br, R¹⁷ is H and Z is N. | | | R² is Me, X is Br, R¹⁷ is H and Z is N. | | |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH₂ | Br | F | c-PrCH₂ | Br | Cl | c-PrCH₂ | Br | Br |
| 1-CH₃-c-Pr | Br | F | 1-CH₃-c-Pr | Br | Cl | 1-CH₃-c-Pr | Br | Br |
| 2-CH₃-c-Pr | Br | F | 2-CH₃-c-Pr | Br | Cl | 2-CH₃-c-Pr | Br | Br |
| 1,1'-bicyclopropyl-2-yl | Br | F | 1,1'-bicyclopropyl-2-yl | Br | Cl | 1,1'-bicyclopropyl-2-yl | Br | Br |
| 1,1'-bicyclopropyl-1-yl | Br | F | 1,1'-bicyclopropyl-1-yl | Br | Cl | 1,1'-bicyclopropyl-1-yl | Br | Br |
| H | Cl | F | H | Cl | Cl | H | Cl | Br |
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH₂ | Cl | F | c-PrCH₂ | Cl | Cl | c-PrCH₂ | Cl | Br |
| 1-CH₃-c-Pr | Cl | F | 1-CH₃-c-Pr | Cl | Cl | 1-CH₃-c-Pr | Cl | Br |
| 2-CH₃-c-Pr | Cl | F | 2-CH₃-c-Pr | Cl | Cl | 2-CH₃-c-Pr | Cl | Br |
| 1,1'-bicyclopropyl-2-yl | Cl | F | 1,1'-bicyclopropyl-2-yl | Cl | Cl | 1,1'-bicyclopropyl-2-yl | Cl | Br |
| 1,1'-bicyclopropyl-1-yl | Cl | F | 1,1'-bicyclopropyl-1-yl | Cl | Cl | 1,1'-bicyclopropyl-1-yl | Cl | Br |
| H | OCH₂CF₃ | F | H | OCF₂H | F | H | CF₃ | Br |
| Me | OCH₂CF₃ | F | Me | OCF₂H | F | Me | CF₃ | Br |
| t-Bu | OCH₂CF₃ | F | t-Bu | OCF₂H | F | t-Bu | CF₃ | Br |

TABLE 2-continued

| | | | | | | | | |
|---|---|---|---|---|---|---|---|---|
| 1,1'-bicyclopropyl-1-yl | OCH$_2$CF$_3$ | F | 1,1'-bicyclopropyl-2-yl | OCF$_2$H | F | 1-CH$_3$-c-Pr | CF$_3$ | Br |
| H | OCH$_2$CF$_3$ | Cl | H | OCF$_2$H | Cl | 2-CH$_3$-c-Pr | CF$_3$ | Br |
| Me | OCH$_2$CF$_3$ | Cl | Me | OCF$_2$H | Cl | 1,1'-bicyclopropyl-2-yl | CF$_3$ | Br |
| t-Bu | OCH$_2$CF$_3$ | Cl | t-Bu | OCF$_2$H | Cl | 1,1'-bicyclopropyl-1-yl | CF$_3$ | Br |
| 1,1'-bicyclopropyl-1-yl | OCH$_2$CF$_3$ | Cl | 1,1'-bicyclopropyl-1-yl | OCF$_2$H | Cl | H | CF$_3$ | Cl |
| H | OCH$_2$CF$_3$ | Br | H | OCF$_2$H | Br | Me | CF$_3$ | Cl |
| Me | OCH$_2$CF$_3$ | Br | Me | OCF$_2$H | Br | t-Bu | CF$_3$ | Cl |
| t-Bu | OCH$_2$CF$_3$ | Br | t-Bu | OCF$_2$H | Br | 1-CH$_3$-c-Pr | CF$_3$ | Cl |
| 1,1'-bicyclopropyl-1-yl | OCH$_2$CF$_3$ | Br | 1,1'-bicyclopropyl-1-yl | OCF$_2$H | Br | 2-CH$_3$-c-Pr | CF$_3$ | Cl |
| H | CF$_3$ | F | 1-CH$_3$-c-Pr | CF$_3$ | F | 1,1'-bicyclopropyl-2-yl | CF$_3$ | Cl |
| Me | CF$_3$ | F | 2-CH$_3$-c-Pr | CF$_3$ | F | 1,1'-bicyclopropyl-1-yl | CF$_3$ | Cl |
| t-Bu | CF$_3$ | F | 1,1'-bicyclopropyl-2-yl | CF$_3$ | F | 1,1'-bicyclopropyl-1-yl | CF$_3$ | F |
| R$^2$ is Me, X is Cl, R$^{17}$ is H and Z is N. | | | R$^2$ is Me, X is Cl, R$^{17}$ is H and Z is N. | | | R$^2$ is Me, X is Cl, R$^{17}$ is H and Z is N. | | |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH$_2$ | Br | F | c-PrCH$_2$ | Br | Cl | c-PrCH$_2$ | Br | Br |
| 1-CH$_3$-c-Pr | Br | F | 1-CH$_3$-c-Pr | Br | Cl | 1-CH$_3$-c-Pr | Br | Br |
| 2-CH$_3$-c-Pr | Br | F | 2-CH$_3$-c-Pr | Br | Cl | 2-CH$_3$-c-Pr | Br | Br |
| 1,1'-bicyclopropyl-2-yl | Br | F | 1,1'-bicyclopropyl-2-yl | Br | Cl | 1,1'-bicyclopropyl-2-yl | Br | Br |
| 1,1'-bicyclopropyl-1-yl | Br | F | 1,1'-bicyclopropyl-1-yl | Br | Cl | 1,1'-bicyclopropyl-1-yl | Br | Br |
| H | Cl | F | H | Cl | Cl | H | Cl | Br |
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH$_2$ | Cl | F | c-PrCH$_2$ | Cl | Cl | c-PrCH$_2$ | Cl | Br |
| 1-CH$_3$-c-Pr | Cl | F | 1-CH$_3$-c-Pr | Cl | Cl | 1-CH$_3$-c-Pr | Cl | Br |
| 2-CH$_3$-c-Pr | Cl | F | 2-CH$_3$-c-Pr | Cl | Cl | 2-CH$_3$-c-Pr | Cl | Br |
| 1,1'-bicyclopropyl-2-yl | Cl | F | 1,1'-bicyclopropyl-2-yl | Cl | Cl | 1,1'-bicyclopropyl-2-yl | Cl | Br |
| 1,1'-bicyclopropyl-1-yl | Cl | F | 1,1'-bicyclopropyl-1-yl | Cl | Cl | 1,1'-bicyclopropyl-1-yl | Cl | Br |
| H | OCH$_2$CF$_3$ | F | H | OCF$_2$H | F | H | CF$_3$ | Br |
| Me | OCH$_2$CF$_3$ | F | Me | OCF$_2$H | F | Me | CF$_3$ | Br |
| t-Bu | OCH$_2$CF$_3$ | F | t-Bu | OCF$_2$H | F | t-Bu | CF$_3$ | Br |
| 1,1'-bicyclopropyl-1-yl | OCH$_2$CF$_3$ | F | 1,1'-bicyclopropyl-2-yl | OCF$_2$H | F | 1-CH$_3$-c-Pr | CF$_3$ | Br |
| H | OCH$_2$CF$_3$ | Cl | H | OCF$_2$H | Cl | 2-CH$_3$-c-Pr | CF$_3$ | Br |
| Me | OCH$_2$CF$_3$ | Cl | Me | OCF$_2$H | Cl | 1,1'-bicyclopropyl-2-yl | CF$_3$ | Br |
| t-Bu | OCH$_2$CF$_3$ | Cl | t-Bu | OCF$_2$H | Cl | 1,1'-bicyclopropyl-1-yl | CF$_3$ | Br |
| 1,1'-bicyclopropyl-1-yl | OCH$_2$CF$_3$ | Cl | 1,1'-bicyclopropyl-1-yl | OCF$_2$H | Cl | H | CF$_3$ | Cl |
| H | OCH$_2$CF$_3$ | Br | H | OCF$_2$H | Br | Me | CF$_3$ | Cl |
| Me | OCH$_2$CF$_3$ | Br | Me | OCF$_2$H | Br | t-Bu | CF$_3$ | Cl |
| t-Bu | OCH$_2$CF$_3$ | Br | t-Bu | OCF$_2$H | Br | 1-CH$_3$-c-Pr | CF$_3$ | Cl |
| 1,1'-bicyclopropyl-1-yl | OCH$_2$CF$_3$ | Br | 1,1'-bicyclopropyl-1-yl | OCF$_2$H | Br | 2-CH$_3$-c-Pr | CF$_3$ | Cl |
| H | CF$_3$ | F | 1-CH$_3$-c-Pr | CF$_3$ | F | 1,1'-bicyclopropyl-2-yl | CF$_3$ | Cl |
| Me | CF$_3$ | F | 2-CH$_3$-c-Pr | CF$_3$ | F | 1,1'-bicyclopropyl-1-yl | CF$_3$ | Cl |
| t-Bu | CF$_3$ | F | 1,1'-bicyclopropyl-2-yl | CF$_3$ | F | 1,1'-bicyclopropyl-1-yl | CF$_3$ | F |
| R$^2$ is Me, X is I, R$^{17}$ is H and Z is N. | | | R$^2$ is Me, X is I, R$^{17}$ is H and Z is N. | | | R$^2$ is Me, X is I, R$^{17}$ is H and Z is N. | | |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH$_2$ | Br | F | c-PrCH$_2$ | Br | Cl | c-PrCH$_2$ | Br | Br |
| 1-CH$_3$-c-Pr | Br | F | 1-CH$_3$-c-Pr | Br | Cl | 1-CH$_3$-c-Pr | Br | Br |
| 2-CH$_3$-c-Pr | Br | F | 2-CH$_3$-c-Pr | Br | Cl | 2-CH$_3$-c-Pr | Br | Br |
| 1,1'-bicyclopropyl-2-yl | Br | F | 1,1'-bicyclopropyl-2-yl | Br | Cl | 1,1'-bicyclopropyl-2-yl | Br | Br |
| 1,1'-bicyclopropyl-1-yl | Br | F | 1,1'-bicyclopropyl-1-yl | Br | Cl | 1,1'-bicyclopropyl-1-yl | Br | Br |
| H | Cl | F | H | Cl | Cl | H | Cl | Br |
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |

TABLE 2-continued

| | | | | | | | | |
|---|---|---|---|---|---|---|---|---|
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH$_2$ | Cl | F | c-PrCH$_2$ | Cl | Cl | c-PrCH$_2$ | Cl | Br |
| 1-CH$_3$-c-Pr | Cl | F | 1-CH$_3$-c-Pr | Cl | Cl | 1-CH$_3$-c-Pr | Cl | Br |
| 2-CH$_3$-c-Pr | Cl | F | 2-CH$_3$-c-Pr | Cl | Cl | 2-CH$_3$-c-Pr | Cl | Br |
| 1,1'-bicyclopropyl-2-yl | Cl | F | 1,1'-bicyclopropyl-2-yl | Cl | Cl | 1,1'-bicyclopropyl-2-yl | Cl | Br |
| 1,1'-bicyclopropyl-1-yl | Cl | F | 1,1'-bicyclopropyl-1-yl | Cl | Cl | 1,1'-bicyclopropyl-1-yl | Cl | Br |
| H | OCH$_2$CF$_3$ | F | H | OCF$_2$H | F | H | CF$_3$ | Br |
| Me | OCH$_2$CF$_3$ | F | Me | OCF$_2$H | F | Me | CF$_3$ | Br |
| t-Bu | OCH$_2$CF$_3$ | F | t-Bu | OCF$_2$H | F | t-Bu | CF$_3$ | Br |
| 1,1'-bicyclopropyl-1-yl | OCH$_2$CF$_3$ | F | 1,1'-bicyclopropyl-2-yl | OCF$_2$H | F | 1-CH$_3$-c-Pr | CF$_3$ | Br |
| H | OCH$_2$CF$_3$ | Cl | H | OCF$_2$H | Cl | 2-CH$_3$-c-Pr | CF$_3$ | Br |
| Me | OCH$_2$CF$_3$ | Cl | Me | OCF$_2$H | Cl | 1,1'-bicyclopropyl-2-y | CF$_3$ | Br |
| t-Bu | OCH$_2$CF$_3$ | Cl | t-Bu | OCF$_2$H | Cl | 1,1'-bicyclopropyl-1-yl | CF$_3$ | Br |
| 1,1'-bicyclopropyl-1-yl | OCH$_2$CF$_3$ | Cl | 1,1'-bicyclopropyl-1-yl | OCF$_2$H | Cl | H | CF$_3$ | Cl |
| H | OCH$_2$CF$_3$ | Br | H | OCF$_2$H | Br | Me | CF$_3$ | Cl |
| Me | OCH$_2$CF$_3$ | Br | Me | OCF$_2$H | Br | t-Bu | CF$_3$ | Cl |
| t-Bu | OCH$_2$CF$_3$ | Br | t-Bu | OCF$_2$H | Br | 1-CH$_3$-c-Pr | CF$_3$ | Cl |
| 1,1'-bicyclopropyl-1-yl | OCH$_2$CF$_3$ | Br | 1,1'-bicyclopropyl-1-yl | OCF$_2$H | Br | 2-CH$_3$-c-Pr | CF$_3$ | Cl |
| H | CF$_3$ | F | 1-CH$_3$-c-Pr | CF$_3$ | F | 1,1'-bicyclopropyl-2-yl | CF$_3$ | Cl |
| Me | CF$_3$ | F | 2-CH$_3$-c-Pr | CF$_3$ | F | 1,1'-bicyclopropyl-1-yl | CF$_3$ | Cl |
| t-Bu | CF$_3$ | F | 1,1'-bicyclopropyl-2-yl | CF$_3$ | F | 1,1'-bicyclopropyl-1-yl | CF$_3$ | F |
| R$^2$ is Cl, X is Br, R$^{17}$ is H and Z is N. | | | R$^2$ is Cl, X is Br, R$^{17}$ is H and Z is N. | | | R$^2$ is Cl, X is Br, R$^{17}$ is H and Z is N. | | |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH$_2$ | Br | F | c-PrCH$_2$ | Br | Cl | c-PrCH$_2$ | Br | Br |
| 1-CH$_3$-c-Pr | Br | F | 1-CH$_3$-c-Pr | Br | Cl | 1-CH$_3$-c-Pr | Br | Br |
| 2-CH$_3$-c-Pr | Br | F | 2-CH$_3$-c-Pr | Br | Cl | 2-CH$_3$-c-Pr | Br | Br |
| 1,1'-bicyclopropyl-2-yl | Br | F | 1,1'-bicyclopropyl-2-yl | Br | Cl | 1,1'-bicyclopropyl-2-yl | Br | Br |
| 1,1'-bicyclopropyl-1-yl | Br | F | 1,1'-bicyclopropyl-1-yl | Br | Cl | 1,1'-bicyclopropyl-1-yl | Br | Br |
| H | Cl | F | H | Cl | Cl | H | Cl | Br |
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH$_2$ | Cl | F | c-PrCH$_2$ | Cl | Cl | c-PrCH$_2$ | Cl | Br |
| 1-CH$_3$-c-Pr | Cl | F | 1-CH$_3$-c-Pr | Cl | Cl | 1-CH$_3$-c-Pr | Cl | Br |
| 2-CH$_3$-c-Pr | Cl | F | 2-CH$_3$-c-Pr | Cl | Cl | 2-CH$_3$-c-Pr | Cl | Br |
| 1,1'-bicyclopropyl-2-yl | Cl | F | 1,1'-bicyclopropyl-2-yl | Cl | Cl | 1,1'-bicyclopropyl-2-yl | Cl | Br |
| 1,1'-bicyclopropyl-1-yl | Cl | F | 1,1'-bicyclopropyl-1-yl | Cl | Cl | 1,1'-bicyclopropyl-1-yl | Cl | Br |
| H | OCH$_2$CF$_3$ | F | H | OCF$_2$H | F | H | CF$_3$ | Br |
| Me | OCH$_2$CF$_3$ | F | Me | OCF$_2$H | F | Me | CF$_3$ | Br |
| t-Bu | OCH$_2$CF$_3$ | F | t-Bu | OCF$_2$H | F | t-Bu | CF$_3$ | Br |
| 1,1'-bicyclopropyl-1-yl | OCH$_2$CF$_3$ | F | 1,1'-bicyclopropyl-2-yl | OCF$_2$H | F | 1-CH$_3$-c-Pr | CF$_3$ | Br |
| H | OCH$_2$CF$_3$ | Cl | H | OCF$_2$H | Cl | 2-CH$_3$-c-Pr | CF$_3$ | Br |
| Me | OCH$_2$CF$_3$ | Cl | Me | OCF$_2$H | Cl | 1,1'-bicyclopropyl-2-yl | CF$_3$ | Br |
| t-Bu | OCH$_2$CF$_3$ | Cl | t-Bu | OCF$_2$H | Cl | 1,1'-bicyclopropyl-1-yl | CF$_3$ | Br |
| 1,1'-bicyclopropyl-1-yl | OCH$_2$CF$_3$ | Cl | 1,1'-bicyclopropyl-1-yl | OCF$_2$H | Cl | H | CF$_3$ | Cl |
| H | OCH$_2$CF$_3$ | Br | H | OCF$_2$H | Br | Me | CF$_3$ | Cl |
| Me | OCH$_2$CF$_3$ | Br | Me | OCF$_2$H | Br | t-Bu | CF$_3$ | Cl |
| t-Bu | OCH$_2$CF$_3$ | Br | t-Bu | OCF$_2$H | Br | 1-CH$_3$-c-Pr | CF$_3$ | Cl |
| 1,1'-bicyclopropyl-1-yl | OCH$_2$CF$_3$ | Br | 1,1'-bicyclopropyl-1-yl | OCF$_2$H | Br | 2-CH$_3$-c-Pr | CF$_3$ | Cl |
| H | CF$_3$ | F | 1-CH$_3$-c-Pr | CF$_3$ | F | 1,1'-bicyclopropyl-2-yl | CF$_3$ | Cl |
| Me | CF$_3$ | F | 2-CH$_3$-c-Pr | CF$_3$ | F | 1,1'-bicyclopropyl-1-yl | CF$_3$ | Cl |
| t-Bu | CF$_3$ | F | 1,1'-bicyclopropyl-2-yl | CF$_3$ | F | 1,1'-bicyclopropyl-1-yl | CF$_3$ | F |
| R$^2$ is Cl, X is I, R$^{17}$ is H and Z is N. | | | R$^2$ is Cl, X is I, R$^{17}$ is H and Z is N. | | | R$^2$ is Cl, X is I, R$^{17}$ is H and Z is N. | | |
| H | Br | F | H | Br | Cl | H | Br | Br |
| Me | Br | F | Me | Br | Cl | Me | Br | Br |
| Et | Br | F | Et | Br | Cl | Et | Br | Br |
| n-Pr | Br | F | n-Pr | Br | Cl | n-Pr | Br | Br |
| i-Pr | Br | F | i-Pr | Br | Cl | i-Pr | Br | Br |

TABLE 2-continued

| | | | | | | | | |
|---|---|---|---|---|---|---|---|---|
| n-Bu | Br | F | n-Bu | Br | Cl | n-Bu | Br | Br |
| i-Bu | Br | F | i-Bu | Br | Cl | i-Bu | Br | Br |
| s-Bu | Br | F | s-Bu | Br | Cl | s-Bu | Br | Br |
| t-Bu | Br | F | t-Bu | Br | Cl | t-Bu | Br | Br |
| c-Pr | Br | F | c-Pr | Br | Cl | c-Pr | Br | Br |
| c-PrCH$_2$ | Br | F | c-PrCH$_2$ | Br | Cl | c-PrCH$_2$ | Br | Br |
| 1-CH$_3$-c-Pr | Br | F | 1-CH$_3$-c-Pr | Br | Cl | 1-CH$_3$-c-Pr | Br | Br |
| 2-CH$_3$-c-Pr | Br | F | 2-CH$_3$-c-Pr | Br | Cl | 2-CH$_3$-c-Pr | Br | Br |
| 1,1'-bicyclopropyl-2-yl | Br | F | 1,1'-bicyclopropyl-2-yl | Br | Cl | 1,1'-bicyclopropyl-2-yl | Br | Br |
| 1,1'-bicyclopropyl-1-yl | Br | F | 1,1'-bicyclopropyl-1-yl | Br | Cl | 1,1'-bicyclopropyl-1-yl | Br | Br |
| H | Cl | F | H | Cl | Cl | H | Cl | Br |
| Me | Cl | F | Me | Cl | Cl | Me | Cl | Br |
| Et | Cl | F | Et | Cl | Cl | Et | Cl | Br |
| n-Pr | Cl | F | n-Pr | Cl | Cl | n-Pr | Cl | Br |
| i-Pr | Cl | F | i-Pr | Cl | Cl | i-Pr | Cl | Br |
| n-Bu | Cl | F | n-Bu | Cl | Cl | n-Bu | Cl | Br |
| i-Bu | Cl | F | i-Bu | Cl | Cl | i-Bu | Cl | Br |
| s-Bu | Cl | F | s-Bu | Cl | Cl | s-Bu | Cl | Br |
| t-Bu | Cl | F | t-Bu | Cl | Cl | t-Bu | Cl | Br |
| c-Pr | Cl | F | c-Pr | Cl | Cl | c-Pr | Cl | Br |
| c-PrCH$_2$ | Cl | F | c-PrCH$_2$ | Cl | Cl | c-PrCH$_2$ | Cl | Br |
| 1-CH$_3$-c-Pr | Cl | F | 1-CH$_3$-c-Pr | Cl | Cl | 1-CH$_3$-c-Pr | Cl | Br |
| 2-CH$_3$-c-Pr | Cl | F | 2-CH$_3$-c-Pr | Cl | Cl | 2-CH$_3$-c-Pr | Cl | Br |
| 1,1'-bicyclopropyl-2-yl | Cl | F | 1,1'-bicyclopropyl-2-yl | Cl | Cl | 1,1'-bicyclopropyl-2-yl | Cl | Br |
| 1,1'-bicyclopropyl-1-yl | Cl | F | 1,1'-bicyclopropyl-1-yl | Cl | Cl | 1,1'-bicyclopropyl-1-yl | Cl | Br |
| H | OCH$_2$CF$_3$ | F | H | OCF$_2$H | F | H | CF$_3$ | Br |
| Me | OCH$_2$CF$_3$ | F | Me | OCF$_2$H | F | Me | CF$_3$ | Br |
| t-Bu | OCH$_2$CF$_3$ | F | t-Bu | OCF$_2$H | F | t-Bu | CF$_3$ | Br |
| 1,1'-bicyclopropyl-1-yl | OCH$_2$CF$_3$ | F | 1,1'-bicyclopropyl-2-yl | OCF$_2$H | F | 1-CH$_3$-c-Pr | CF$_3$ | Br |
| H | OCH$_2$CF$_3$ | Cl | H | OCF$_2$H | Cl | 2-CH$_3$-c-Pr | CF$_3$ | Br |
| Me | OCH$_2$CF$_3$ | Cl | Me | OCF$_2$H | Cl | 1,1'-bicyclopropyl-2-yl | CF$_3$ | Br |
| t-Bu | OCH$_2$CF$_3$ | Cl | t-Bu | OCF$_2$H | Cl | 1,1'-bicyclopropyl-1-yl | CF$_3$ | Br |
| 1,1'-bicyclopropyl-1-yl | OCH$_2$CF$_3$ | Cl | 1,1'-bicyclopropyl-2-yl | OCF$_2$H | Cl | H | CF$_3$ | Cl |
| H | OCH$_2$CF$_3$ | Br | H | OCF$_2$H | Br | Me | CF$_3$ | Cl |
| Me | OCH$_2$CF$_3$ | Br | Me | OCF$_2$H | Br | t-Bu | CF$_3$ | Cl |
| t-Bu | OCH$_2$CF$_3$ | Br | t-Bu | OCF$_2$H | Br | 1-CH$_3$-c-Pr | CF$_3$ | Cl |
| 1,1'-bicyclopropyl-1-yl | OCH$_2$CF$_3$ | Br | 1,1'-bicyclopropyl-1-yl | OCF$_2$H | Br | 2-CH$_3$-c-Pr | CF$_3$ | Cl |
| H | CF$_3$ | F | 1-CH$_3$-c-Pr | CF$_3$ | F | 1,1'-bicyclopropyl-2-yl | CF$_3$ | Cl |
| Me | CF$_3$ | F | 2-CH$_3$-c-Pr | CF$_3$ | F | 1,1'-bicyclopropyl-1-yl | CF$_3$ | Cl |
| t-Bu | CF$_3$ | F | 1,1'-bicyclopropyl-2-yl | CF$_3$ | F | 1,1'-bicyclopropyl-1-yl | CF$_3$ | F |
| R$^2$ is Me, X is Br, R$^{17}$ is H and Z is CH. | | | R$^2$ is Me, X is Br, R$^{17}$ is H and Z is CH. | | | R$^2$ is Me, X is Br, R$^{17}$ is H and Z is CH. | | |
| H | Br | F | Me | OCF$_2$H | F | H | Br | Br |
| Me | Br | F | Et | OCF$_2$H | F | Me | Br | Br |
| t-Bu | Br | F | c-PrCH$_2$ | OCF$_2$H | F | t-Bu | Br | Br |
| c-Pr | Br | F | c-Pr | OCF$_2$H | Cl | c-Pr | Br | Br |
| c-PrCH$_2$ | Br | F | c-PrCH$_2$ | OCF$_2$H | Cl | c-PrCH$_2$ | Br | Br |
| 1,1'-bicyclopropyl-2-yl | Br | F | 1,1'-bicyclopropyl-2-yl | OCF$_2$H | Cl | 1,1'-bicyclopropyl-2-yl | Br | Br |
| 1,1'-bicyclopropyl-1-yl | Br | F | Me | OCF$_2$H | Br | 1,1'-bicyclopropyl-1-yl | Br | Br |
| H | Cl | F | Et | OCF$_2$H | Br | H | Cl | Cl |
| Me | Cl | F | Me | OCH$_2$CF$_3$ | F | Me | Cl | Cl |
| t-Bu | Cl | F | Et | OCH$_2$CF$_3$ | F | t-Bu | Cl | Cl |
| c-Pr | Cl | F | c-Pr | OCH$_2$CF$_3$ | F | c-Pr | Cl | Cl |
| c-PrCH$_2$ | Cl | F | c-PrCH$_2$ | OCH$_2$CF$_3$ | Cl | c-PrCH$_2$ | Cl | Cl |
| 1,1'-bicyclopropyl-2-yl | Cl | F | 1,1'-bicyclopropyl-2-yl | OCH$_2$CF$_3$ | Cl | 1,1'-bicyclopropyl-2-yl | Cl | Cl |
| 1,1'-bicyclopropyl-1-yl | Cl | F | Me | OCH$_2$CF$_3$ | Br | 1,1'-bicyclopropyl-1-yl | Cl | Cl |
| H | Cl | Br | Et | OCH$_2$CF$_3$ | Br | Et | CF$_3$ | Br |
| Me | Cl | Br | H | Br | Cl | c-Pr | CF$_3$ | Br |
| t-Bu | Cl | Br | Me | Br | Cl | c-PrCH$_2$ | CF$_3$ | Br |
| c-Pr | Cl | Br | t-Bu | Br | Cl | 1,1'-bicyclopropyl-2-yl | CF$_3$ | Br |
| c-PrCH$_2$ | Cl | Br | c-Pr | Br | Cl | H | CF$_3$ | Cl |
| 1,1'-bicyclopropyl-2-yl | Cl | Br | c-PrCH$_2$ | Br | Cl | Me | CF$_3$ | Cl |
| 1,1'-bicyclopropyl-1-yl | Cl | Br | 1,1'-bicyclopropyl-2-yl | Br | Cl | t-Bu | CF$_3$ | Cl |
| H | CF$_3$ | F | 1,1'-bicyclopropyl-1-yl | Br | Cl | Me | CF$_3$ | Cl |
| Me | CF$_3$ | F | t-Bu | CF$_3$ | F | 2-CH$_3$-c-Pr | CF$_3$ | F |
| R$^2$ is Me, X is Cl, R$^{17}$ is H and Z is CH. | | | R$^2$ is Me, X is Cl, R$^{17}$ is H and Z is CH. | | | R$^2$ is Me, X is Cl, R$^{17}$ is H and Z is CH. | | |
| H | Br | F | Me | OCF$_2$H | F | H | Br | Br |
| Me | Br | F | Et | OCF$_2$H | F | Me | Br | Br |
| t-Bu | Br | F | c-PrCH$_2$ | OCF$_2$H | F | t-Bu | Br | Br |
| c-Pr | Br | F | c-Pr | OCF$_2$H | Cl | c-Pr | Br | Br |
| c-PrCH$_2$ | Br | F | c-PrCH$_2$ | OCF$_2$H | Cl | c-PrCH$_2$ | Br | Br |
| 1,1'-bicyclopropyl-2-yl | Br | F | 1,1'-bicyclopropyl-2-yl | OCF$_2$H | Cl | 1,1'-bicyclopropyl-2-yl | Br | Br |
| 1,1'-bicyclopropyl-1-yl | Br | F | Me | OCF$_2$H | Br | 1,1'-bicyclopropyl-1-yl | Br | Br |
| H | Cl | F | Et | OCF$_2$H | Br | H | Cl | Cl |
| Me | Cl | F | Me | OCH$_2$CF$_3$ | F | Me | Cl | Cl |
| t-Bu | Cl | F | Et | OCH$_2$CF$_3$ | F | t-Bu | Cl | Cl |
| c-Pr | Cl | F | c-Pr | OCH$_2$CF$_3$ | F | c-Pr | Cl | Cl |
| c-PrCH$_2$ | Cl | F | c-PrCH$_2$ | OCH$_2$CF$_3$ | Cl | c-PrCH$_2$ | Cl | Cl |

TABLE 2-continued

| | | | | | | | | |
|---|---|---|---|---|---|---|---|---|
| 1,1'-bicyclopropyl-2-yl | Cl | F | 1,1'-bicyclopropyl-2-yl | OCH$_2$CF$_3$ | Cl | 1,1'-bicyclopropyl-2-yl | Cl | Cl |
| 1,1'-bicyclopropyl-1-yl | Cl | F | Me | OCH$_2$CF$_3$ | Br | 1,1'-bicyclopropyl-1-yl | Cl | Cl |
| H | Cl | Br | Et | OCH$_2$CF$_3$ | Br | Et | CF$_3$ | Br |
| Me | Cl | Br | H | Br | Cl | c-Pr | CF$_3$ | Br |
| t-Bu | Cl | Br | Me | Br | Cl | c-PrCH$_2$ | CF$_3$ | Br |
| c-Pr | Cl | Br | t-Bu | Br | Cl | 1,1'-bicyclopropyl-2-yl | CF$_3$ | Br |
| c-PrCH$_2$ | Cl | Br | c-Pr | Br | Cl | H | CF$_3$ | Cl |
| 1,1'-bicyclopropyl-2-yl | Cl | Br | c-PrCH$_2$ | Br | Cl | Me | CF$_3$ | Cl |
| 1,1'-bicyclopropyl-1-yl | Cl | Br | 1,1'-bicyclopropyl-2-yl | Br | Cl | t-Bu | CF$_3$ | Cl |
| H | CF$_3$ | F | 1,1'-bicyclopropyl-1-yl | Br | Cl | Me | CF$_3$ | Cl |
| Me | CF$_3$ | F | t-Bu | CF$_3$ | F | 2-CH$_3$-c-Pr | CF$_3$ | F |

$R^2$ is Me, X is I, $R^{17}$ is H and Z is CH.  $R^2$ is Me, X is I, $R^{17}$ is H and Z is CH.  $R^2$ is Me, X is I, $R^{17}$ is H and Z is CH.

| | | | | | | | | |
|---|---|---|---|---|---|---|---|---|
| H | Br | F | Me | OCF$_2$H | F | H | Br | Br |
| Me | Br | F | Et | OCF$_2$H | F | Me | Br | Br |
| t-Bu | Br | F | c-PrCH$_2$ | OCF$_2$H | F | t-Bu | Br | Br |
| c-Pr | Br | F | c-Pr | OCF$_2$H | Cl | c-Pr | Br | Br |
| c-PrCH$_2$ | Br | F | c-PrCH$_2$ | OCF$_2$H | Cl | c-PrCH$_2$ | Br | Br |
| 1,1'-bicyclopropyl-2-yl | Br | F | 1,1'-bicyclopropyl-2-yl | OCF$_2$H | Cl | 1,1'-bicyclopropyl-2-yl | Br | Br |
| 1,1'-bicyclopropyl-1-yl | Br | F | Me | OCF$_2$H | Br | 1,1'-bicyclopropyl-1-yl | Br | Br |
| H | Cl | F | Et | OCF$_2$H | Br | H | Cl | Cl |
| Me | Cl | F | Me | OCH$_2$CF$_3$ | F | Me | Cl | Cl |
| t-Bu | Cl | F | Et | OCH$_2$CF$_3$ | F | t-Bu | Cl | Cl |
| c-Pr | Cl | F | c-Pr | OCH$_2$CF$_3$ | F | c-Pr | Cl | Cl |
| c-PrCH$_2$ | Cl | F | c-PrCH$_2$ | OCH$_2$CF$_3$ | Cl | c-PrCH$_2$ | Cl | Cl |
| 1,1'-bicyclopropyl-2-yl | Cl | F | 1,1'-bicyclopropyl-2-yl | OCH$_2$CF$_3$ | Cl | 1,1'-bicyclopropyl-2-yl | Cl | Cl |
| 1,1'-bicyclopropyl-1-yl | Cl | F | Me | OCH$_2$CF$_3$ | Br | 1,1'-bicyclopropyl-1-yl | Cl | Cl |
| H | Cl | Br | Et | OCH$_2$CF$_3$ | Br | Et | CF$_3$ | Br |
| Me | Cl | Br | H | Br | Cl | c-Pr | CF$_3$ | Br |
| t-Bu | Cl | Br | Me | Br | Cl | c-PrCH$_2$ | CF$_3$ | Br |
| c-Pr | Cl | Br | t-Bu | Br | Cl | 1,1'-bicyclopropyl-2-yl | CF$_3$ | Br |
| c-PrCH$_2$ | Cl | Br | c-Pr | Br | Cl | H | CF$_3$ | Cl |
| 1,1'-bicyclopropyl-2-yl | Cl | Br | c-PrCH$_2$ | Br | Cl | Me | CF$_3$ | Cl |
| 1,1'-bicyclopropyl-1-yl | Cl | Br | 1,1'-bicyclopropyl-2-yl | Br | Cl | t-Bu | CF$_3$ | Cl |
| H | CF$_3$ | F | 1,1'-bicyclopropyl-1-yl | Br | Cl | Me | CF$_3$ | Cl |
| Me | CF$_3$ | F | t-Bu | CF$_3$ | F | 2-CH$_3$-c-Pr | CF$_3$ | F |

$R^2$ is Cl, X is Br, $R^{17}$ is H and Z is CH.  $R^2$ is Cl, X is Br, $R^{17}$ is H and Z is CH.  $R^2$ is Cl, X is Br, $R^{17}$ is H and Z is CH.

| | | | | | | | | |
|---|---|---|---|---|---|---|---|---|
| H | Br | F | Me | OCF$_2$H | F | H | Br | Br |
| Me | Br | F | Et | OCF$_2$H | F | Me | Br | Br |
| t-Bu | Br | F | c-PrCH$_2$ | OCF$_2$H | F | t-Bu | Br | Br |
| c-Pr | Br | F | c-Pr | OCF$_2$H | Cl | c-Pr | Br | Br |
| c-PrCH$_2$ | Br | F | c-PrCH$_2$ | OCF$_2$H | Cl | c-PrCH$_2$ | Br | Br |
| 1,1'-bicyclopropyl-2-yl | Br | F | 1,1'-bicyclopropyl-2-yl | OCF$_2$H | Cl | 1,1'-bicyclopropyl-2-yl | Br | Br |
| 1,1'-bicyclopropyl-1-yl | Br | F | Me | OCF$_2$H | Br | 1,1'-bicyclopropyl-1-yl | Br | Br |
| H | Cl | F | Et | OCF$_2$H | Br | H | Cl | Cl |
| Me | Cl | F | Me | OCH$_2$CF$_3$ | F | Me | Cl | Cl |
| t-Bu | Cl | F | Et | OCH$_2$CF$_3$ | F | t-Bu | Cl | Cl |
| c-Pr | Cl | F | c-Pr | OCH$_2$CF$_3$ | F | c-Pr | Cl | Cl |
| c-PrCH$_2$ | Cl | F | c-PrCH$_2$ | OCH$_2$CF$_3$ | Cl | c-PrCH$_2$ | Cl | Cl |
| 1,1'-bicyclopropyl-2-yl | Cl | F | 1,1'-bicyclopropyl-2-yl | OCH$_2$CF$_3$ | Cl | 1,1'-bicyclopropyl-2-yl | Cl | Cl |
| 1,1'-bicyclopropyl-1-yl | Cl | F | Me | OCH$_2$CF$_3$ | Br | 1,1'-bicyclopropyl-1-yl | Cl | Cl |
| H | Cl | Br | Et | OCH$_2$CF$_3$ | Br | Et | CF$_3$ | Br |
| Me | Cl | Br | H | Br | Cl | c-Pr | CF$_3$ | Br |
| t-Bu | Cl | Br | Me | Br | Cl | c-PrCH$_2$ | CF$_3$ | Br |
| c-Pr | Cl | Br | t-Bu | Br | Cl | 1,1'-bicyclopropyl-2-yl | CF$_3$ | Br |
| c-PrCH$_2$ | Cl | Br | c-Pr | Br | Cl | H | CF$_3$ | Cl |
| 1,1'-bicyclopropyl-2-yl | Cl | Br | c-PrCH$_2$ | Br | Cl | Me | CF$_3$ | Cl |
| 1,1'-bicyclopropyl-1-yl | Cl | Br | 1,1'-bicyclopropyl-2-yl | Br | Cl | t-Bu | CF$_3$ | Cl |
| H | CF$_3$ | F | 1,1'-bicyclopropyl-1-yl | Br | Cl | Me | CF$_3$ | Cl |
| Me | CF$_3$ | F | t-Bu | CF$_3$ | F | 2-CH$_3$-c-Pr | CF$_3$ | F |

$R^2$ is Cl, X is I, $R^{17}$ is H and Z is CH.  $R^2$ is Cl, X is I, $R^{17}$ is H and Z is CH.  $R^2$ is Cl, X is I, $R^{17}$ is H and Z is CH.

| | | | | | | | | |
|---|---|---|---|---|---|---|---|---|
| H | Br | F | Me | OCF$_2$H | F | H | Br | Br |
| Me | Br | F | Et | OCF$_2$H | F | Me | Br | Br |
| t-Bu | Br | F | c-PrCH$_2$ | OCF$_2$H | F | t-Bu | Br | Br |
| c-Pr | Br | F | c-Pr | OCF$_2$H | Cl | c-Pr | Br | Br |
| c-PrCH$_2$ | Br | F | c-PrCH$_2$ | OCF$_2$H | Cl | c-PrCH$_2$ | Br | Br |
| 1,1'-bicyclopropyl-2-yl | Br | F | 1,1'-bicyclopropyl-2-yl | OCF$_2$H | Cl | 1,1'-bicyclopropyl-2-yl | Br | Br |
| 1,1'-bicyclopropyl-1-yl | Br | F | Me | OCF$_2$H | Br | 1,1'-bicyclopropyl-1-yl | Br | Br |
| H | Cl | F | Et | OCF$_2$H | Br | H | Cl | Cl |
| Me | Cl | F | Me | OCH$_2$CF$_3$ | F | Me | Cl | Cl |
| t-Bu | Cl | F | Et | OCH$_2$CF$_3$ | F | t-Bu | Cl | Cl |
| c-Pr | Cl | F | c-Pr | OCH$_2$CF$_3$ | F | c-Pr | Cl | Cl |
| c-PrCH$_2$ | Cl | F | c-PrCH$_2$ | OCH$_2$CF$_3$ | Cl | c-PrCH$_2$ | Cl | Cl |
| 1,1'-bicyclopropyl-2-yl | Cl | F | 1,1'-bicyclopropyl-2-yl | OCH$_2$CF$_3$ | Cl | 1,1'-bicyclopropyl-2-yl | Cl | Cl |
| 1,1'-bicyclopropyl-1-yl | Cl | F | Me | OCH$_2$CF$_3$ | Br | 1,1'-bicyclopropyl-1-yl | Cl | Cl |
| H | Cl | Br | Et | OCH$_2$CF$_3$ | Br | Et | CF$_3$ | Br |
| Me | Cl | Br | H | Br | Cl | c-Pr | CF$_3$ | Br |
| t-Bu | Cl | Br | Me | Br | Cl | c-PrCH$_2$ | CF$_3$ | Br |

TABLE 2-continued

| | | | | | | | | |
|---|---|---|---|---|---|---|---|---|
| c-Pr | Cl | Br | t-Bu | Br | Cl | 1,1'-bicyclopropyl-2-yl | CF₃ | Br |
| c-PrCH₂ | Cl | Br | c-Pr | Br | Cl | H | CF₃ | Cl |
| 1,1'-bicyclopropyl-2-yl | Cl | Br | c-PrCH₂ | Br | Cl | Me | CF₃ | Cl |
| 1,1'-bicyclopropyl-1-yl | Cl | Br | 1,1'-bicyclopropyl-2-yl | Br | Cl | t-Bu | CF₃ | Cl |
| H | CF₃ | F | 1,1'-bicyclopropyl-1-yl | Br | Cl | Me | CF₃ | Cl |
| Me | CF₃ | F | t-Bu | CF₃ | F | 2-CH₃-c-Pr | CF₃ | F |

R² is Me, X is Br, R¹⁷ is F and Z is N.    R² is Me, X is Br, R¹⁷ is F and Z is N.    R² is Me, X is Br, R¹⁷ is F and Z is N.

| | | | | | | | | |
|---|---|---|---|---|---|---|---|---|
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH₂ | Br | F | c-PrCH₂ | Cl | Cl | c-PrCH₂ | Br | Br |
| 1,1'-bicyclopropyl-2-yl | Br | F | 1,1'-bicyclopropyl-1-yl | Cl | Cl | 1,1'-bicyclopropyl-1-yl | Br | Br |
| 1,1'-bicyclopropyl-1-yl | Br | F | Me | OCF₂H | F | H | Cl | Br |
| H | Cl | F | Et | OCF₂H | F | Me | Cl | Br |
| Me | Cl | F | c-Pr | OCF₂H | Cl | t-Bu | Cl | Br |
| t-Bu | Cl | F | c-PrCH₂ | OCF₂H | Cl | c-Pr | Cl | Br |
| c-Pr | Cl | F | 1,1'-bicyclopropyl-1-yl | OCF₂H | Cl | c-PrCH₂ | Cl | Br |
| c-PrCH₂ | Cl | F | Me | OCF₂H | Br | 1,1'-bicyclopropyl-2-yl | Cl | Br |
| 1,1'-bicyclopropyl-2-yl | Cl | F | Et | OCF₂H | Br | 1,1'-bicyclopropyl-1-yl | Cl | Br |
| H | Br | Cl | Me | OCH₂CF₃ | F | H | CF₃ | F |
| Me | Br | Cl | Et | OCH₂CF₃ | F | Me | CF₃ | F |
| t-Bu | Br | Cl | c-Pr | OCH₂CF₃ | Cl | t-Bu | CF₃ | F |
| c-Pr | Br | Cl | c-PrCH₂ | OCH₂CF₃ | Cl | 2-CH₃-c-Pr | CF₃ | F |
| c-PrCH₂ | Br | Cl | 1,1'-bicyclopropyl-1-yl | OCH₂CF₃ | Cl | 1,1'-bicyclopropyl-2-yl | CF₃ | F |
| 1,1'-bicyclopropyl-1-yl | Br | Cl | Me | OCH₂CF₃ | Br | Et | CF₃ | Br |
| H | CF₃ | Cl | Et | OCH₂CF₃ | Br | c-Pr | CF₃ | Br |
| Me | CF₃ | Cl | 1,1'-bicyclopropyl-2-yl | CF₃ | Cl | c-PrCH₂ | CF₃ | Br |
| t-Bu | CF₃ | Cl | Me | CF₃ | Br | 1,1'-bicyclopropyl-2-yl | CF₃ | Br |

R² is Me, X is Cl, R¹⁷ is F and Z is N.    R² is Me, X is Cl, R¹⁷ is F and Z is N.    R² is Me, X is Cl, R¹⁷ is F and Z is N.

| | | | | | | | | |
|---|---|---|---|---|---|---|---|---|
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH₂ | Br | F | c-PrCH₂ | Cl | Cl | c-PrCH₂ | Br | Br |
| 1,1'-bicyclopropyl-2-yl | Br | F | 1,1'-bicyclopropyl-1-yl | Cl | Cl | 1,1'-bicyclopropyl-1-yl | Br | Br |
| 1,1'-bicyclopropyl-1-yl | Br | F | Me | OCF₂H | F | H | Cl | Br |
| H | Cl | F | Et | OCF₂H | F | Me | Cl | Br |
| Me | Cl | F | c-Pr | OCF₂H | Cl | t-Bu | Cl | Br |
| t-Bu | Cl | F | c-PrCH₂ | OCF₂H | Cl | c-Pr | Cl | Br |
| c-Pr | Cl | F | 1,1'-bicyclopropyl-1-yl | OCF₂H | Cl | c-PrCH₂ | Cl | Br |
| c-PrCH₂ | Cl | F | Me | OCF₂H | Br | 1,1'-bicyclopropyl-2-yl | Cl | Br |
| 1,1'-bicyclopropyl-2-yl | Cl | F | Et | OCF₂H | Br | 1,1'-bicyclopropyl-1-yl | Cl | Br |
| H | Br | Cl | Me | OCH₂CF₃ | F | H | CF₃ | F |
| Me | Br | Cl | Et | OCH₂CF₃ | F | Me | CF₃ | F |
| t-Bu | Br | Cl | c-Pr | OCH₂CF₃ | Cl | t-Bu | CF₃ | F |
| c-Pr | Br | Cl | c-PrCH₂ | OCH₂CF₃ | Cl | 2-CH₃-c-Pr | CF₃ | F |
| c-PrCH₂ | Br | Cl | 1,1'-bicyclopropyl-1-yl | OCH₂CF₃ | Cl | 1,1'-bicyclopropyl-2-yl | CF₃ | F |
| 1,1'-bicyclopropyl-1-yl | Br | Cl | Me | OCH₂CF₃ | Br | Et | CF₃ | Br |
| H | CF₃ | Cl | Et | OCH₂CF₃ | Br | c-Pr | CF₃ | Br |
| Me | CF₃ | Cl | 1,1'-bicyclopropyl-2-yl | CF₃ | Cl | c-PrCH₂ | CF₃ | Br |
| t-Bu | CF₃ | Cl | Me | CF₃ | Br | 1,1'-bicyclopropyl-2-yl | CF₃ | Br |

R² is Me, X is I, R¹⁷ is F and Z is N.    R² is Me, X is I, R¹⁷ is F and Z is N.    R² is Me, X is I, R¹⁷ is F and Z is N.

| | | | | | | | | |
|---|---|---|---|---|---|---|---|---|
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH₂ | Br | F | c-PrCH₂ | Cl | Cl | c-PrCH₂ | Br | Br |
| 1,1'-bicyclopropyl-2-yl | Br | F | 1,1'-bicyclopropyl-1-yl | Cl | Cl | 1,1'-bicyclopropyl-1-yl | Br | Br |
| 1,1'-bicyclopropyl-1-yl | Br | F | Me | OCF₂H | F | H | Cl | Br |
| H | Cl | F | Et | OCF₂H | F | Me | Cl | Br |
| Me | Cl | F | c-Pr | OCF₂H | Cl | t-Bu | Cl | Br |
| t-Bu | Cl | F | c-PrCH₂ | OCF₂H | Cl | c-Pr | Cl | Br |
| c-Pr | Cl | F | 1,1'-bicyclopropyl-1-yl | OCF₂H | Cl | c-PrCH₂ | Cl | Br |
| c-PrCH₂ | Cl | F | Me | OCF₂H | Br | 1,1'-bicyclopropyl-2-yl | Cl | Br |
| 1,1'-bicyclopropyl-2-yl | Cl | F | Et | OCF₂H | Br | 1,1'-bicyclopropyl-1-yl | Cl | Br |
| H | Br | Cl | Me | OCH₂CF₃ | F | H | CF₃ | F |
| Me | Br | Cl | Et | OCH₂CF₃ | F | Me | CF₃ | F |
| t-Bu | Br | Cl | c-Pr | OCH₂CF₃ | Cl | t-Bu | CF₃ | F |
| c-Pr | Br | Cl | c-PrCH₂ | OCH₂CF₃ | Cl | 2-CH₃-c-Pr | CF₃ | F |
| c-PrCH₂ | Br | Cl | 1,1'-bicyclopropyl-1-yl | OCH₂CF₃ | Cl | 1,1'-bicyclopropyl-2-yl | CF₃ | F |
| 1,1'-bicyclopropyl-1-yl | Br | Cl | Me | OCH₂CF₃ | Br | Et | CF₃ | Br |
| H | CF₃ | Cl | Et | OCH₂CF₃ | Br | c-Pr | CF₃ | Br |

TABLE 2-continued

| | | | | | | | | | |
|---|---|---|---|---|---|---|---|---|---|
| Me | $CF_3$ | Cl | Me | $CF_3$ | Br | c-PrCH$_2$ | $CF_3$ | Br | |
| t-Bu | $CF_3$ | Cl | 1,1'-bicyclopropyl-2-yl | $CF_3$ | Cl | 1,1'-bicyclopropyl-2-yl | $CF_3$ | Br | |
| $R^2$ is Cl, X is Br, $R^{17}$ is F and Z is N. | | | $R^2$ is Cl, X is Br, $R^{17}$ is F and Z is N. | | | $R^2$ is Cl, X is Br, $R^{17}$ is F and Z is N. | | | |
| H | Br | F | H | Cl | Cl | H | Br | Br | |
| Me | Br | F | Me | Cl | Cl | Me | Br | Br | |
| t-Bu | Br | F | t-Bu | Cl | Cl | t-Bu | Br | Br | |
| c-Pr | Br | F | c-Pr | Cl | Cl | c-Pr | Br | Br | |
| c-PrCH$_2$ | Br | F | c-PrCH$_2$ | Cl | Cl | c-PrCH$_2$ | Br | Br | |
| 1,1'-bicyclopropyl-2-yl | Br | F | 1,1'-bicyclopropyl-1-yl | Cl | Cl | 1,1'-bicyclopropyl-1-yl | Br | Br | |
| 1,1'-bicyclopropyl-1-yl | Br | F | Me | OCF$_2$H | F | H | Cl | Br | |
| H | Cl | F | Et | OCF$_2$H | F | Me | Cl | Br | |
| Me | Cl | F | c-Pr | OCF$_2$H | Cl | t-Bu | Cl | Br | |
| t-Bu | Cl | F | c-PrCH$_2$ | OCF$_2$H | Cl | c-Pr | Cl | Br | |
| c-Pr | Cl | F | 1,1'-bicyclopropyl-1-yl | OCF$_2$H | Cl | c-PrCH$_2$ | Cl | Br | |
| c-PrCH$_2$ | Cl | F | Me | OCF$_2$H | Br | 1,1'-bicyclopropyl-2-yl | Cl | Br | |
| 1,1'-bicyclopropyl-2-yl | Cl | F | Et | OCF$_2$H | Br | 1,1'-bicyclopropyl-1-yl | Cl | Br | |
| H | Br | Cl | Me | OCH$_2$CF$_3$ | F | H | $CF_3$ | F | |
| Me | Br | Cl | Et | OCH$_2$CF$_3$ | F | Me | $CF_3$ | F | |
| t-Bu | Br | Cl | c-Pr | OCH$_2$CF$_3$ | Cl | t-Bu | $CF_3$ | F | |
| c-Pr | Br | Cl | c-PrCH$_2$ | OCH$_2$CF$_3$ | Cl | 2-CH$_3$-c-Pr | $CF_3$ | F | |
| c-PrCH$_2$ | Br | Cl | 1,1'-bicyclopropyl-1-yl | OCH$_2$CF$_3$ | Cl | 1,1'-bicyclopropyl-2-yl | $CF_3$ | F | |
| 1,1'-bicyclopropyl-1-yl | Br | Cl | Me | OCH$_2$CF$_3$ | Br | Et | $CF_3$ | Br | |
| H | $CF_3$ | Cl | Et | OCH$_2$CF$_3$ | Br | c-Pr | $CF_3$ | Br | |
| Me | $CF_3$ | Cl | 1,1'-bicyclopropyl-2-yl | $CF_3$ | Cl | c-PrCH$_2$ | $CF_3$ | Br | |
| t-Bu | $CF_3$ | Cl | Me | $CF_3$ | Br | 1,1'-bicyclopropyl-2-yl | $CF_3$ | Br | |
| $R^2$ is Cl, X is I, $R^{17}$ is F and Z is N. | | | $R^2$ is Cl, X is I, $R^{17}$ is F and Z is N. | | | $R^2$ is Cl, X is I, $R^{17}$ is F and Z is N. | | | |
| H | Br | F | H | Cl | Cl | H | Br | Br | |
| Me | Br | F | Me | Cl | Cl | Me | Br | Br | |
| t-Bu | Br | F | t-Bu | Cl | Cl | t-Bu | Br | Br | |
| c-Pr | Br | F | c-Pr | Cl | Cl | c-Pr | Br | Br | |
| c-PrCH$_2$ | Br | F | c-PrCH$_2$ | Cl | Cl | c-PrCH$_2$ | Br | Br | |
| 1,1'-bicyclopropyl-2-yl | Br | F | 1,1'-bicyclopropyl-1-yl | Cl | Cl | 1,1'-bicyclopropyl-1-yl | Br | Br | |
| 1,1'-bicyclopropyl-1-yl | Br | F | Me | OCF$_2$H | F | H | Cl | Br | |
| H | Cl | F | Et | OCF$_2$H | F | Me | Cl | Br | |
| Me | Cl | F | c-PrCH$_2$ | OCF$_2$H | Cl | t-Bu | Cl | Br | |
| t-Bu | Cl | F | c-PrCH$_2$ | OCF$_2$H | Cl | c-Pr | Cl | Br | |
| c-Pr | Cl | F | 1,1'-bicyclopropyl-1-yl | OCF$_2$H | Cl | c-PrCH$_2$ | Cl | Br | |
| c-PrCH$_2$ | Cl | F | Me | OCF$_2$H | Br | 1,1'-bicyclopropyl-2-yl | Cl | Br | |
| 1,1'-bicyclopropyl-2-yl | Cl | F | Et | OCF$_2$H | Br | 1,1'-bicyclopropyl-1-yl | Cl | Br | |
| H | Br | Cl | Me | OCH$_2$CF$_3$ | F | H | $CF_3$ | F | |
| Me | Br | Cl | Et | OCH$_2$CF$_3$ | F | Me | $CF_3$ | F | |
| t-Bu | Br | Cl | c-Pr | OCH$_2$CF$_3$ | Cl | t-Bu | $CF_3$ | F | |
| c-Pr | Br | Cl | c-PrCH$_2$ | OCH$_2$CF$_3$ | Cl | 2-CH$_3$-c-Pr | $CF_3$ | F | |
| c-PrCH$_2$ | Br | Cl | 1,1'-bicyclopropyl-1-yl | OCH$_2$CF$_3$ | Cl | 1,1'-bicyclopropyl-2-yl | $CF_3$ | F | |
| 1,1'-bicyclopropyl-1-yl | Br | Cl | Me | OCH$_2$CF$_3$ | Br | Et | $CF_3$ | Br | |
| H | $CF_3$ | Cl | Et | OCH$_2$CF$_3$ | Br | c-Pr | $CF_3$ | Br | |
| Me | $CF_3$ | Cl | 1,1'-bicyclopropyl-2-yl | $CF_3$ | Cl | c-PrCH$_2$ | $CF_3$ | Br | |
| t-Bu | $CF_3$ | Cl | Me | $CF_3$ | Br | 1,1'-bicyclopropyl-2-yl | $CF_3$ | Br | |
| $R^2$ is Me, X is Br, $R^{17}$ is Cl and Z is N. | | | $R^2$ is Me, X is Br, $R^{17}$ is Cl and Z is N. | | | $R^2$ is Me, X is Br, $R^{17}$ is Cl and Z | | | |
| H | Br | F | H | Cl | Cl | H | Br | Br | |
| Me | Br | F | Me | Cl | Cl | Me | Br | Br | |
| t-Bu | Br | F | t-Bu | Cl | Cl | t-Bu | Br | Br | |
| c-Pr | Br | F | c-Pr | Cl | Cl | c-Pr | Br | Br | |
| c-PrCH$_2$ | Br | F | c-PrCH$_2$ | Cl | Cl | c-PrCH$_2$ | Br | Br | |
| 1,1'-bicyclopropyl-2-yl | Br | F | 1,1'-bicyclopropyl-2-yl | Cl | Cl | 1,1'-bicyclopropyl-1-yl | Br | Br | |
| 1,1'-bicyclopropyl-1-yl | Br | F | 1,1'-bicyclopropyl-1-yl | Cl | Cl | H | Cl | Br | |
| H | Cl | F | Me | OCH$_2$CF$_3$ | F | Me | Cl | Br | |
| Me | Cl | F | Et | OCH$_2$CF$_3$ | F | t-Bu | Cl | Br | |
| t-Bu | Cl | F | c-Pr | OCH$_2$CF$_3$ | Cl | c-Pr | Cl | Br | |
| c-Pr | Cl | F | c-PrCH$_2$ | OCH$_2$CF$_3$ | Cl | c-PrCH$_2$ | Cl | Br | |
| c-PrCH$_2$ | Cl | F | 1,1'-bicyclopropyl-1-yl | OCH$_2$CF$_3$ | Cl | 1,1'-bicyclopropyl-2-yl | Cl | Br | |
| 1,1'-bicyclopropyl-2-yl | Cl | F | Me | OCH$_2$CF$_3$ | Br | 1,1'-bicyclopropyl-1-yl | Cl | Br | |
| H | Br | Cl | Et | OCH$_2$CF$_3$ | Br | H | $CF_3$ | Cl | |
| Me | Br | Cl | Me | OCF$_2$H | F | Me | $CF_3$ | Cl | |
| t-Bu | Br | Cl | Et | OCF$_2$H | F | t-Bu | $CF_3$ | Cl | |
| c-Pr | Br | Cl | c-Pr | OCF$_2$H | Cl | Me | $CF_3$ | Br | |
| c-PrCH$_2$ | Br | Cl | c-PrCH$_2$ | OCF$_2$H | Cl | Et | $CF_3$ | Br | |
| 1,1'-bicyclopropyl-2-yl | Br | Cl | 1,1'-bicyclopropyl-2-yl | OCF$_2$H | F | c-Pr | $CF_3$ | Br | |
| H | $CF_3$ | F | Me | OCF$_2$H | Br | c-PrCH$_2$ | $CF_3$ | Br | |
| Me | $CF_3$ | F | Et | OCF$_2$H | Br | 1,1'-bicyclopropyl-2-yl | $CF_3$ | Br | |
| t-Bu | $CF_3$ | F | 2-CH$_3$-c-Pr | $CF_3$ | F | 1,1'-bicyclopropyl-1-yl | $CF_3$ | F | |
| $R^2$ is Me, X is Cl, $R^{17}$ is Cl and Z is N. | | | $R^2$ is Me, X is Cl, $R^{17}$ is Cl and Z is N. | | | $R^2$ is Me, X is Cl, $R^{17}$ is Cl and Z is N. | | | |
| H | Br | F | H | Cl | Cl | H | Br | Br | |
| Me | Br | F | Me | Cl | Cl | Me | Br | Br | |
| t-Bu | Br | F | t-Bu | Cl | Cl | t-Bu | Br | Br | |
| c-Pr | Br | F | c-Pr | Cl | Cl | c-Pr | Br | Br | |

TABLE 2-continued

| | | | | | | | | |
|---|---|---|---|---|---|---|---|---|
| c-PrCH$_2$ | Br | F | c-PrCH$_2$ | Cl | Cl | c-PrCH$_2$ | Br | Br |
| 1,1'-bicyclopropyl-2-yl | Br | F | 1,1'-bicyclopropyl-2-yl | Cl | Cl | 1,1'-bicyclopropyl-1-yl | Br | Br |
| 1,1'-bicyclopropyl-1-yl | Br | F | 1,1'-bicyclopropyl-1-yl | Cl | Cl | H | Cl | Br |
| H | Cl | F | Me | OCH$_2$CF$_3$ | F | Me | Cl | Br |
| Me | Cl | F | Et | OCH$_2$CF$_3$ | F | t-Bu | Cl | Br |
| t-Bu | Cl | F | c-Pr | OCH$_2$CF$_3$ | Cl | c-Pr | Cl | Br |
| c-Pr | Cl | F | c-PrCH$_2$ | OCH$_2$CF$_3$ | Cl | c-PrCH$_2$ | Cl | Br |
| c-PrCH$_2$ | Cl | F | 1,1'-bicyclopropyl-1-yl | OCH$_2$CF$_3$ | Cl | 1,1'-bicyclopropyl-2-yl | Cl | Br |
| 1,1'-bicyclopropyl-2-yl | Cl | F | Me | OCH$_2$CF$_3$ | Br | 1,1'-bicyclopropyl-1-yl | Cl | Br |
| H | Br | Cl | Et | OCH$_2$CF$_3$ | Br | H | CF$_3$ | Cl |
| Me | Br | Cl | Me | OCF$_2$H | F | Me | CF$_3$ | Cl |
| t-Bu | Br | Cl | Et | OCF$_2$H | F | t-Bu | CF$_3$ | Cl |
| c-Pr | Br | Cl | c-Pr | OCF$_2$H | Cl | Me | CF$_3$ | Br |
| c-PrCH$_2$ | Br | Cl | c-PrCH$_2$ | OCF$_2$H | Cl | Et | CF$_3$ | Br |
| 1,1'-bicyclopropyl-2-yl | Br | Cl | 1,1'-bicyclopropyl-2-yl | OCF$_2$H | F | c-Pr | CF$_3$ | Br |
| H | CF$_3$ | F | Me | OCF$_2$H | Br | c-PrCH$_2$ | CF$_3$ | Br |
| Me | CF$_3$ | F | Et | OCF$_2$H | Br | 1,1'-bicyclopropyl-2-yl | CF$_3$ | Br |
| t-Bu | CF$_3$ | F | 2-CH$_3$-c-Pr | CF$_3$ | F | 1,1'-bicyclopropyl-1-yl | CF$_3$ | F |
| $R^2$ is Me, X is I, $R^{17}$ is Cl and Z is N. | | | $R^2$ is Me, X is I, $R^{17}$ is Cl and Z is N. | | | $R^2$ is Me, X is I, $R^{17}$ is Cl and Z is N. | | |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH$_2$ | Br | F | c-PrCH$_2$ | Cl | Cl | c-PrCH$_2$ | Br | Br |
| 1,1'-bicyclopropyl-2-yl | Br | F | 1,1'-bicyclopropyl-2-yl | Cl | Cl | 1,1'-bicyclopropyl-1-yl | Br | Br |
| 1,1'-bicyclopropyl-1-yl | Br | F | 1,1'-bicyclopropyl-1-yl | Cl | Cl | H | Cl | Br |
| H | Cl | F | Me | OCH$_2$CF$_3$ | F | Me | Cl | Br |
| Me | Cl | F | Et | OCH$_2$CF$_3$ | F | t-Bu | Cl | Br |
| t-Bu | Cl | F | c-Pr | OCH$_2$CF$_3$ | Cl | c-Pr | Cl | Br |
| c-Pr | Cl | F | c-PrCH$_2$ | OCH$_2$CF$_3$ | Cl | c-PrCH$_2$ | Cl | Br |
| c-PrCH$_2$ | Cl | F | 1,1'-bicyclopropyl-1-yl | OCH$_2$CF$_3$ | Cl | 1,1'-bicyclopropyl-2-yl | Cl | Br |
| 1,1'-bicyclopropyl-2-yl | Cl | F | Me | OCH$_2$CF$_3$ | Br | 1,1'-bicyclopropyl-1-yl | Cl | Br |
| H | Br | Cl | Et | OCH$_2$CF$_3$ | Br | H | CF$_3$ | Cl |
| Me | Br | Cl | Me | OCF$_2$H | F | Me | CF$_3$ | Cl |
| t-Bu | Br | Cl | Et | OCF$_2$H | F | t-Bu | CF$_3$ | Cl |
| c-Pr | Br | Cl | c-Pr | OCF$_2$H | Cl | Me | CF$_3$ | Br |
| c-PrCH$_2$ | Br | Cl | c-PrCH$_2$ | OCF$_2$H | Cl | Et | CF$_3$ | Br |
| 1,1'-bicyclopropyl-2-yl | Br | Cl | 1,1'-bicyclopropyl-2-yl | OCF$_2$H | F | c-Pr | CF$_3$ | Br |
| H | CF$_3$ | F | Me | OCF$_2$H | Br | c-PrCH$_2$ | CF$_3$ | Br |
| Me | CF$_3$ | F | Et | OCF$_2$H | Br | 1,1'-bicyclopropyl-2-yl | CF$_3$ | Br |
| t-Bu | CF$_3$ | F | 2-CH$_3$-c-Pr | CF$_3$ | F | 1,1'-bicyclopropyl-1-yl | CF$_3$ | F |
| $R^2$ is Cl, X is Br, $R^{17}$ is Cl and Z is N. | | | $R^2$ is Me, X is Br, $R^{17}$ is Cl and Z is N. | | | $R^2$ is Me, X is Br, $R^{17}$ is Cl and Z is N. | | |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH$_2$ | Br | F | c-PrCH$_2$ | Cl | Cl | c-PrCH$_2$ | Br | Br |
| 1,1'-bicyclopropyl-2-yl | Br | F | 1,1'-bicyclopropyl-2-yl | Cl | Cl | 1,1'-bicyclopropyl-1-yl | Br | Br |
| 1,1'-bicyclopropyl-1-yl | Br | F | 1,1'-bicyclopropyl-1-yl | Cl | Cl | H | Cl | Br |
| H | Cl | F | Me | OCH$_2$CF$_3$ | F | Me | Cl | Br |
| Me | Cl | F | Et | OCH$_2$CF$_3$ | F | t-Bu | Cl | Br |
| t-Bu | Cl | F | c-Pr | OCH$_2$CF$_3$ | Cl | c-Pr | Cl | Br |
| c-Pr | Cl | F | c-PrCH$_2$ | OCH$_2$CF$_3$ | Cl | c-PrCH$_2$ | Cl | Br |
| c-PrCH$_2$ | Cl | F | 1,1'-bicyclopropyl-1-yl | OCH$_2$CF$_3$ | Cl | 1,1'-bicyclopropyl-2-yl | Cl | Br |
| 1,1'-bicyclopropyl-2-yl | Cl | F | Me | OCH$_2$CF$_3$ | Br | 1,1'-bicyclopropyl-1-yl | Cl | Br |
| H | Br | Cl | Et | OCH$_2$CF$_3$ | Br | H | CF$_3$ | Cl |
| Me | Br | Cl | Me | OCF$_2$H | F | Me | CF$_3$ | Cl |
| t-Bu | Br | Cl | Et | OCF$_2$H | F | t-Bu | CF$_3$ | Cl |
| c-Pr | Br | Cl | c-Pr | OCF$_2$H | Cl | Me | CF$_3$ | Br |
| c-PrCH$_2$ | Br | Cl | c-PrCH$_2$ | OCF$_2$H | Cl | Et | CF$_3$ | Br |
| 1,1'-bicyclopropyl-2-yl | Br | Cl | 1,1'-bicyclopropyl-2-yl | OCF$_2$H | F | c-Pr | CF$_3$ | Br |
| H | CF$_3$ | F | Me | OCF$_2$H | Br | c-PrCH$_2$ | CF$_3$ | Br |
| Me | CF$_3$ | F | Et | OCF$_2$H | Br | 1,1'-bicyclopropyl-2-yl | CF$_3$ | Br |
| t-Bu | CF$_3$ | F | 2-CH$_3$-c-Pr | CF$_3$ | F | 1,1'-bicyclopropyl-1-yl | CF$_3$ | F |
| $R^2$ is Cl, X is I, $R^{17}$ is Cl and Z is N. | | | $R^2$ is Me, X is I, $R^{17}$ is Cl and Z is N. | | | $R^2$ is Me, X is I, $R^{17}$ is Cl and Z is N. | | |
| H | Br | F | H | Cl | Cl | H | Br | Br |
| Me | Br | F | Me | Cl | Cl | Me | Br | Br |
| t-Bu | Br | F | t-Bu | Cl | Cl | t-Bu | Br | Br |
| c-Pr | Br | F | c-Pr | Cl | Cl | c-Pr | Br | Br |
| c-PrCH$_2$ | Br | F | c-PrCH$_2$ | Cl | Cl | c-PrCH$_2$ | Br | Br |
| 1,1'-bicyclopropyl-2-yl | Br | F | 1,1'-bicyclopropyl-2-yl | Cl | Cl | 1,1'-bicyclopropyl-1-yl | Br | Br |
| 1,1'-bicyclopropyl-1-yl | Br | F | 1,1'-bicyclopropyl-1-yl | Cl | Cl | H | Cl | Br |
| H | Cl | F | Me | OCH$_2$CF$_3$ | F | Me | Cl | Br |
| Me | Cl | F | Et | OCH$_2$CF$_3$ | F | t-Bu | Cl | Br |
| t-Bu | Cl | F | c-Pr | OCH$_2$CF$_3$ | Cl | c-Pr | Cl | Br |
| c-Pr | Cl | F | c-PrCH$_2$ | OCH$_2$CF$_3$ | Cl | c-PrCH$_2$ | Cl | Br |
| c-PrCH$_2$ | Cl | F | 1,1'-bicyclopropyl-1-yl | OCH$_2$CF$_3$ | Cl | 1,1'-bicyclopropyl-2-yl | Cl | Br |

TABLE 2-continued

| | | | | | | | | | |
|---|---|---|---|---|---|---|---|---|---|
| 1,1'-bicyclopropyl-2-yl | Cl | F | Me | OCH$_2$CF$_3$ | Br | 1,1'-bicyclopropyl-1-yl | Cl | Br |
| H | Br | Cl | Et | OCH$_2$CF$_3$ | Br | H | CF$_3$ | Cl |
| Me | Br | Cl | Me | OCF$_2$H | F | Me | CF$_3$ | Cl |
| t-Bu | Br | Cl | Et | OCF$_2$H | F | t-Bu | CF$_3$ | Cl |
| c-Pr | Br | Cl | c-Pr | OCF$_2$H | Cl | Me | CF$_3$ | Br |
| c-PrCH$_2$ | Br | Cl | c-PrCH$_2$ | OCF$_2$H | Cl | Et | CF$_3$ | Br |
| 1,1'-bicyclopropyl-2-yl | Br | Cl | 1,1'-bicyclopropyl-2-yl | OCF$_2$H | F | c-Pr | CF$_3$ | Br |
| H | CF$_3$ | F | Me | OCF$_2$H | Br | c-PrCH$_2$ | CF$_3$ | Br |
| Me | CF$_3$ | F | Et | OCF$_2$H | Br | 1,1'-bicyclopropyl-2-yl | CF$_3$ | Br |
| t-Bu | CF$_3$ | F | 2-CH$_3$-c-Pr | CF$_3$ | F | 1,1'-bicyclopropyl-1-yl | CF$_3$ | F |

What is claimed is:

1. A method for preparing a compound of Formula 1

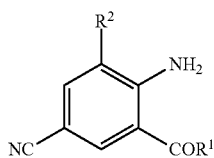

wherein
$R^1$ is NHR$^3$ or OR$^4$;
$R^2$ is CH$_3$ or Cl;
$R^3$ is H, C$_1$-C$_4$ alkyl, cyclopropyl, cyclopropylcyclopropyl, cyclopropylmethyl or methylcyclopropyl; and
$R^4$ is H or C$_1$-C$_4$ alkyl;
comprising contacting (1) a compound of Formula 2

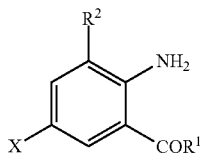

wherein each X is independently Br, Cl or I;
with (2) at least one compound of Formula 3

$$M^1CN \quad\quad 3$$

wherein M$^1$ is sodium, potassium, cesium or rubidium;
and (3) a compound of Formula 4

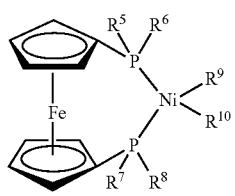

wherein
$R^5$ is a phenyl ring optionally substituted with up to 5 substituents independently selected from R$^{11}$;
$R^6$ is a phenyl ring or a naphthalenyl ring system, each ring or ring system optionally substituted with up to 5 substituents independently selected from R$^{12}$;
$R^7$ is a phenyl ring optionally substituted with up to 5 substituents independently selected from R$^{13}$;
$R^8$ is a phenyl ring or a naphthalenyl ring system, each ring or ring system optionally substituted with up to 5 substituents independently selected from R$^{14}$;
each R$^9$ and R$^{10}$ is independently a displaceable ligand; or R$^9$ and R$^{10}$ together are a bidentate, displaceable ligand; and
each R$^{11}$, R$^{12}$, R$^{13}$ and R$^{14}$ is independently fluorine, C$_1$-C$_6$ alkyl, C$_1$-C$_6$ fluoroalkyl, C$_1$-C$_6$ alkoxy, C$_1$-C$_6$ fluoroalkoxy, C$_1$-C$_6$ alkylamino or C$_2$-C$_6$ dialkylamino;
provided that when X is Cl, then R$^2$ is methyl.

2. The method of claim 1 wherein the reagents (1), (2) and (3) are contacted in the presence of a reducing agent comprising one or more compounds selected from the group consisting of metal reducing agents and silane reducing agents.

3. The method of claim 2 wherein the reducing agent comprises one or more compounds selected from the group consisting zinc and polymethylhydrosiloxane.

4. The method of claim 1 wherein R$^1$ is NHR$^3$, R$^3$ is CH$_3$, R$^2$ is CH$_3$ and X is Br or Cl.

5. The method of claim 1 wherein M$^1$ is selected from the group consisting of sodium and potassium.

6. The method of claim 1 wherein the compound of Formula 4 comprises [1,1'-bis-(diphenylphosphino)ferrocene][(1,2,5,6)-1,5-cyclooctadiene]nickel.

7. The method of claim 1 wherein the reagents (1), (2) and (3) are contacted in the presence of a suitable solvent comprising one or more nitrile solvents.

8. The method of claim 7 wherein the suitable solvent comprises one or more solvents selected from the group consisting of acetonitrile, propionitrile and butyronitrile.

9. The method of claim 8 wherein the suitable solvent comprises acetonitrile.

10. The method of claim 1 further comprising preparing the compound of Formula 4 wherein R$^9$ and R$^{10}$ together are a cycloalkadiene bidentate ligand; by contacting (i) a compound of Formula 5

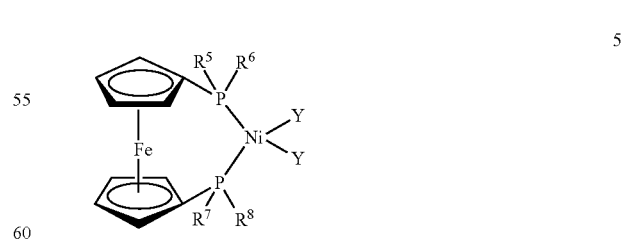

wherein each Y is independently Cl, Br or I;
with (ii) a cycloalkadiene bidentate ligand, (iii) at least one metal reducing agent and (iv) a nitrile solvent.

11. The method of claim 10 wherein each R$^5$, R$^6$, R$^7$ and R$^8$ is a phenyl ring, and R$^9$ and R$^{10}$ together are 1,5-cyclooctadiene.

12. The method of claim 1 further comprising contacting (a) a compound of Formula 5

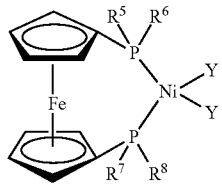

wherein each Y is independently Cl, Br or I;

with (b) a cycloalkadiene bidentate ligand and (c) at least one metal reducing agent to form a mixture comprising a compound of Formula 4 wherein $R^9$ and $R^{10}$ together are a cycloalkadiene bidentate ligand; wherein the mixture comprising the compound of Formula 4 is contacted with (1) the compound of Formula 2 and (2) the at least one compound of Formula 3.

13. The method of claim 12 wherein each $R^5$, $R^6$, $R^7$ and $R^8$ is a phenyl ring, and $R^9$ and $R^{10}$ together are 1,5-cyclooctadiene.

* * * * *